United States Patent
Tenne et al.

(10) Patent No.: US 12,365,794 B2
(45) Date of Patent: Jul. 22, 2025

(54) NANOCOMPOSITES COMPRISING BIODEGRADABLE POLYMERS AND INORGANIC NANOPARTICLES, METHODS OF PREPARATION AND USES THEREOF

(71) Applicants: YEDA RESEARCH AND DEVELOPMENT CO. LTD., Rehovot (IL); RAMOT AT TEL-AVIV UNIVERSITY LTD., Tel-Aviv (IL)

(72) Inventors: Reshef Tenne, Rehovot (IL); Hila Shalom, Rehovot (IL); Noa Lachman Senesh, Rishon LeZion (IL)

(73) Assignees: Yeda Research and Development Co. Ltd., Rehovot (IL); Ramot at Tel-Aviv University Ltd., Tel Aviv (IL)

( * ) Notice: Subject to any disclaimer, the term of this patent is extended or adjusted under 35 U.S.C. 154(b) by 670 days.

(21) Appl. No.: 17/416,766

(22) PCT Filed: Dec. 26, 2019

(86) PCT No.: PCT/IL2019/051419
§ 371 (c)(1),
(2) Date: Jun. 21, 2021

(87) PCT Pub. No.: WO2020/136656
PCT Pub. Date: Jul. 2, 2020

(65) Prior Publication Data
US 2022/0073733 A1 Mar. 10, 2022

Related U.S. Application Data

(60) Provisional application No. 62/820,993, filed on Mar. 20, 2019, provisional application No. 62/924,190, filed on Oct. 22, 2019.

(30) Foreign Application Priority Data

Dec. 27, 2018 (IL) .......................................... 264006

(51) Int. Cl.
*C08L 67/04* (2006.01)
*B29C 64/118* (2017.01)
(Continued)

(52) U.S. Cl.
CPC ............ *C08L 67/04* (2013.01); *B29C 64/118* (2017.08); *B29C 71/02* (2013.01);
(Continued)

(58) Field of Classification Search
CPC ... C08L 67/04; C08K 3/045; C08K 2201/005; C08K 2201/011; B29C 64/118; B29C 71/02
See application file for complete search history.

(56) References Cited

U.S. PATENT DOCUMENTS

| 8,329,138 B2 | 12/2012 | Tenne et al. |
| 8,518,364 B2 | 8/2013 | Tenne et al. |

(Continued)

FOREIGN PATENT DOCUMENTS

| CN | 101949046 | 1/2011 |
| CN | 105274603 | 1/2016 |

(Continued)

OTHER PUBLICATIONS

Naffakh et al. Development of novel melt-processable biopolymer nanocomposites based on poly(L-lactic acid) and WS2 inorganic nanotubes. CrystEngComm, 2014, 15, 5062. (Year: 2014).*
(Continued)

*Primary Examiner* — John E Uselding
(74) *Attorney, Agent, or Firm* — Mark S. Cohen; PEARL COHEN ZEDEK LATZER BARATZ LLP

(57) ABSTRACT

This invention is directed to nanocomposite comprising biodegradable polymers and inorganic nanoparticles or nanotubes, methods of preparation and uses thereof.

17 Claims, 25 Drawing Sheets

(51) Int. Cl.
  *B29C 71/02* (2006.01)
  *B29K 67/00* (2006.01)
  *B82Y 40/00* (2011.01)
  *C08K 3/04* (2006.01)
(52) U.S. Cl.
  CPC .. *B29C 2071/022* (2013.01); *B29K 2067/046* (2013.01); *B82Y 40/00* (2013.01); *C08K 3/045* (2017.05); *C08K 2201/005* (2013.01); *C08K 2201/011* (2013.01)

(56) References Cited

U.S. PATENT DOCUMENTS

| | | | |
|---|---|---|---|
| 9,155,595 | B2 | 10/2015 | Tenne et al. |
| 9,242,231 | B2 | 1/2016 | Tenne et al. |
| 9,496,067 | B2 | 11/2016 | Tenne et al. |
| 9,527,735 | B2 | 12/2016 | Tenne et al. |
| 9,877,806 | B2 | 1/2018 | Tenne et al. |
| 2006/0165926 | A1 | 7/2006 | Weber |
| 2007/0259101 | A1 | 11/2007 | Kleiner et al. |
| 2012/0021014 | A1 | 1/2012 | Chantalat et al. |
| 2014/0138319 | A1 | 5/2014 | Fu-Giles |
| 2014/0287264 | A1 | 9/2014 | Tenne et al. |
| 2015/0073560 | A1 | 3/2015 | Sahvit |
| 2016/0133925 | A1 | 5/2016 | Tenne et al. |
| 2016/0331874 | A1 | 11/2016 | Tenne et al. |
| 2017/0066188 | A1 | 3/2017 | Luo et al. |
| 2018/0171435 | A1 | 6/2018 | Tenne et al. |

FOREIGN PATENT DOCUMENTS

| | | |
|---|---|---|
| CN | 108610502 A | 2/2018 |
| KR | 2013-0053954 | 5/2013 |
| WO | WO 2006/123336 | 11/2006 |
| WO | WO 2009/034572 | 3/2009 |
| WO | WO 2011/111044 | 9/2011 |
| WO | WO 2011/161676 | 12/2011 |
| WO | WO 2013/057732 | 4/2013 |
| WO | WO 2014/033718 | 3/2014 |
| WO | WO 2014/203251 | 12/2014 |
| WO | WO 2015/102006 | 7/2015 |
| WO | WO 2015/170331 | 11/2015 |
| WO | WO 2016/193974 | 12/2016 |
| WO | WO 2017/163250 | 9/2017 |
| WO | WO 2018/086520 | 5/2018 |
| WO | WO 2018/122848 | 7/2018 |
| WO | WO 2019/162943 | 2/2019 |

OTHER PUBLICATIONS

Li et al. Nanocellular Foaming Behaviors of Chain-Extended Poly(lactic acid) Induced by Isothermal Crystallization. ACS Omega 2019, 4, 12512-12523) (Year: 2019).*
Rheonis The Different Viscosities https://rheonis.com/en/the-different-viscosities-of-fluid-mechanics-polymer-physics-rheology/#:~:text=La%20inherent%20viscosity%20is%20the,polymer%20concentration%20tends%20towards%200. Accessed Mar. 13, 2024 (Year: 2022).*
Panich et al. Nuclear Magnetic Resonance Study of Fullerene-Like WS2. J. Nanosci. Nanotechnol. 2006, vol. 6, No. 6. (Year: 2006).*
Database WPI, Week 201433, Thomson Scientific, London, GB, An 2014-J44678, 2 pages, 2014.
EP Application No. EP19836845.8 Office Action dated Jun. 23, 2023.
Naffakh et al. (2015). WS 2 inorganic nanotubes reinforced poly (I-lactic acid)/hydroxyapatite hybrid composite biomaterials. *RSC advances*, 5(80), 65514-65525.
Alberdi et al. (2011). Tribological behavior of nanocomposite coatings based on fullerene-like structures. Vacuum, 85(12):1087-92.
Andre et al. (2012). Performance and tribofilm formation of a low-friction coating incorporating inorganic fullerene like nanoparticles. Surface and Coatings Technology, 206(8-9):2325-9.
Angjellari et al. (2017). Beyond the concepts of nanocomposite and 3D printing: PVA and nanodiamonds for layer-by-layer additive manufacturing. Materials & Design, 119, 12-21.
Aninwene et al. (2008). Enhanced osteoblast adhesion to drug-coated anodized nanotubular titanium surfaces. International journal of nanomedicine, 3(2):257.
Appel et al. (2016). Low cytotoxicity and genotoxicity of two-dimensional MoS2 and WS2. Acs Biomaterials Science & Engineering, 2(3):361-7.
Assefpour-Dezfuly et al. (1984). Oxide morphology and adhesive bonding on titanium surfaces. Journal of materials science, 19(11):3626-39.
Basnyat et al. (2007). Mechanical and tribological properties of CrAlN—Ag self-lubricating films. Surface and Coatings Technology, 202(4-7):1011-6.
Cambell et al. (2013). 3D printing of multifunctional nanocomposites. Nano Today, 8(2), 119-120.
Carrasco et al. (2010). Processing of poly (lactic acid): Characterization of chemical structure, thermal stability and mechanical properties. Polymer Degradation and stability, 95(2), 116-125.
Cassanas et al. (1991). Vibrational spectra of lactic acid and lactates. Journal of Raman spectroscopy, 22(7), 409-413.
Cataldi et al. (2016). Effect of graphene nano-platelet morphology on the elastic modulus of soft and hard biopolymers. Carbon, 109, 331-339.
Chen et al. (1985). Raman study of vibrational relaxation in dichloromethane and [2 H 2] dichloromethane. Journal of the Chemical Society, Faraday Transactions 2: Molecular and Chemical Physics, 81(2), 235-243.
Chen et al. (1998). Calcium phosphate coating on titanium substrate by a modified electrocrystallization process. Journal of Materials Science: Materials in Medicine, 9(5):297-300.
Chen et al. (2018). Enhanced thermal and mechanical properties of PLA/MoS2 nanocomposites synthesized via the in-situ ring-opening polymerization. Applied Surface Science, 440, 1143-1149.
Dul et al. (2016). Fused deposition modelling with ABS-graphene nanocomposites. Composites: Part A, 85, 181-191.
Dutrow, BL (2016). X-ray Powder Diffraction, available at: https://serc.carleton.edu/research_education/geochemsheets/techniques/XRD.html.
Farahani et al. (2016). Three-dimensional printing of multifunctional nanocomposites: manufacturing techniques and applications. Advanced materials, 28(28), 5794-5821.
Fischer et al. (1973). Investigation of the structure of solution grown crystals of lactide copolymers by means of chemical reactions. Kolloid-Zeitschrift und Zeitschrift für Polymere, 251(11), 980-990.
Friedman et al. "Fabrication of self-lubricating cobalt coatings on metal surfaces" Nanotechnology. Feb. 7, 2007;18(11):115703.
Friedrich. (2018). Polymer composites for tribological applications. Advanced Industrial and Engineering Polymer Research, 1(1), 3-39.
Fusaro RL (1990). Self-lubricating polymer composites and polymer transfer film lubrication for space applications. Tribology International, 23(2):105-22.
Gnanasekaran et al. (2017). 3D printing of CNT- and graphene-based conductive polymer nanocomposites by fused deposition modeling. Applied materials today, 9, 21-28.
Goldbart, O et al. (2014). Lubricating medical devices with fullerene-like nanoparticles. Tribology Letters, 55(1), 103-109.
Goldman et al. (2014). Biocompatibility of tungsten disulfide inorganic nanotubes and fullerene-like nanoparticles with salivary gland cells. Tissue Engineering Part A, 21(5-6):1013-23.
Gong et al. (2001). Titanium oxide nanotube arrays prepared by anodic oxidation. Journal of Materials Research, 16(12):3331-4.
Grinberg et al. (2017). Raman scattering from single WS 2 nanotubes in stretched PVDF electrospun fibers. Physical Chemistry Chemical Physics, 19(28), 18443-18451.
Hernandez et al. (2008). High-yield production of graphene by liquid-phase exfoliation of graphite. Nature nanotechnology, 3(9), 563-568.
Ivanova, R. et al. (2018). Rheological study of poly (lactic) acid nanocomposites with carbon nanotubes and graphene additives as a tool for materials characterization for 3D printing application. Applied Rheology, 28(5).

(56) References Cited

OTHER PUBLICATIONS

Kaplan-Ashiri et al. (2006). On the mechanical behavior of WS2 nanotubes under axial tension and compression. Proceedings of the National Academy of Sciences, 103(3), 523-528.

Katz et al. (2006). Self-lubricating coatings containing fullerene-like WS 2 nanoparticles for orthodontic wires and other possible medical applications. Tribology Letters, 21(2), 135-139.

Kazemzadeh-Narbat et al. (2010). Antimicrobial peptides on calcium phosphate-coated titanium for the prevention of implant-associated infections. Biomaterials, 31(36):9519-26.

Kim et al. (2005). Physicochemical characterization of poly (L-lactic acid) and poly (D, L-lactide-co-glycolide) nanoparticles with polyethylenimine as gene delivery carrier. International journal of pharmaceutics, 298(1), 255-262.

Kister et al. (1995). Vibrational analysis of poly (L-lactic acid). Journal of Raman Spectroscopy, 26(4), 307-311.

Kister et al. (1998). Effects of morphology, conformation and configuration on the IR and Raman spectra of various poly (lactic acid) s. Polymer, 39(2), 267-273.

Kraitazer (2010). Bone graft and calcium sulfate overview. Augma Biomaterials, pp. 24-32.

Lahiri et al. (2010). Carbon nanotube toughened hydroxyapatite by spark plasma sintering: microstructural evolution and multiscale tribological properties. Carbon, 48(11):3103-20.

Lahiri et al. (2011). Boron nitride nanotube reinforced hydroxyapatite composite: mechanical and tribological performance and in-vitro biocompatibility to osteoblasts. Journal of the mechanical behavior of biomedical materials, 4(1):44-56.

Lee et al. (2017). Fundamentals and applications of 3D printing for novel materials. Applied materials today, 7, 120-133.

Legeros et al. (2003). iphasic calcium phosphate bioceramics: preparation, properties and applications. Journal of materials science: Materials in Medicine, 14(3):201-9.

Li et al. (2008). Tribological properties of nickel-based self-lubricating composite at elevated temperature and counterface material selection. Wear, 265(3-4):533-9.

Lian et al. "Friction and wear behavior of WS 2/Zr self-lubricating soft coatings in dry sliding against 40Cr-hardened steel balls" Tribology Letters. Jan. 1, 2014;53(1):237-46.

Ligon et al. et al.(2017). Polymers for 3D printing and customized additive manufacturing. Chemical reviews, 117(15), 10212-10290.

Macák et al. (2005). High-aspect-ratio TiO2 nanotubes by anodization of titanium. Angewandte Chemie International Edition, 44(14):2100-2.

Manzeli et al. (2017). 2D transition metal dichalcogenides. Nature Reviews Materials, 2(8):17033.

Mathew et al. (2019). Fused deposition modeling as an effective tool for anti-infective dialysis catheter fabrication. ACS Biomaterials Science & Engineering, 5(11), 6300-6310.

Migliaresi et al. (1991). Dynamic mechanical and calorimetric analysis of compression-molded PLLA of different molecular weights: effect of thermal treatments. Journal of applied polymer science, 43(1), 83-95.

Moghadam et al. (2015). Mechanical and tribological properties of self-lubricating metal matrix nanocomposites reinforced by carbon nanotubes (CNTs) and graphene—a review. Composites Part B: Engineering, 77:402-20.

Molitor et al. (2001). Surface treatment of titanium for adhesive bonding to polymer composites: a review. International Journal of Adhesion and Adhesives, 21(2):129-36.

Naffakh et al. (2014). Inorganic WS 2 nanotubes that improve the crystallization behavior of poly (3-hydroxybutyrate). CrystEngComm, 16(6), 1126-1135.

Naffakh et al. (2015). Isothermal crystallization kinetics and melting behavior of poly (l-lactic acid)/WS 2 inorganic nanotube nanocomposites. Journal of materials science, 50(18), 6066-6074.

Naffakh et al. (2015). Non-isothermal cold-crystallization behavior and kinetics of poly (L-lactic acid)/WS2 inorganic nanotube nanocomposites. Polymers, 7(11), 2175-2189.

Naffakh, M. et al. (2014). Development of novel melt-processable biopolymer nanocomposites based on poly (l-lactic acid) and WS 2 inorganic nanotubes. CrystEngComm, 16(23), 5062-5072.

Naffakh, M. et al. (2014). Novel poly (3-hydroxybutyrate) nanocomposites containing WS2 inorganic nanotubes with improved thermal, mechanical and tribological properties. Materials Chemistry and Physics, 147(1-2), 273-284.

Naffakh, M. et al. (2016). Polymer blend nanocomposites based on poly (l-lactic acid), polypropylene and WS 2 inorganic nanotubes. RSC advances, 6(46), 40033-40044.

Ngo et al., (2018). Additive manufacturing (3D printing): A review of materials, methods, applications and challenges. Composites Part B: Engineering, 143, 172-196.

Pardo et al. (2014). Low cytotoxicity of inorganic nanotubes and fullerene-like nanostructures in human bronchial epithelial cells: relation to inflammatory gene induction and antioxidant response. Environmental science & technology, 48(6):3457-66.

Petit R. (1999). The use of hydroxyapatite in orthopaedic surgery: a ten-year review. European Journal of Orthopaedic Surgery & Traumatology, 9(2):71-4.

Pham et al. (2011). Chemical functionalization of graphene sheets by solvothermal reduction of a graphene oxide suspension in N-methyl-2-pyrrolidone. Journal of Materials Chemistry, 21(10), 3371-3377.

Polcar et al. (2011). Properties of nanocomposite film combining hard TiN matrix with embedded fullerene-like WS2 nanoclusters. Thin Solid Films, 519(10):3191-5.

Potschke (2002). Rheological behavior of multiwalled carbon nanotube/polycarbonate composites. Polymer, 43(11), 3247-3255.

Rapoport et al. (1997). Hollow nanoparticles of WS 2 as potential solid-state lubricants. Nature, 387(6635), 791-793.

Rapoport et al.(2005). Applications of WS 2 (MoS 2) inorganic nanotubes and fullerene-like nanoparticles for solid lubrication and for structural nanocomposites. Journal of Materials Chemistry, 15(18), 1782-1788.

Rey et al. (2007). Nanocrystalline apatites in biological systems: characterisation, structure and properties. Materialwissenschaft und Werkstofftechnik, 38(12):996-1002.

Rezwan et al. (2006). Biodegradable and bioactive porous polymer/inorganic composite scaffolds for bone tissue engineering. Biomaterials, 27(18), 3413-3431.

Richa et al.(2002). In vitro evaluation of poly (ε-caprolactone-co-DL-lactide)/bioactive glass composites. Biomaterials, 23(10), 2143-2150.

Rodriguez-Lugo et al. (2005). Synthesis and Structural Characterization of Hydroxyapatite Obtained from CaO and CaHP04 by a Hydrothermal Method. Materials Research Innovations, 9(1):20-2.

Rosentsveig et al. (2009). Fullerene-like MoS 2 nanoparticles and their tribological behavior. Tribology Letters, 36(2), 175-182.

Rosentsveig et al. (2017). Doping of Fullerene-Like MoS2 Nanoparticles with Minute Amounts of Niobium. Particle & Particle Systems Characterization, 35(3):1700165.

Roy et al. (2011). TiO2 nanotubes: synthesis and applications. Angewandte Chemie International Edition, 50(13):2904-39.

Rozenberg et al. (2008). Polymer-assisted fabrication of nanoparticles and nanocomposites. Progress in polymer science, 33(1), 40-112.

Sacchetti et al. (2013). Surface polyethylene glycol conformation influences the protein corona of polyethylene glycol-modified single-walled carbon nanotubes: potential implications on biological performance. ACS nano, 7(3), 1974-1989.

Sahu, M. et al. (2017). Noncovalently functionalized tungsten disulfide nanosheetsfor enhanced mechanical and thermal properties of epoxy nanocomposites. ACS applied materials & interfaces, 9(16), 14347-14357.

Samorodnitzky-Naveh et al. (2009). Inorganic fullerene-like tungsten disulfide nanocoating for friction reduction of nickel-titanium alloys. Nanomedicine, 4(8), 943-950.

Search Report issued for Corresponding PCT Application No. PCT/IL2019/051419 dated Mar. 30, 2020.

Search Report issued for Related Israeli Application No. 257697 dated Dec. 18, 2018.

Search Report issued for Related PCT Application No. PCT/IL2019/050203 dated May 6, 2019.

(56) References Cited

OTHER PUBLICATIONS

Sedova et al. (2014). Re-doped fullerene-like MoS2 nanoparticles in relationship with soft lubrication. Nanomaterials and Energy, 4(1):30-8.

Sedova et al. (2015). Reinforcing silica aerogels with tungsten disulfide nanotubes. The Journal of Supercritical Fluids, 106, 9-15.

Shalom et al. (2019). Nanocomposite of poly (L-lactic acid) with inorganic nanotubes of WS2. Lubricants, 7(3), 28.

Shenoy. (2013). Rheology of filled polymer systems. Springer Science & Business Media. pp. 1-483.

Singh, I. et al. (2006). Bioactive ceramic coatings containing carbon nanotubes on metallic substrates by electrophoretic deposition. Journal of Materials Science, 41(24), 8144-8151.

Skeldon et al. (1997). Formation and characterization of self-lubricating MoS2 precursor films on anodized aluminium. Wear, 206(1-2):187-96.

Song et al. (2005). Influence of dispersion states of carbon nanotubes on physical properties of epoxy nanocomposites. Carbon, 43(7), 1378-1385.

Sridhar (2002). Electrophoretic deposition of hydroxyapatite coatings and corrosion aspects of metallic implants. Corrosion reviews, 20(4-5):255-94.

Steffe (1996). Rheological methods in food process engineering. Freeman press. pp. 1-428.

Tammaro, L. et al. (2018). Effect of tungsten disulfide (WS2) nanotubes on structural, morphological and mechanical properties of poly (L-Lactide)(PLLA) films. In AIP Conference Proceedings (vol. 1981, No. 1, p. 020073). AIP Publishing LLC.

Tenne et al. (1992). Polyhedral and cylindrical structures of tungsten disulphide. Nature, 360(6403), 444-446.

Tenne et al. (2010). Recent progress in the research of inorganic fullerene-like nanoparticles and inorganic nanotubes. Chemical Society Reviews, 39(5), 1423-1434.

Tenne R. (2003). Advances in the synthesis of inorganic nanotubes and fullerene-like nanoparticles. Angewandte Chemie International Edition, 42(42):5124-32.

Tenne R. (2006). Inorganic nanotubes and fullerene-like nanoparticles. Journal of materials research, 21(11):2726-43.

Van De Velde et al. (2002). Biopolymers: overview of several properties and consequences on their applications. Polymer testing, 21(4), 433-442.

Visser et al., (2019). Applications of 3D printing in medicine; 5 years later. Nederlands tijdschrift voor geneeskunde, 163.

Wang et al., (2017). 3D printing of polymer matrix composites: A review and prospective. Composites Part B: Engineering, 110, 442-458.

Weizmann—*Chemical Research Support—electron-microscopy* (2016). Weizmann; available at: https://www.weizmann.ac.il/ChemicalResearchSupport/electron-microscopy/instrumentation.

Weizmann—Chemical Research Support—x-ray-diffraction. (2016). Weizmann; available at: https://www.weizmann.ac.il/ChemicalResearchSupport/x-ray-diffraction/about-the-service.

Yadgarov et al (2013). Tribological studies of rhenium doped fullerene-like MoS2 nanoparticles in boundary, mixed and elasto-hydrodynamic lubrication conditions. Wear, 297(1-2):1103-10.

Yadgarov et al. (2012). Controlled Doping of MS2 (M=W, Mo) Nanotubes and Fullerene-like Nanoparticles. Angewandte Chemie International Edition, 51(5):1148-51.

Yadgarov et al. (2012). Investigation of Rhenium-Doped MoS2 Nanoparticles with Fullerene-Like Structure. Zeitschrift für anorganische und allgemeine Chemie, 638(15):2610-6.

Yadgarov et al. (2014). Dependence of the absorption and optical surface plasmon scattering of mos2 nanoparticles on aspect ratio, size, and media. ACS nano, 8(4):3575-83.

Yao et al. (2006). Anodization: a promising nano-modification technique of titanium implants for orthopedic applications. Journal of nanoscience and nanotechnology, 6(9-10):2682-92.

Ye, C. et al. (2018). Preparation of Poly (lactic-co-glycolic acid)-Based Composite Microfibers for Postoperative Treatment of Tumor in NIR I and NIR II Biowindows. Macromolecular bioscience, 18(10), 1800206.

Zhao et al. (2017). PEGylated molybdenum dichalcogenide (PEG-MoS 2) nanosheets with enhanced peroxidase-like activity for the colorimetric detection of $H_2O_2$. New Journal of Chemistry, 41(14), 6700-6708.

Zhou et al. (2006). The thermal effects on electrospinning of polylactic acid melts. Polymer, 47(21), 7497-7505.

\* cited by examiner

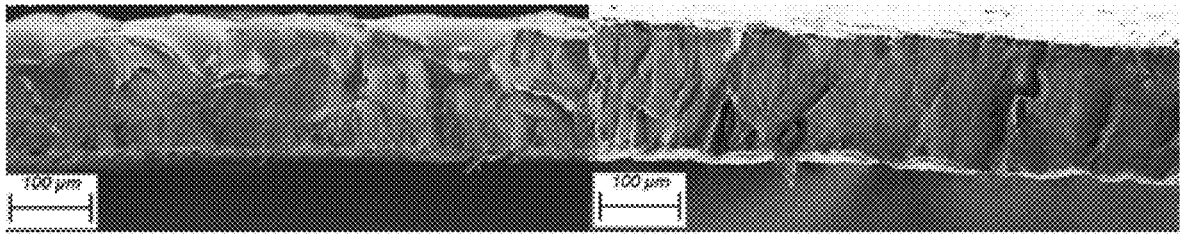
FIGURE 1A FIGURE 1B
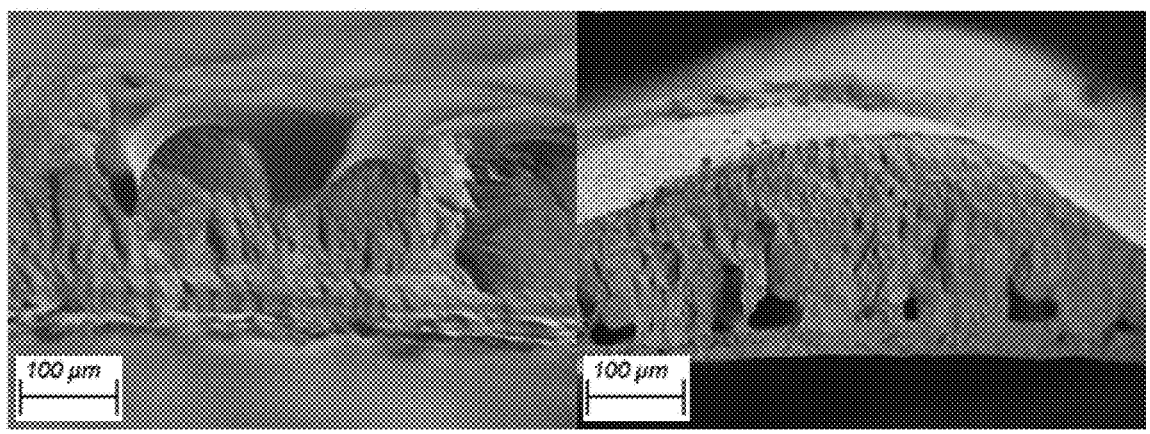
FIGURE 2A FIGURE 2B
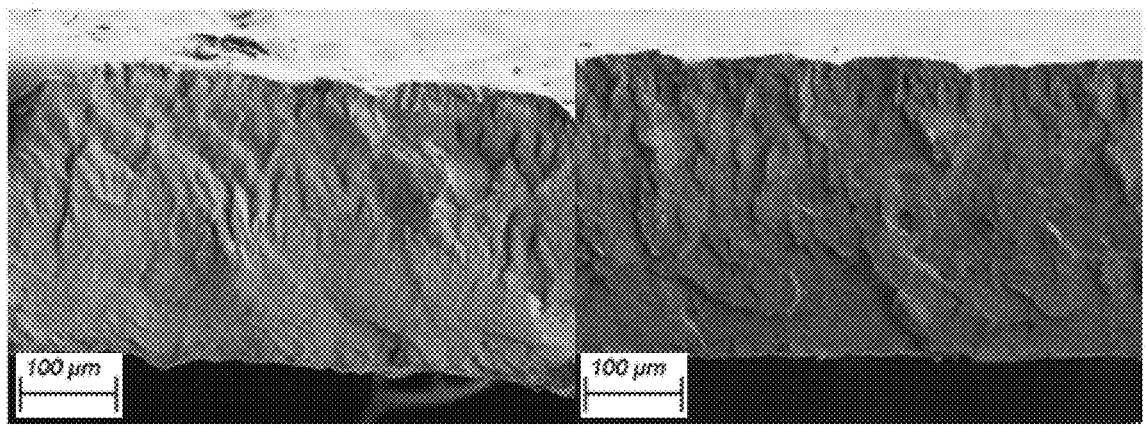
FIGURE 2C FIGURE 2D

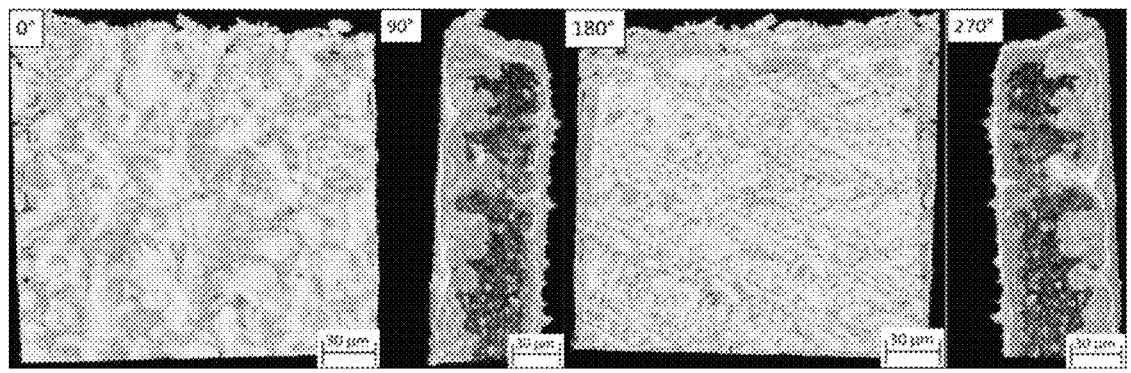
FIGURE 13A  FIGURE 13B  FIGURE 13C  FIGURE 13D
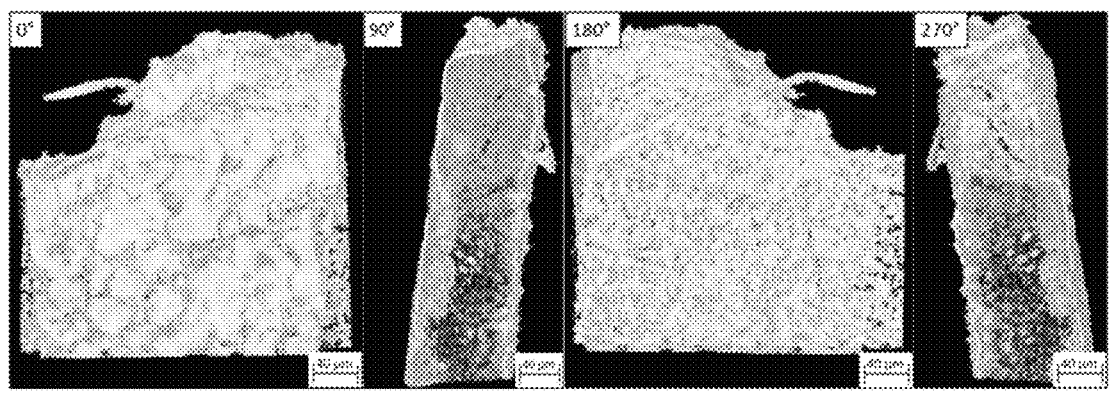
FIGURE 14A  FIGURE 14B  FIGURE 14C  FIGURE 14D
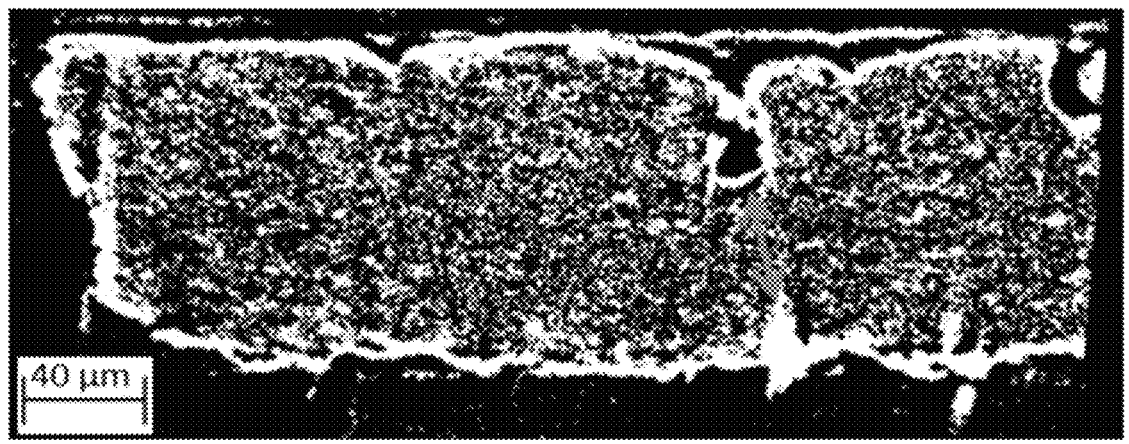
FIGURE 15

NANOCOMPOSITES COMPRISING BIODEGRADABLE POLYMERS AND INORGANIC NANOPARTICLES, METHODS OF PREPARATION AND USES THEREOF

CROSS-REFERENCE TO RELATED APPLICATIONS

This application is a National Phase Application of PCT International Application No. PCT/IL2019/051419, International Filing Date Dec. 26, 2019, claiming priority from Israel Patent Application No. 264006, filed on Dec. 27, 2018, U.S. provisional patent application No. 62/820,993, filed on Mar. 20, 2019, and U.S. provisional patent application No. 62/924,190, filed on Oct. 22, 2019, which are hereby incorporated by reference.

FIELD OF THE INVENTION

This invention is directed to nanocomposite comprising biodegradable polymers and inorganic nanoparticles or nanotubes, methods of preparation and uses thereof.

BACKGROUND OF THE INVENTION

Biodegradable polymers are commonly used in numerous applications such as food industry, medical implants, pharmaceuticals, packaging and more. They are processed via many techniques, like extrusion, inject molding, solvent casting and more (K. Van de Velde, P. K. (2002). "Biopolymers: overview of several properties and consequences on their applications." Polymer Testing 21 433-442). One of these polymers is poly(lactic acid) (PLA), which is compostable thermoplastic derived from renewable plant sources, such as starch and sugar.

Since lactic acid is a chiral molecule, PLA exists in three forms: L-PLA (PLLA), D-PLA (PDLA), and a racemic mixture of D, L-PLA (PDLLA). They all are biodegradable, compostable, nontoxic to the human body and the environment. PDLLA is always amorphous and degrades in about 1 year, therefore is usually considered for applications like drug delivery. On the other hand, total absorption of the semicrystalline PLLA, takes longer than 5 years period (total absorption). Therefore, PLLA is preferred in applications where high mechanical strength and toughness are required. PDLLA is a random copolymer that consists of L-lactic acid and D-lactic acid monomers, therefore it is amorphous and cannot exhibit crystalline structures. Its strength and modulus are lower than those of PGA and PLLA (Rezwan, K., et al. (2006). "Biodegradable and bioactive porous polymer/inorganic composite scaffolds for bone tissue engineering." Biomaterials 27(18): 3413-3431; and Richa, J., et al. (2002). "In vitro evaluation of poly(e-caprolactone-co-DL-lactide)/bioactive glass composites." Biomaterials 23 2143-2150).

Inorganic nanotubes (INT) and fullerene-like (IF) nanoparticles of layered metal dichalcogenides $MX_2$ (M=transition metal, Mo, W, etc.; X=S, Se, Te) were first reported in 1992. The layers are stacked together via weak Van der Waals forces and are covalently bonded between each transition metal atom to the six chalcogen atoms (R. Tenne et al. (1992), "Polyhedral and cylindrical structures of tungsten disulfide", Nature 360: 444-446; and Tenne, R. (2003). "Advances in the synthesis of inorganic nanotubes and fullerene-like nanoparticles." Angew. Chem. Int. Ed. Engl 0.42(42): 5124-5132). The INT (inorganic nanotube) nanostructures are 1-20 micron long with diameter of 30-150 nm (aspect ratio of 100 and larger). They exhibit very good mechanical properties. For example, the Young's modulus of $INT-WS_2$ is around 150-170 GPa, bending modulus of 217 GPa, tensile strength between 16-22 GPa and their strain $\epsilon > 10\%$ (Kaplan-Ashiri, I., et al. (2006). "On the mechanical behavior of WS2 nanotubes under axial tension and compression." Proc. Natl. Acad. Sci. USA 103 (3): 523-528; and Rozenberg, B. A. and R. Tenne (2008). "Polymer-assisted fabrication of nanoparticles and nanocomposites." Progress in Polymer Science 33(1): 40-112). In addition, the $INT-WS_2$ are chemically stable up to a temperature close to 350° C. in an oxidizing atmosphere and beyond 1000° C. in a reducing or neutral atmosphere. $INT-WS_2$ can be readily dispersed in organic solvents, polymers, epoxy polymer. Incorporating the nanotubes (0.1-2 wt %) into different polymers and inorganic phases, was shown to improve the mechanical and thermal behavior of different nanocomposites (Sedova, A., et al. (2015). "Reinforcing silica aerogels with tungsten disulfide nanotubes." The Journal of Supercritical Fluids 106: 9-15). Further, the $INT-WS_2$ and also other inorganic particles like IF (inorganic fullerene)—$MoS_2$, $INT-MoS_2$ and $IF-WS_2$ exhibit excellent tribological properties when added in small amounts to a variety of lubricating fluids, offering them numerous applications (Katz, A., et al. (2006). "Self-lubricating coatings containing fullerene-like WS2 nanoparticles for orthodontic wires and other possible medical applications." Tribology Letters 21(2): 135-139; Rapoport, L., et al. (2005). "Applications of $WS_2$ ($MoS_2$) inorganic nanotubes and fullerene-like nanoparticles for solid lubrication and for structural nanocomposites." Journal of Materials Chemistry 15(18): 1782; Rosentsveig, R., et al. (2009). "Fullerene-like $MoS_2$ Nanoparticles and Their Tribological Behavior." Tribology Letters 36(2): 175-182; and Samorodnitzky-Naveh, G. R. R., M.; Rapoport, L.; Fedman, Y.; Tenne, R. (2009). "Inorganic Fullerene-like Tungsten Disulfide Nanocoating for Friction Reduction of Nickel-titanium Alloys." Nanomedicine 4: 943-950).

This invention provides nanocomposites comprising inorganic nanoparticles such as $WS_2$, $MoS_2$ and a biodegradable polymer such as poly(lactic acid) and poly(lactic-co-glycolic acid), methods of preparation and uses thereof.

SUMMARY OF THE INVENTION

In one aspect, this invention provides a nanocomposite comprising a polymer and an anhydrous $MX_2$-based fullerene-like nanoparticles or nanotubes; wherein said polymer is selected from poly(lactic acid), poly (lactic-co-glycolic acid) or a combination thereof; M is Mo, W, Ta or Nb; and X is S, Se or Te; wherein the weight percentage of the $MX_2$-based fullerene-like nanoparticles or nanotubes from total the weight of said nanocomposite is between 0.25% and 3% and the composite has at least one of the following properties: modulus between 1.6-4 GPa; toughness (area below the stress-strain curve) between 1.1-40 MPa/%; static friction coefficient, $\mu_s$, between 0.055-0.08; kinetic friction coefficient, $\mu_s$, between 0.02-0.05; yield strength: between 15-75 MPa; and friction force reduced by between 10-99% compared to the polymer alone.

In one embodiment, the anhydrous $MX_2$-based nanotubes are $WS_2$ nanotubes ($INT-WS_2$).

In another aspect, this invention provides a method for the preparation of a nanocomposite, said nanocomposite comprises an anhydrous $MX_2$-based fullerene-like nanoparticles or nanotubes and a polymer selected from poly(lactic acid), poly (lactic-co-glycolic acid) or a combination thereof, wherein M is Mo, W, Ta or Nb; and X is S, Se or Te; wherein said method comprises:

dissolving said polymer in a first solvent;
dissolving said $MX_2$-based fullerene-like nanoparticles or nanotubes in a second solvent;
mixing together both said solutions;
solvent casting said mixed solution; and
drying the mixed solution to obtain the nanocomposite.

In another embodiment, the polymer is dried prior to its dissolving step. In another embodiment, the mixed solution is dried to form a film followed by an annealing step.

In another aspect, this invention provides a nanocomposite prepared according to the method of this invention.

In some embodiments, the nanocomposite of this invention is used in 3D printing.

In one further aspect, this invention provides a medical device or product comprising a nanocomposite of this invention.

BRIEF DESCRIPTION OF THE DRAWINGS

The subject matter regarded as the invention is particularly pointed out and distinctly claimed 25 in the concluding portion of the specification. The invention, however, both as to organization and method of operation, together with objects, features, and advantages thereof, may best be understood by reference to the following detailed description when read with the accompanying drawings in which:

FIGS. 1A-1B depict SEM images of PLLA 38 film's cross section: FIG. 1A: PLLA 38 film after drying in vacuum; and FIG. 1B: PLLA 38 film dried in the hood.

FIGS. 2A-2D depict SEM images of the cross-section of PLLA 24 films. FIG. 2A: PLLA 24 film after drying in vacuum; FIG. 2B; PLLA 24 with 0.5 wt % $INT-WS_2$ film after vacuum drying; FIG. 2C: PLLA 24 film dried in the hood; and FIG. 2D: PLLA 24 with 0.5 wt % $INT-WS_2$ film after drying in the hood.

FIG. 3A: PLLA 38; and FIG. 3B: PLLA 24. The results for each specimen represent an average value of 5 samples.

FIG. 5A: PLLA 24; and FIG. 5B—PLLA 38. The $WS_2$ nanotubes are marked in black (FIG. 5A) or white (FIG. 5B) arrows.

FIG. 6A: 0°; FIG. 6B: 90°; FIG. 6C: 180°; and FIG. 6D: 270°.

FIG. 7A: 0°; FIG. 7B: 90°; FIG. 7C: 180°; and FIG. 7D: 270°.

FIG. 8A: 0°; FIG. 8B: 900; FIG. 8C: 180°; and FIG. 8D: 270°.

FIG. 9A: 0°; FIG. 9B: 90°; FIG. 9C: 180°; and FIG. 9D: 270°.

FIG. 10A: 00; FIG. 10B: 90°; FIG. 10C: 180°; and FIG. 10D: 270°.

FIG. 11A: 0°; FIG. 11B: 90°; FIG. 11C: 180°; and FIG. 11D: 270°.

FIG. 12A: 0°; FIG. 12B: 90°; FIG. 12C: 180°; and FIG. 12D: 270°.

FIGS. 13A-13D depict images from the 360° video in the micro-XCT of PLLA 24 film with 0.5 wt % $INT-WS_2$ (sample 5; see table 5) with short extension before tensile test; scale: 40 μm. The stripes visible in 0° are obtained by the surface modulation of the Teflon container used for the preparation of the specimen. FIG. 13A: 0°; FIG. 13B: 90°; FIG. 13C: 180°; and FIG. 13D: 270°.

FIGS. 14A-14D depict images from the 360° video in the micro-XCT of PLLA 24 film with 0.5 wt % $INT-WS_2$ (sample 5; see table 5) with short extension after tensile test; scale: 40 μm. The stripes visible in 0° are obtained by the surface modulation of the Teflon container used for the preparation of the specimen. FIG. 14A: 0°; FIG. 14B: 90°; FIG. 14C: 180°; and FIG. 14D: 270°.

FIG. 15 depicts an image from the YZ slicing of the micro-XCT video of PLLA 24 film with 0.5 wt % $INT-WS_2$ (sample 5; see table 5) with short extension before the tensile test; scale: 40 μm. The white contrast are the nanotubes in the PLLA polymer. The grey double-headed arrow points to a "bowl" of nanotubes at the top; and to nanotubes agglomeration at the bottom.

FIGS. 17A-17B depict SEM images of: FIG. 17A: PLLA 38 film with 1 wt % $INT-WS_2$ after treatment with NMP and vacuum annealing for 6 h in 120° C.; and FIG. 17B: cross-section of the film.

FIG. 18A: DSC of samples immediately after preparation; and FIG. 18B: DSC of samples after one year.

FIG. 18B: PLLA 38 film with 1 wt % $INT-WS_2$; and FIG. 18C: PLLA 38 wires with 1 wt % $INT-WS_2$.

FIG. 22A: The stainless steel (uncoated) rod is inserted to the RTV ring which is fixed between two circular metal pieces; and FIG. 22B: The stainless steel (uncoated) rod is outside the UM.

FIG. 25B: DCM (at 700 cm$^{-1}$); FIG. 25C: monomers of lactic acid (at 820 cm$^{-1}$); and FIG. 25D: PLLA semi-crystalline (at 923 cm$^{-1}$).

FIG. 26A: 3D rendering image of PLA filament with 0.5 wt % INT-WS$_2$, FIG. 26B: volume distribution of the nanotubes and aggregates in the PLA matrix, FIG. 26C: particles positions distribution, FIG. 26D: particles positions distribution along the vertical axis. Note the large concentration of the particles at the filament center.

FIG. 27A: 3D rendering image of PLA filament with 0.5 wt % INT-WS$_2$, FIG. 27B: volume distribution of the nanotubes in the PLA matrix, FIG. 27C: particles positions distribution, FIG. 27D: particles positions distribution along the vertical axis. Note that post-printing the particles are much more evenly distributed.

FIG. 31A: a model of a human ear (1:1), printed of PLA/WS2-NT composite (with a pen to scale). Un-dyed, the model color is determined by the color of the WS2-NT. FIG. 31B: illustration of the printing process.

Figure 3A:
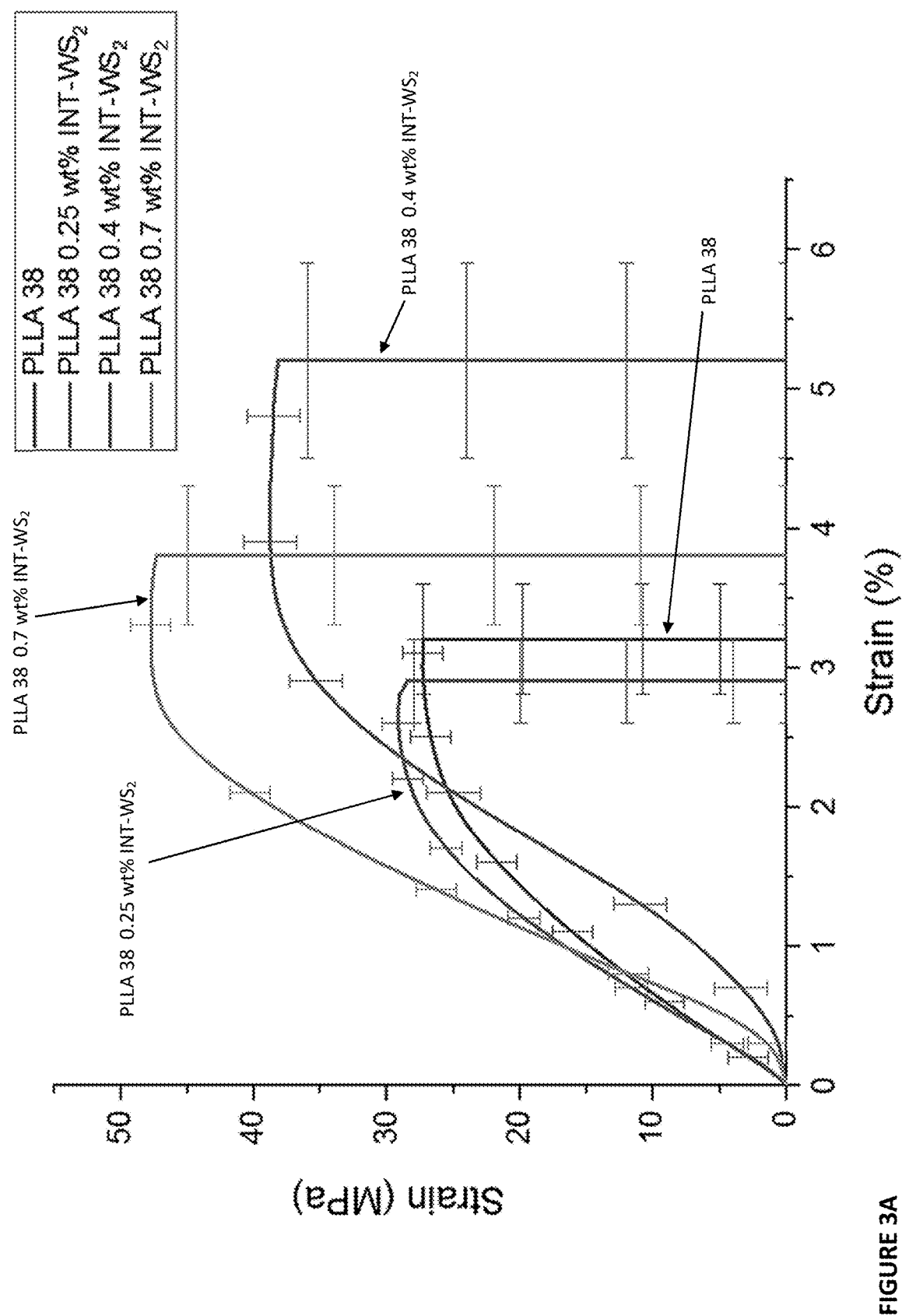
FIGS. 3A-3B depict stress-strain curves of PLLA films with different weight percentage of $INT-WS_2$ (with error bars).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Nanocomposites of this Invention

In one aspect, this invention provides a nanocomposite comprising a polymer and an anhydrous MX$_2$-based fullerene-like nanoparticles or nanotubes; wherein the polymer is selected from poly(lactic acid), poly (lactic-co-glycolic acid) or a combination thereof; M is Mo, W, Ta or Nb; and X is S, Se or Te.

In one embodiment, this invention provides a nanocomposite comprising a polymer and an anhydrous MX$_2$-based fullerene-like nanoparticles or nanotubes; wherein said polymer is selected from poly(lactic acid), poly (lactic-co-glycolic acid) or a combination thereof; M is Mo, W, Ta or Nb; and X is S, Se or Te; wherein the weight percentage of the MX$_2$-based fullerene-like nanoparticles or nanotubes from the total weight of said nanocomposite is between 0.25% and 3% and the composite has at least one of the following properties: modulus between 1.6-4 GPa; toughness (area below the stress-strain curve) between 1.1-40 MPa/%; static friction coefficient, $\mu_s$, between 0.055-0.08; kinetic friction coefficient, $\mu_s$, between 0.02-0.05; yield strength: between 15-75 MPa; and friction force reduced by between 10-99% compared to the polymer alone.

In one aspect, this invention provides a nanocomposite comprising a polymer and an anhydrous MX$_2$-based fullerene-like nanoparticles or nanotubes; wherein said polymer is selected from poly(lactic acid), poly (lactic-co-glycolic acid) or a combination thereof; M is Mo, W, Ta or Nb; and X is S, Se or Te; wherein the weight percentage of the MX$_2$-based fullerene-like nanoparticles or nanotubes from total the weight of said nanocomposite is between 0.25% and 3% and the composite has at least one of the following properties: modulus between 1.6-4 GPa; toughness (area below the stress-strain curve) between 1.1-40 MPa/%; static friction coefficient, $\mu_s$, between 0.055-0.08; kinetic friction coefficient, $\mu_s$, between 0.02-0.05; yield strength: between 15-75 MPa; and friction force reduced by between 10-99% compared to the polymer alone; In another embodiment, the polymer is dried during the process for the preparation of the nanocomposite.

In one embodiment this invention provides a nanocomposite which is prepared via the methods described hereinbelow.

In some embodiments a "composite" (or a "composite material") is herein defined as a material comprising two or more constituent materials with significantly different physical and/or chemical properties that, when combined, produce a material with different, altered, modified, or enhanced characteristics compared to the individual components. Between the constituents there are intermolecular forces such as van der Waals forces, hydrogen bonds, π-π interactions, hydrophobic forces and the like (excluding covalent interactions). In some embodiments, a "nanocomposite" as used herein is defined as a composite as defined hereinabove, where at least one of the constituent materials has one, two or three dimensions of less than 100 nanometers (nm); and/or where chemical structures (e.g. atomic layer) within the nanocomposite have nano-scale (<100 nm) repeat distance(s) in-between them.

Methods of Preparation

In one aspect, this invention provides a method for the preparation of a nanocomposite, wherein the nanocomposite comprises an anhydrous $MX_2$-based fullerene-like nanoparticles or nanotubes and a polymer selected from poly(lactic acid), poly (lactic-co-glycolic acid) or a combination thereof; wherein M is Mo, W, Ta or Nb; and X is S, Se or Te.; wherein the method comprises:
  dissolving the polymer in a first solvent;
  dissolving the anhydrous $MX_2$-based fullerene-like nanoparticles or nanotubes in a second solvent;
  mixing together both of the solutions;
  solvent casting the mixed solution; and
  drying the mixed solution to obtain the nanocomposite.

In another embodiment, the polymer is dried prior to its dissolution step. In another embodiment, the mixed solution is dried to form a film followed by an annealing step.

In one embodiment, this invention provides a method for the preparation of a nanocomposite, wherein the nanocomposite comprises an anhydrous $MX_2$-based fullerene-like nanoparticles or nanotubes and a polymer selected from poly(lactic acid), poly (lactic-co-glycolic acid) or a combination thereof; wherein M is Mo, W, Ta or Nb; and X is S, Se or Te; wherein the method comprises:
  dissolving the polymer in a first solvent;
  dissolving the anhydrous $MX_2$-based fullerene-like nanoparticles or nanotubes in a second solvent;
  mixing together both of the solutions;
  solvent casting the mixed solution;
  drying said mixed solution to form a film; and
  annealing said film to afford the nanocomposite.

In another embodiment, the polymer is dried prior to its dissolving step.

Without being bound by any mechanism or theory, poly (lactic acid) is hydrophilic, while the $INT\text{-}WS_2$ are hydrophobic and this polarity difference entails that the interfacial interaction between the surfaces of the two phases cannot be easily tuned. Accordingly, in some embodiments a surface modifying agent is added to the anhydrous $MX_2$-based fullerene-like nanoparticles or nanotubes in order to provide better compatibilization of the different surfaces of the polymer and the nanoparticles or the nanotubes.

In one embodiment, the method for the preparation of a nanocomposite of this invention comprises:
  dissolving a polymer in a first solvent, wherein the polymer is selected from poly(lactic acid), poly (lactic-co-glycolic acid);
  treating an anhydrous $MX_2$-based fullerene-like nanoparticles or nanotubes with a surface-modifying agent, wherein M is Mo, W, Ta or Nb; and X is S, Se or Te;
  dissolving the surface-treated $MX_2$-based fullerene-like nanoparticles or nanotubes in a second solvent;
  mixing together both of the solutions;
  solvent casting the mixed solution; and
  drying the mixed solution to obtain the nanocomposite.

In another embodiment, the polymer is dried prior to its dissolution step. In another embodiment, the mixed solution is dried to form a film followed by an annealing step.

In another embodiment, the method for the preparation of a nanocomposite of this invention comprises:
  dissolving a polymer in a first solvent, wherein the polymer is selected from poly(lactic acid), poly (lactic-co-glycolic acid);
  treating the anhydrous $MX_2$-based fullerene-like nanoparticles or nanotubes with a surface-modifying agent, wherein M is Mo, W, Ta or Nb; and X is S, Se or Te;
  dissolving the surface-treated $MX_2$-based fullerene-like nanoparticles or nanotubes in a second solvent;
  mixing together both of the solutions;
  solvent casting the mixed solution;
  drying said mixed solution to form a film; and
  annealing said film to afford the nanocomposite.

In another embodiment, the polymer is dried prior to its dissolution step.

In one embodiment, the nanocomposite includes a surface-modifying agent. In another embodiment, the surface-modifying agent is any compound, small molecule or polymer that can modify the surface of nanoparticles or nanotubes via chemical or physical interaction. In another, non-limiting examples of surface-modifying agent consist of the following: N-Methyl-2-pyrrolidone (NMP), polyethylenimine (PEI), polyethylene glycol (PEG) and cetyltrimethylammonium bromide (CTAB). Each possibility represents a separate embodiment of this invention.

In some embodiments, the first or second solvent used within the methods of this invention is any solvent known in the art. In another embodiment, non-limiting examples of first or second solvent are independently selected from dichloromethane (DCM), chloroform, diethyl ether, acetone, hexane, ethyl acetate, water, tetrahydrofuran (THF), acetonitrile, sulfolane, N,N-dimethylformamide (DMF), dimethylacetamide (DMA), dimethyl sulfoxide (DMSO), dioxane, ethanol, methanol and any combination thereof. Each possibility represents a separate embodiment of this invention. In another embodiment, the solvent is DCM or chloroform.

In some embodiments, dissolution of the polymer or the $MX_2$-based fullerene-like nanoparticles or nanotubes within the method of this invention is each independently performed via mechanical stirring, ultrasonic bath treatment or probe sonicator.

In some embodiments, mixing of the polymer and the $MX_2$-based fullerene-like nanoparticles or nanotubes solutions within the method of this invention is performed via mechanical stirring, ultrasonic bath treatment or extrusion.

Without being bound by any mechanism or theory, the drying within the methods of this invention should be performed carefully, to assure the formation of completely dried film/composite without "holes" of solvent (water or other solvents as described hereinabove) which was rapidly evaporated; it should be noted that such holes are "weak points" within the eventually formed film and thus impair physical performance (e.g. mechanical/tribological properties) of the film. Further, water residues on the nanoparticles/nanotubes surface may lead to their oxidation during printing/extrusion.

In one embodiment, long drying periods performed at low temperatures should be performed in the methods of this invention to provide the nanocomposite as described hereinabove, that have minimal number of weak points. In one other embodiment, any drying and/or annealing procedure which is capable of providing this nanocomposite are applied herein within the methods of this invention.

In some embodiments, the nanocomposite of this invention comprises inter-alia an anhydrous $MX_2$—based fullerene-like nanoparticles or nanotubes wherein M is Mo, W, Ta or Nb; and X is S, Se or Te.

In some embodiments, "anhydrous nanoparticles/nanotubes" (e.g. $MX_2$-based fullerene-like nanoparticles or $MX_2$ nanotubes) within the meaning of this invention are herein defined as nanoparticles/nanotubes which were dried/annealed in order to reduce the water amount (mole %) within the material. In one embodiment, the water amount is reduced by 15-100% (mole %) compared to the initial, non-treated amount. In another embodiment, the amount is reduced by 20-100% (mole %). In another embodiment, the amount is reduced by 15-20% (mole %). In another embodiment, the amount is reduced by 20-30% (mole %). In another embodiment, the amount is reduced by 30-40% (mole %). In another embodiment, the amount is reduced by 40-50% (mole %). In another embodiment, the amount is reduced by 50-60% (mole %). In another embodiment, the amount is reduced by 60-70% (mole %). In another embodiment, the amount is reduced by 70-80% (mole %). In another embodiment, the amount is reduced by 80-90% (mole %). In another embodiment, the amount is reduced by 90-100% (mole %). In another embodiment, the amount is reduced by 80-100% (mole %). In another embodiment, the amount is reduced by 20-60% (mole %). In another embodiment, the amount is reduced by 20-40% (mole %). In another embodiment, the amount is reduced by 60-80% (mole %). In another embodiment, the amount is reduced by 15-50% (mole %). In another embodiment, the amount is reduced by 50-70% (mole %). In another embodiment, the amount is reduced by 50-90% (mole %). In another embodiment, the amount is reduced by 50-100% (mole %).

In one embodiment, the drying/annealing process which provides anhydrous nanoparticles/nanotubes comprises heating and/or vacuum annealing at a temperature of between 60-200° C. for 0.5-3 hours. In another embodiment, the heating and/or vacuum annealing is performed at a temperature between 120° to 170° C., for about 1-2 hours. More specifically at a temperature of 150° C. for about 1.5 hours. In another embodiment, the drying/annealing process which provides anhydrous nanoparticles/nanotubes comprises dispersing the nanoparticles/nanotubes in a solvent (typically ethanol) and vacuum annealing of the solution at a temperature between 120° to 170° C., for about 1-2 hours, wherein the dispersing/vacuum annealing steps are performed in any order. More specifically at a temperature of 150° C. for about 1.5 hours. In another embodiment, the drying/annealing process which provides anhydrous nanoparticles/nanotubes further comprises heating and/or vacuum annealing at temperature of between 30-70° C. for overnight (8-20 hours). More specifically at a temperature of 50° C. In another embodiment, the heating and/or vacuum annealing at a temperature between 30 to 70° C. for overnight follows heating and/or vacuum annealing of the nanoparticles/nanotubes at a temperature between 60-200° C. for 0.5-3 hours. In another embodiment, the drying/annealing process which provides anhydrous nanoparticles/nanotubes comprises an HF (hydrofluoric acid) treatment (in addition to or instead any one of the above embodiments). In another embodiment, the HF treatment removes water by reacting with the nanoparticles/nanotubes. In another embodiment, various solutions and forms of HF can be used, e.g. $HF:H_2O$ in ratios of between 1:1-1:10 (v/v). In another embodiment, the ratio is between 1:1-1:2. In another embodiment, the ratio is between 1:2-1:3 In another embodiment, the ratio is between 1:3-1:4 In another embodiment, the ratio is between 1:4-1:5 In another embodiment, the ratio is between 1:5-1:6 In another embodiment, the ratio is between 1:6-1:7. In another embodiment, the ratio is between 1:7-1:8 In another embodiment, the ratio is between 1:8-1:9 In another embodiment, the ratio is between 1:9-1:10. Each possibility represents a separate embodiment of this invention.

In one embodiment, the method for the preparation of the nanocomposite comprises inter alia provision of anhydrous nanoparticles/nanotubes (via drying/annealing of nanoparticles/nanotubes as described hereinabove); and drying the mixed solution. In one embodiment, the method for the preparation of the nanocomposite comprises inter alia provision of anhydrous nanoparticles/nanotubes (via drying/annealing of nanoparticles/nanotubes as described hereinabove); drying the polymer; and drying the mixed solution. In another embodiment, "drying" within the context of this invention further comprises annealing. In another embodiment, drying is followed by annealing or annealing is followed by drying. In another embodiment, the drying and/or annealing is performed via one or more of the following:

drying in chemical hood ("fume hood") by flow thereof;
subjecting a solution of the nanoparticles/nanotubes and/or of the polymer to vacuum within fume hood vacuum system (e.g. "Schlenk" apparatus);
vacuum oven; or
hot extrusion.

In another embodiment, the methods of this invention for the preparation of a nanocomposite comprise inter-alia vacuum annealing of the anhydrous nanoparticles/nanotubes and the polymer (separately) at a temperature between 30 to 70° C. for overnight (about 8-20 hours) and extrusion. More specifically at a temperature of 50° C. In another embodiment, the extrusion is done once for the polymer alone and then twice for the polymer-nanoparticle/nanotubes mixture. Each possibility represents a separate embodiment of this invention.

In some embodiments, the drying of each of the $MX_2$—based fullerene-like nanoparticles or nanotubes (e.g. to provide anhydrous nanoparticle/nanotubes) and/or the polymer and/or the mixed solution used in the preparation of the nanocomposites is performed between 1 hour to 14 days. In another embodiment, between 5 minutes to 10 days. In another embodiment, between 5 minutes and 0.5 hour. In another embodiment, between 0.5 to 1 hour. In another embodiment, between 1 to 2 hours. In another embodiment, between 2 to 5 hours. In another embodiment, between 5 to 10 hours. In another embodiment, between 10 to 24 hours. In another embodiment, between 24 to 48 hours. In another embodiment, between 48 hours to 7 days. In another embodiment, between 7-10 days. In another embodiment, between 10-14 days. In another embodiment, the drying is performed for 1 hour, 1.5 hour, 6 hours, 48 hours or 7 days. Each possibility represents a separate embodiment of this invention.

In some embodiments, the drying of each of the $MX_2$—based fullerene-like nanoparticles or nanotubes (e.g. to provide anhydrous nanoparticle/nanotubes) and/or the polymer and/or the mixed solution used in the preparation of the nanocomposites is performed at between 30 to 160° C. In another embodiment, between 20 to 150° C. In another embodiment, between 30-40° C. In another embodiment, between 40-50° C. In another embodiment, between 50-60° C. In another embodiment, between 60-70° C. In another embodiment, between 70-80° C. In another embodiment, between 80-90° C. In another embodiment, between 90-100° C. In another embodiment, between 100-110° C. In another embodiment, between 110-120° C. In another embodiment, between 120-130° C. In another embodiment, between 130-140° C. In another embodiment, between 140-150° C. In another embodiment, between 150-160° C. In another embodiment, the drying is performed at 30, 40, 120 or 150° C. Each possibility represents a separate embodiment of this invention.

In some embodiments, annealing step within the methods of this invention is performed for any period of time sufficient to provide the nanocomposites. In another embodiment, the MX$_2$—based fullerene-like nanoparticles or nanotubes is annealed following a drying step or dried following an annealing step (e.g. in order to provide anhydrous nanoparticle/nanotubes). In another embodiment, the polymer is annealed following the drying step or dried following an annealing step. In another embodiment, the mixed solution is annealed following the drying or dried following an annealing step. In another embodiment, the mixed solution is annealed without the formation of a film by prior drying step of the mixed solution. In another embodiment, annealing is performed between 1 hour to 14 days. In another embodiment, annealing is performed between 5 minutes to 10 days. In another embodiment, it is performed between 5 minutes and 0.5 hour. In another embodiment, it is performed between 0.5 to 1 hour. In another embodiment, it is performed between 1 to 2 hours. In another embodiment, it is performed between 2 to 5 hours. In another embodiment, it is performed between 5 to 10 hours. In another embodiment, it is performed between 10 to 24 hours. In another embodiment, it is performed between 24 to 48 hours. In another embodiment, it is performed between 48 hours to 7 days. In another embodiment, it is performed between 7-10 days. In another embodiment, it is performed between 10-14 days. In another embodiment, it is performed for 1 hour, 1.5 hour, 6 hours, 48 hours or 7 days. Each possibility represents a separate embodiment of this invention.

In some embodiments, annealing within the methods of this invention is performed at any temperature sufficient to provide the nanocomposites. In another embodiment, the MX$_2$—based fullerene-like nanoparticles or nanotubes is annealed following a drying step (e.g. in order to provide anhydrous nanoparticle/nanotubes). In another embodiment, the polymer is annealed following the drying step. In another embodiment, the mixed solution is annealed following the drying. In another embodiment, the mixed solution is annealed without the formation of a film by prior drying step of the mixed solution. In another embodiment, the annealing is performed at between 30° C. to 160° C. In another embodiment, the annealing is performed at between 20° C. to 150° C. In another embodiment, the annealing is performed at between 30° C.-40° C. In another embodiment, the annealing is performed at between 40° C.-50° C. In another embodiment, the annealing is performed at between 50° C.-60° C. In another embodiment, the annealing is performed at between 60° C.-70° C. In another embodiment, the annealing is performed at between 70° C.-80° C. In another embodiment, the annealing is performed at between 80° C.-90° C. In another embodiment, the vacuum annealing is performed at between 90° C.-100° C. In another embodiment, the annealing is performed at between 100° C.-110° C. In another embodiment, the annealing is performed at between 110° C.-120° C. In another embodiment, the annealing is performed at between 120° C.-130° C. In another embodiment, the annealing is performed at between 130° C.-140° C. In another embodiment, the annealing is performed at between 140° C.-150° C. In another embodiment, the annealing is performed at between 150° C.-160° C. In another embodiment, the annealing is performed at 30° C., 40° C., 120° C. or 150° C. Each possibility represents a separate embodiment of this invention.

In some embodiments, any possible combination of temperature and time duration is applicable within drying and/or annealing of the methods of this invention, where specific temperatures and time durations are disclosed hereinabove. In one embodiment, drying and/or annealing is performed at a temperature of between 60-200° C. for 0.5-3 hours, at 120° to 170° C. for about 1-2 hours, at 150° C. for about 1.5 hours, 30-70° C. (more specifically at 50° C.) for overnight (8-20 hours), at 120° C. for 1 hour, at 120° C. for 6 hours, at 40° C. for 48 hours; or at 30° C. for 7 days. Each possibility represents a separate embodiment of this invention In some embodiments, the annealing is performed under vacuum for 1 hour at 120° C.; for 6 hours at 120° C.; for 48 hours at 40° C.; or for 7 days at 30° C. Each possibility represents a separate embodiment of this invention. In one embodiment, the annealing of the film should be performed carefully at low temperatures and for long time as described hereinabove, in order to arrive at the nanocomposite films of this invention. Without being bound by any mechanism or theory, it is contemplated that annealing above solvent's boiling point and polymer's glass transition temperature (i.e. annealing at too high temperature) causes solvent agitation in the polymer and prevent slow evaporation, leaving voids and disorder in the polymer film, which give rise to reduced, impaired physical performance (e.g. mechanical/tribological properties) of the formed annealed film.

In some embodiments, the polymer of the nanocomposites and/or methods of preparation of this invention is poly(lactic acid), poly (lactic-co-glycolic acid) or a combination thereof. In one embodiment, the polymer is poly (lactic acid). In another embodiment, the polymer is poly (L-lactic acid) (PLLA), poly(D-lactic acid) (PDLA) or poly (DL-lactic acid) (PDLLA). In one embodiment, the polymer is poly(lactic-co-glycolic acid). In another embodiment, the polymer is poly(L-lactic-co-glycolic acid), poly(D-lactic-co-glycolic acid) or poly(DL-lactic-co-glycolic acid). In another embodiment, the poly(lactic acid) has an inherent viscosity of between 0.2-6.5 dL/g. In another embodiment, the viscosity is between 0.2-0.5 dL/g. In another embodiment, the viscosity is between 0.2-0.5 dL/g. In another embodiment, the viscosity is between 0.5-1 dL/g. In another embodiment, the viscosity is between 1-2 dL/g. In another embodiment, the viscosity is between 2-4 dL/g. In another embodiment, the viscosity is between 4-6.5 dL/g. In another embodiment, the viscosity is 2.4 or 3.8 dL/g. Each possibility represents a separate embodiment of this invention.

In some embodiments, "M" of MX$_2$-based fullerene-like nanoparticles or nanotubes of the nanocomposites and/or methods of preparation of this invention is selected from the group consisting of: Mo, W, Re, Ti, Zr, Hf, Nb, Ta, Pt, Ru, Rh, In, Ga, and alloys thereof. In another embodiment, "M" is selected from the group consisting of Mo, W, Ta or Nb. In some embodiments, M is doped with a dopant (with concentration of below 1%, compared to M) selected from the group consisting of: Si, Nb, Ta, W, Mo, Sc, Y, La, Hf, Ir, Mn, Ru, Re, Os, V, Au, Rh, Pd, Cr, Co, Fe and Ni. In some embodiments, X of MX2 is a chalcogenide selected from S, Se and Te. Each possibility represents a separate embodiment of this invention.

In some embodiments, MX$_2$-based fullerene-like nanoparticles or nanotubes of the nanocomposites and/or methods of preparation of this invention are WS$_2$ or MoS$_2$.

In some embodiments, MX$_2$-based nanotubes of the nanocomposites and/or methods of preparation of this invention are single- or multi-walled nanotubes. In another embodiment, MX$_2$-based nanotubes are WS$_2$ nanotubes.

In some embodiments, the weight percentage of the MX$_2$-based fullerene-like nanoparticles or nanotubes of the nanocomposites and/or methods of preparation of this invention from the total weight of the nanocomposite is between 0.25 and 3. In another embodiment, the weight percentage is between 0.25 and 0.5. In another embodiment, the weight percentage is between 0.5 and 1. In another embodiment, the weight percentage is between 1 and 1.5. In another embodiment, the weight percentage is between 1.5 and 2. In another embodiment, the weight percentage is between 2 and 2.5. In another embodiment, the weight percentage is between 2.5 and 3. In another embodiment, the weight percentage is 0.25; 0.4; 0.5; 0.7; 0.8; 1; or 3. Each possibility represents a separate embodiment of this invention.

In some embodiments, the nanocomposites provided by this invention and/or prepared via methods thereof have modulus of between 1.6-4 GPa. In another embodiment, the modulus is between 1.6-2 GPa. In another embodiment, the modulus is between 2-2.5 GPa. In another embodiment, the modulus is between 2.5-3 GPa. In another embodiment, the modulus is between 3-3.5 GPa. In another embodiment, the modulus is between 3.5-4 GPa. Each possibility represents a separate embodiment of this invention.

In some embodiments, the nanocomposites provided by this invention and/or prepared via methods thereof have yield strength of between 15-75 MPa. In another embodiment, the yield strength is of between 15-20 MPa. In another embodiment, the yield strength is of between 20-25 MPa. In another embodiment, the yield strength is of between 25-30 MPa. In another embodiment, the yield strength is of between 30-35 MPa. In another embodiment, the yield strength is of between 35-40 MPa. In another embodiment, the yield strength is of between 40-45 MPa. In another embodiment, the yield strength is of between 45-50 MPa. In another embodiment, the yield strength is of between 50-55 MPa. In another embodiment, the yield strength is of between 55-60 MPa. In another embodiment, the yield strength is of between 60-65 MPa. In another embodiment, the yield strength is of between 65-70 MPa. In another embodiment, the yield strength is of between 70-75 MPa. Each possibility represents a separate embodiment of this invention.

In some embodiments, the nanocomposites provided by this invention and/or prepared via methods thereof have toughness (area below the stress-strain curve) of between 1.1-40 (MPa/%). In another embodiment, the toughness is between 1.1-2 (MPa/%). In another embodiment, the toughness is between 2-5 (MPa/%). In another embodiment, the toughness is between 5-10 (MPa/%). In another embodiment, the toughness is between 10-20 (MPa/%). In another embodiment, the toughness is between 20-30 (MPa/%). In another embodiment, the toughness is between 30-40 (MPa/%). Each possibility represents a separate embodiment of this invention.

In some embodiments, the nanocomposites provided by this invention and/or prepared via methods thereof have static friction coefficient, $\mu_s$, of between 0.055-0.08, whereas pure poly (lactic acid) has static friction coefficient values of above 0.1 (e.g. in example 8 the values are around 0.2). In another embodiment, the static friction coefficient is between 0.055-0.06. In another embodiment, the static friction coefficient is between 0.06-0.065. In another embodiment, the static friction coefficient is between 0.065-0.07. In another embodiment, the static friction coefficient is between 0.07-0.075. In another embodiment, the static friction coefficient is between 0.075-0.08. Each possibility represents a separate embodiment of this invention.

In some embodiments, the nanocomposites provided by this invention and/or prepared via methods thereof have kinetic friction coefficient, $\mu_k$, of between 0.02-0.05, whereas pure poly (lactic acid) has kinetic friction coefficient values of above 0.1 (e.g. in example 8 the values are around 0.2). In another embodiment, the kinetic friction coefficient is between 0.02-0.03. In another embodiment, the kinetic friction coefficient is between 0.03-0.04. In another embodiment, the kinetic friction coefficient is between 0.04-0.05. Each possibility represents a separate embodiment of this invention.

In some embodiments, the nanocomposites provided by this invention and/or prepared via methods thereof have significantly reduced friction force compared to that of the polymer alone. In one embodiment, this significant reduction is evident in both dry and wet (e.g. in water) conditions. In one embodiment, the friction force reduction is between 10-99%. In another embodiment, the friction force reduction is between 10-20%. In another embodiment, the friction force reduction is between 20-30%. In another embodiment, the friction force reduction is between 30-40%. In another embodiment, the friction force reduction is between 40-50%. In another embodiment, the friction force reduction is between 50-60%. In another embodiment, the friction force reduction is between 60-70%. In another embodiment, the friction force reduction is between 70-80%. In another embodiment, the friction force reduction is between 80-90%. In another embodiment, the friction force reduction is between 90-99%. Each possibility represents a separate embodiment of this invention.

In some embodiments, the nanocomposites provided by this invention and/or prepared via methods thereof show shear thinning viscosity behavior which is similar or identical to the behavior of the polymer of the nanocomposite. In another embodiment, the shear thinning viscosity of the nanocomposites is of the non-Newtonian type. Moreover, and without being bound by any mechanism or theory—the nanotubes within the nanocomposites exhibit little tendency to agglomerate and their influence on the rheological properties of the nanocomposites (e.g. viscosity and moduli) is found to be very minor, if any. In this regard, it should be noted that in some cases, the nanotubes induce higher crystallinity of the polymer within the matrix, due likely to their role as nucleation centers. These characteristics have important ramifications on the dispersion of the nanotubes in the polymer matrix and the manufacturing processes of such nanocomposites.

In some embodiments, the nanocomposites provided by this invention and/or prepared via methods thereof show high stability over prolonged times. In one embodiment, the stability is chemical and/or mechanical. In one embodiment, the nanocomposites are stable for between 0.5 to 5 years. In another embodiment, the nanocomposites are stable for between 0.5 to 1 year. In another embodiment, the nanocomposites are stable for between 1 to 2 years. In another embodiment, the nanocomposites are stable for between 2 to 5 years. In another embodiment, the nanocomposites are stable for at least 0.5 year. In another embodiment, the nanocomposites are stable for at least 1 year. In another embodiment, the nanocomposites are stable for at least 2 years. Each possibility represents a separate embodiment of this invention.

In some embodiments, the nanocomposites provided by this invention and/or prepared via methods thereof do not show any change in the composition and/or crystallinity due to stretching, i.e. they show high stability towards stretching.

In some embodiments, the nanocomposites provided by this invention and/or prepared via methods thereof have volume resistivity of between 5E+05-3E+10 Ωcm. In another embodiment, the volume resistivity is between 5E+05-5E+06 Ωcm. In another embodiment, the volume resistivity is between 5E+06-5E+07 2 cm. In another embodiment, the volume resistivity is between 5E+07-5E+08 Ωcm. In another embodiment, the volume resistivity is between 5E+08-5E+09 Ωcm. In another embodiment, the volume resistivity is between 5E+09-3E+010 Ωcm. In another embodiment, the volume resistivity is 7.32E±09±2.49E±08, 3.99E±09±5.84E±06, 1.97E±09±7.56E±06, 1.15E±08±1.72E±05, 1.28E±10±2.38E±08, 2.34E±10±8.79E±08, 6.53E±09±1.76E±08, 9.79E±07±4.67E±05, 2.64E±07±4.21E±05, 8.36E±06±3.61E±04, 9.69E±05±3.52E±04, 2.03E±07±1.88E±05, 9.77E±06±2.58E±05 or 2.51E±06±2.21E±04 2 cm. In one embodiment, the volume resistivity can be measured by any method as known in the art. In another embodiment, the volume resistivity is measured by the two or four probe method. Each possibility represents a separate embodiment of this invention.

Uses

In one aspect, this invention provides uses of the nanocomposites as described hereinabove. In one embodiment, this invention provides a medical device or product comprising the nanocomposites. In one embodiment, the nanocomposite used in a medical device or product comprises a polymer and anhydrous $MX_2$-based fullerene-like nanoparticles or nanotubes, as described hereinabove. In one embodiment, the nanocomposites are used in various medical aspects, such as: orthopedics, ophthalmology, cardiology, plastic surgeries and gynecology. In another embodiment, the medical device or product is selected from a medical artificial replacement of tissues product such as bone, bone cements and joints; patch on the skull; surgical mesh; breast implants; lenses; blood vessels; artificial heart valves; artificial skin; implants; intra uterine devices; shunts; catheters; stents; coating for subcutaneous implants such as: insulin pumps, contraceptives, pacemakers. tubing and cannulas used for intra venous infusion, tubing and cannulas used for dialysis, surgical drainage tubing, catheters, endotracheal tubes, sutures, catheters of all kinds that are inserted temporarily or permanently in blood vessels as well as the urinary system, shunt, surgical gloves, tips for ear examination, statoscope ends; and other elements used by the medical personnel such as: tooth brushes, tooth pick, dental floss, interdental and tongue brushes and plasticware for medical and research laboratories. In another embodiment, the catheters are of all kinds that are inserted temporarily or permanently in blood vessels as well as the urinary system. In another embodiment, shunts are used in brain and/or neurosurgical applications. In another embodiments, stents are urethral. Each possibility represents a separate embodiment of this invention In one embodiment, the nanocomposite of this invention is used for 3D printing. In one embodiment, this invention provides the nanocomposites for use as filaments for 3D printing. In one embodiment filaments for 3D printing comprise the nanocomposite of this invention. In one embodiment, the nanocomposite used in 3D printing and filaments thereof comprises a polymer and anhydrous $MX_2$-based fullerene-like nanoparticles or nanotubes, as described hereinabove. In another embodiment, the filaments are prepared via extrusion process. In another embodiment, the extrusion is performed via single or twin screw.

In one embodiment, this invention provides a method of preparing filaments comprising nanocomposites of this invention, comprising:
  drying $MX_2$-based fullerene-like nanoparticles or nanotubes and a polymer, thereby providing anhydrous nanoparticles/nanotubes and a dried polymer;
  extruding and mixing the dried polymer with the anhydrous nanoparticles or nanotubes in the melt state,
    wherein the extrusion is hot extrusion, thereby providing extruded $MX_2$-polymer pellets, comprising the nanocomposite; and
  extruding the pellets, thereby providing filaments comprising the nanocomposites;
  wherein
  the polymer is selected from poly(lactic acid), poly (lactic-co-glycolic acid) or a combination thereof;
  M is Mo, W, Ta or Nb; and
  X is S, Se or Te.

In another embodiment, drying of the nanoparticles or nanotubes comprises vacuum annealing at a temperature of 120° to 170° C., for 1-2 hours. More specifically at a temperature of 150° C. for about 1.5 hrs. In another embodiment, the drying of the nanoparticles or nanotubes further comprises heating at vacuum oven at 30-70° C. (e.g. 50° C.) for 8-20 hours. In another embodiment, drying of the polymer comprises heating at vacuum oven at 30-70° C. for 8-20 hours. In another embodiment, the extrusion steps can be repeated more than once, for example $MX_2$-polymer mixture extrusion can be repeated twice. Each possibility represents a separate embodiment of this invention.

In other embodiments, this invention provides filaments for 3D printing comprising the nanocomposite of this invention. In another embodiment, the filament is processed by Fused Deposition Modeling (FDM) 3D-printer. In another embodiment, the addition of $MX_2$-based fullerene-like nanoparticles or nanotubes; to poly(lactic acid), poly (lactic-co-glycolic acid) or a combination thereof by extrusion mixing increases the elastic, modulus and yield strength. In another embodiment, the printing parameters do not require change compared to pure PLA. In another embodiment, the addition of $MX_2$-based fullerene-like nanoparticles or nanotubes as reinforcement specifically in 3D-printable polymers is advantageous, over more traditional nano-reinforcements such as graphene and carbon nanotubes.

The following examples are presented in order to more fully illustrate the preferred embodiments of the invention. They should in no way, however, be construed as limiting the broad scope of the invention.

EXAMPLES

Example 1

Preparation of Nanocomposites

The nanocomposite films were prepared by solvent-casting. Two kinds of PLLA with different viscosity values of 2.4 and 3.8 dL/g (also called PLLA 24 and PLLA 38) were dissolved in dichloromethane (DCM) (5 w/V %) by mechanical stirring and solvent-casting in Teflon plates. PLLA films with 0.5 wt % $WS_2$ nanotubes (INT-$WS_2$) were prepared by first fully dissolving the PLLA in most of the DCM by mechanical stirring; secondly, the nanotubes (initially dispersed in ethanol and then vacuum annealed for 1.5 h at 150° C.) were fully dispersed in the rest of the DCM by ultrasonic bath treatment (about 5 min) and finally the two solutions were mixed together by mechanical stirring before solvent-casting in Teflon plates. The Teflon plates were dried by either a vacuum or by simply placing them in a hood. Subsequently, the film annealed in 120, 40 and 30° C. for different times. The weight loss was monitored daily for some of the Teflon plates.

Example 2

Functionalization of Nanocomposites

Several surface-modifying agents were used to functionalize the nanotubes: cetyltrimethylammonium bromide (CTAB), N-Methyl-2-pyrrolidone (NMP), Polyethylenimine (PEI) and Polyethylene glycol (PEG).

N-Methyl-2-pyrrolidone (NMP)

INT-$WS_2$ powder (initially dispersed in ethanol and then vacuum annealed for 1.5 h at 150° C.) was sonicated for 30 min in a mixture of INT-$WS_2$: NMP: distilled water in a ratio of 2 mg: 1 ml: 2 ml. Subsequently the suspension was annealed for 6 h at 120° C. to dry the INT-$WS_2$: NMP, before mixing with PLLA 38—DCM solution. The films were then cast, dried and annealed as described above in Example 1.

Polyethylenimine (PEI)

INT-$WS_2$ (initially dispersed in ethanol and then vacuum annealed for 1.5 h at 150° C.) were added to PEI (2% in aqueous solution) and sonicated at room temperature. Subsequently, the suspension was centrifuged at 6000 rpm for 15 min and washed with distilled water. Finally, the suspension was dried at 50° C. for 24 h before mixing with PLLA 24-chloroform solution. The films were then cast, dried and annealed as described above in Example 1, but with chloroform instead of DCM.

Polyethylene glycol (PEG)

INT-$WS_2$ (initially dispersed in ethanol and then vacuum annealed for 1.5 h at 150° C.) solution in DCM (1 mg/mL) was mixed with PEG (1 mg/20 mg) at room temperature. Subsequently, the solution was treated in ultrasonic bath for 30 min followed by centrifugation at 6000 rpm for 5 min and washed with distilled water to eliminate the excess polymer. Obtained INT-$WS_2$—PEG was dried to remove DCM, before mixing with PLLA 24-DCM solution. The PLLA 24 films were prepared according to the description in Example 1.

Example 3

Characterization Techniques—General

High-Resolution Scanning Electron Microscopy (HRSEM)

SEM: The morphology and structure of PLLA/INT-$WS_2$ nanocomposite films were characterized by HRSEM (Zeiss Ultra 55) after breaking each sample in liquid nitrogen. In order to avoid the sample charging during the analysis, the imaging was done under relatively low accelerating voltage (1-2 kV) and low current, using secondary electrons (SE2) and backscattering electron (BSE) detectors.

Mechanical Characterization

Mechanical characterization of the films was performed by tensile testing, using Instron equipped with a 5 kN load cell at room temperature and a stretching speed of 1 mm/min. The samples were cut into strips, 5 mm wide and 5 cm long, while the internal length of the framework was 3 cm. Sample thickness was measured in HRSEM by measuring the cross-section of each sample along the sample before the test X-Ray Tomographic Microscopy (Micro-XCT)

Benefiting from the large difference in atomic number of the matrix and the filler, the 3D distribution of the nanotubes in the PLLA matrix could be imaged with a Micro XCT. A relatively low source voltage (40 kV) and current (200 A) were used to detect the nanotubes. Image processing and analysis were done with the Avizo software. The voxel size was 0.3 microns. The images were corrected for beam hardening.

X-Ray Diffraction (XRD)

X-ray diffraction was performed on PLLA films to measure the degree of crystallinity of each sample. The samples were scanned by X-ray powder diffraction (XRD) using TTRAX III (Rigaku, Tokyo, Japan) theta-theta diffractometer equipped with a rotating copper anode X-ray tube operating at 50 kV/200 mA. The samples were scanned in specular diffraction mode (0/2θ scans) from 5 to 60 degrees (2θ) with a step size of 0.02 degrees and a scan rate of 0.5 degrees per minute.

Coefficient of Friction

The friction forces were measured by using Instron 5965, with a coefficient of friction frictional fixture (2810-005). The measurement of the static and kinetic friction coefficient of films was carried out by ASTM D1894. The measurements were performed by recording the load of a moveable sled with weight of 1.15 kg (speed of 150 mm/min) across the horizontal table. The static friction coefficient was derived from the first maximum peak (force) on the load curve and the kinetic friction coefficient was obtained by averaging the force between two pre-defined points. The coefficient of friction is defined as the recorded force divided by the mass of the sled (no extra load was applied). All the tests were performed at room temperature in air.

Three different measurements were carried out:

PLLA 24 film and PLLA 24 film with 0.5 wt % INT-$WS_2$ were run 20 times on the steel table (the first 16 times served for running-in). The results of the last 4 measurements are reported.

PLLA 24 film and PLLA 24+0.5 wt % INT-$WS_2$ film was rubbed 5 times on a SiC paper (120° grit) and then measured 3 times with the steel table.

PLLA 24 film and PLLA 24+0.5 wt % INT-$WS_2$ film was rubbed 5 times on SiC paper (150 grit) and then measured 3 times with the steel table.

Friction Force

The friction force was measured using a modified mock-up model of the urethra-endoscope pair (Goldbart, O., et al. (2014). "Lubricating Medical Devices with Fullerene-Like Nanoparticles." *Tribology Letters* 55(1): 103-109) at room temperature and using vulcanizing (RTV) silicone rings. Stainless steel rod with cylindrical cross-section (8 mm dimeter) was fixed to the lead with two screws and attached to the load cell of the Instron. The lead was inserted into the RTV silicone ring in the model and the retraction force was measured while extracting the metallic lead from the ring at a speed of 50 mm/min. In every set of measurements, three different stainless-steel rods were used: clean rod; rod coated by dip coating in the polymer solution; and in polymer solution with 0.5 wt % INT-$WS_2$ as described in Example 1, to form a nanocomposite of this invention, coated on the rod. Different types of polymers were measured. They were: PLLA 24, PLLA 38, PLLA with a viscosity of 2.1 dL/g (RESOMER L210), PDLLA (viscosity of 0.55 dL/g, Lakeshore Biomaterials) and Poly(D, L-lactide-co-glycolide) (PDLGA 50/50) (viscosity of 0.4 dL/g, Lakeshore Biomaterials). The values of the polymer viscosities were provided by the supplier. The viscosity of the polymers was measured (by the supplier) in $CHCl_3$ at 25° C. or 30° C. No run-in procedure was undertaken in this case.

Rheological Characterization

Dynamic shear rheological characteristics of the PLLA polymer and PLLA reinforced with 0.5 wt % $INT\text{-}WS_2$ were determined by using a strain/stress controlled rheometer (Thermo-Haake MARS III, Karlsruhe, Germany) equipped with a Peltier heating system and a temperature-control unit (HAAKE Heat Exchanger A, Thermo Scientific, Karlsruhe, Germany). The measurements were carried out using a plate-plate configuration with a plate diameter of 20 mm and a gap of 0.05 mm. Sample was placed between the plate-plate geometry and the measurement was started after pre-heating to 185±0.1° C.

Before starting the frequency sweep tests, stress sweep test was applied at a range between 1-10,000 Pa to determine the linear viscoelastic regime (LVR) of sample. Then, the frequency sweep test was conducted for all samples using a dynamic oscillatory shear rheometer at a frequency range of 0.1-100 Hz at a constant shear stress (3000 Pa, in LVR) in the LVR and constant temperature (185±0.1° C.) to evaluate the complex viscosity, storage (G') and loss (G") moduli spectra for both PLLA compositions. Each measurement was replicated three times. The dynamic mechanical spectra parameters of G' (storage modulus) and G" (loss modulus) were calculated using the following equations (J. F. Steffe, *Rheological Methods in Food Process Engineering—James Freeman Steffe*. East Lansing, MI, 1996):

$$G' = G \times \cos \delta \quad (1)$$

$$G'' = G \times \sin \delta \quad (2)$$

Where $\delta$ is the phase lag between stress and strain and $G$ is the shear modulus.

The complex viscosity $\eta^*$ can be calculated as $$\eta^* = G^*/\omega \quad (3)$$

where $\omega$ is the angular frequency and the complex modulus is defined as $G^* = G' + iG''$ with $i = (-1)^{0.5}$.

Raman Spectroscopy

Raman spectra of the films were obtained with a Horiba-Jobin Yivon (Lille, France) LabRAM HR Evolution set-up using solid state laser with a wavelength of 532 nm. The instrument was equipped with an Olympus objective MPlan N 100×NA 0.9. The measurements were conducted using a 600 grooves/mm grating. Each spectrum was acquired for 20 s and the spectra were averaged 2 times, which enabled using low excitation power (about 1 mW) thereby preserving the sample integrity. The spectral ranges collected were from 70 to 3400 cm$^{-1}$. In addition, Raman mapping was performed on the cross section of PLLA film with 0.5 wt % $INT\text{-}WS_2$. An area of (5×5 µm$^2$) of the cross-section was scanned during these measurements.

Differential Scanning Calorimetry (DSC)

Differential scanning calorimetry (DSC) was performed with a TA Instruments DSC 250. Temperature and enthalpy calibrations were performed using indium. The weighted samples were about 5 mg. They were placed in an aluminum pan and measured against an empty pan as a reference. Measurements were carried out under 50 ml/min nitrogen flow rate according to the following protocol: First, heating from 30 to 200° C. and 3 min at 200° C. (in order to erase the thermal history). Then, cooling down to 30° C., and finally a 2$^{nd}$ heating until 200° C. All scans were performed at 10 C/min under 50 ml/min nitrogen flow rate. From the mid-point of the (heating scan) thermograms, the glass transition ($T_g$), cold crystallization ($T_{cc}$) and melting ($T_m$) temperatures were determined. The crystallization temperature ($T_g$) was determined from the cooling scan. The degree of crystallinity was calculated from the DSC curves in two ways:

$$X_c = \frac{(\Delta H_m - \Delta H_{cc})}{\Delta H_m^\circ} \times 100\% \quad (1)$$

for heating (E. W. Fischer, H. J. Sterzel, and G. Wegner, "Investigation of the structure of solution grown crystals of lactide copolymers by means of chemical reactions," 1973; F. Carrasco, P. Pagès, J. Gámez-Pérez, O. O. Santana, and M. L. Maspoch, "Processing of poly(lactic acid): Characterization of chemical structure, thermal stability and mechanical properties," *Polym. Degrad. Stab.*, vol. 95, no. 2, pp. 116-125, 2010.; C. Migliaresi, D. Cohn, A. De Lollis, and L. Fambri, "Dynamic mechanical and calorimetric analysis of compression-molded PLLA of different molecular weights: Effect of thermal treatments," *J. Appl. Polym. Sci.*, vol. 43, no. 1, pp. 83-95, 1991.; and H. Zhou, T. B. Green, and Y. L. Joo, "The thermal effects on electrospinning of polylactic acid melts," *Polymer (Guildf).*, vol. 47, no. 21, pp. 7497-7505, October 2006.); and $$(1-\lambda) = \frac{\Delta H_c}{\Delta H_m^\circ} \quad (2)$$

for cooling (M. Naffakh, C. Marco, and G. Ellis, "Development of novel melt-processable biopolymer nanocomposites based on poly (l-lactic acid) and $WS_2$ inorganic nanotubes," *CrystEngComm*, vol. 16, no. 23, pp. 5062-5072, 2014.; and M. Naffakh, C. Marco, and G. Ellis, "Inorganic WS2 nanotubes that improve the crystallization behavior of poly(3-hydroxybutyrate)," *CrystEngComm*, vol. 16, p. 1126, 2014).

$\Delta H_m$, $\Delta H_{cc}$ (heating) and $\Delta H_c$ (cooling) are the melting enthalpy, cold crystallization enthalpy and crystallization enthalpy (J/g), respectively; $\Delta Hm°$, is the heat of fusion for completely crystallized poly(lactic acid) (93 J/g).

Example 4

Sample Preparation Parameters

Drying Mode: Hood Vs Vacuum

The solvent (DCM) evaporated from the polymer films in a different way according to the drying method. FIGS. 1A-B show PLLA 38 film's cross-section prepared according to two different methods of drying. First, the polymer films were prepared by solvent casting. The PLLA 38 film prepared by drying in vacuum show large roughness and thickness variation of the film (FIG. 1A).

This non-uniformity can be attributed to the fast evaporation of the solvent, which created failing points along the film. PLLA 38 film (FIG. 1B) which was dried in the hood, on the other hand, exhibited much more homogeneous thickness due to the slow and uniform evaporation of the solvent along the film. Table 1 summarizes the mechanical properties of the PLLA 38 film. The PLLA 38 film dried in vacuum showed a low modulus and short elongation length. The poor mechanical behavior can be attributed to the large roughness of the film. PLLA 38 film dried in hood demonstrated high modulus and large elongation distance. The larger ductility compared to the vacuum-dried film is attributed to the more uniform thickness of the former kind of film.

TABLE 1

Mechanical properties of PLLA 38 films

| Samples | Modulus (GPa) | Yield strength (MPa) | Strain at Break (%) | Toughness (MPa/%) |
|---|---|---|---|---|
| PLLA 38 film dried in vacuum | 1.75 ± 0.05 | 33.5 ± 0.6 | 4.0 ± 0.6 | 0.9 ± 0.2 |
| PLLA 38 film dried in a hood | 2.3 ± 0.2 | 52.8 ± 2.1 | 7.5 ± 2.3 | 2.3 ± 1.0 |

FIGS. 2A-D show the PLLA 24 film's cross-section prepared by the two different drying processes. The influence of INT-$WS_2$ (0.5 wt %) on the cross-section of the PLLA film is also shown. The two PLLA 24 films dried in vacuum (FIGS. 2A-B) are characterized by hills along the film which exhibit high surface roughness due to rapid evaporation of the solvent. The film with 0.5 wt % INT-$WS_2$, which was dried in vacuum (FIG. 2B), contain also holes, which impair its mechanical properties (Table 2) compared to the blank (FIG. 2A), i.e. lower modulus and short elongation. It is proposed that the addition of the nanotubes leads to an increase in the surface tension of the PLLA 24 blend. Therefore, the evaporated solvent is occluded in the film. These occlusions (holes) serve as weak points during the tensile test impairing the toughness of the film. The surface of the PLLA 24 films dried in the hood (FIGS. 2C-D) appear to be appreciably more uniform and smooth, due likely to the slow and uniform evaporation of the solvent from the film. Nonetheless, the film with 0.5 wt % INT-$WS_2$ (FIG. 2D) has a more homogeneous thickness compared to the blank (FIG. 2C) because the presence of the nanotubes increases the total evaporation rate by creating nucleation points and possibly also the higher surface tension of the blend with the tubes. The mechanical properties of PLLA 24 film with 0.5 wt % INT-$WS_2$ dried in the hood are higher by almost a factor of 2 compared to the PLLA 24 film dried in the hood (Table 2).

TABLE 2

Mechanical properties of PLLA 24 films

| Samples | Modulus (GPa) | Yield strength (MPa) | Strain at Break (%) | Toughness (MPa/%) |
|---|---|---|---|---|
| PLLA 24 film dried in vacuum | 1.6 ± 0.05 | 34.7 ± 1.5 | 5.0 ± 0.65 | 1.2 ± 0.3 |
| PLLA 24 film with 0.5 wt % INT-$WS_2$ dried in vacuum | 1.3 ± 0.1 | 25.0 ± 2.0 | 4.0 ± 0.5 | 0.6 ± 0.1 |
| PLLA 24 film dried in the hood | 1.2 ± 0.05 | 26.2 ± 0.7 | 3.7 ± 0.1 | 0.6 ± 0.05 |
| PLLA 24 film with 0.5 wt % INT-$WS_2$ Dried in the hood | 2.3 ± 0.05 | 54.4 ± 1.6 | 14.6 ± 3.4 | 5.3 ± 1.1 |

Annealing (Effect of Time and Temperature)

After the first step of drying the polymer's films, it was very important to anneal the films to remove completely all the volatile residues of the solvent. The annealing temperature depended on the polymer and solvent type. PLLA has a glass temperature between 60-65° C. and melting temperature varying between 170-200° C. DCM has a boiling temperature of 39.6° C. under ambient pressure, which is expected to decrease under vacuum. Table 3 shows the mechanical properties of a pure PLLA 38 film and that with nanotubes after vacuum annealing was performed at 120, 40 and 30° C. for 1, 6, 48 h and 7 days. Following the annealing at 120° C., which is above the glass transition temperature, the crystallinity of the film was improved. Consequently, substantially reduced elongation of the PLLA 38, i.e. reduced ductility of the annealed samples was observed with increased annealing time.

Annealing at 40° C. under vacuum, corresponds to conditions below the glass-transition temperature of PLLA 38, but above the boiling point of DCM (38° C.). Consequently, the mechanical properties showed improvement but not significant for both the blank PLLA 38 film and the PLLA 38 films with the nanotubes. Annealing in vacuum above the boiling point of DCM, caused solvent agitation in the polymer and prevented slow evaporation, leaving voids and disorder in the polymer film.

Figure 3B:
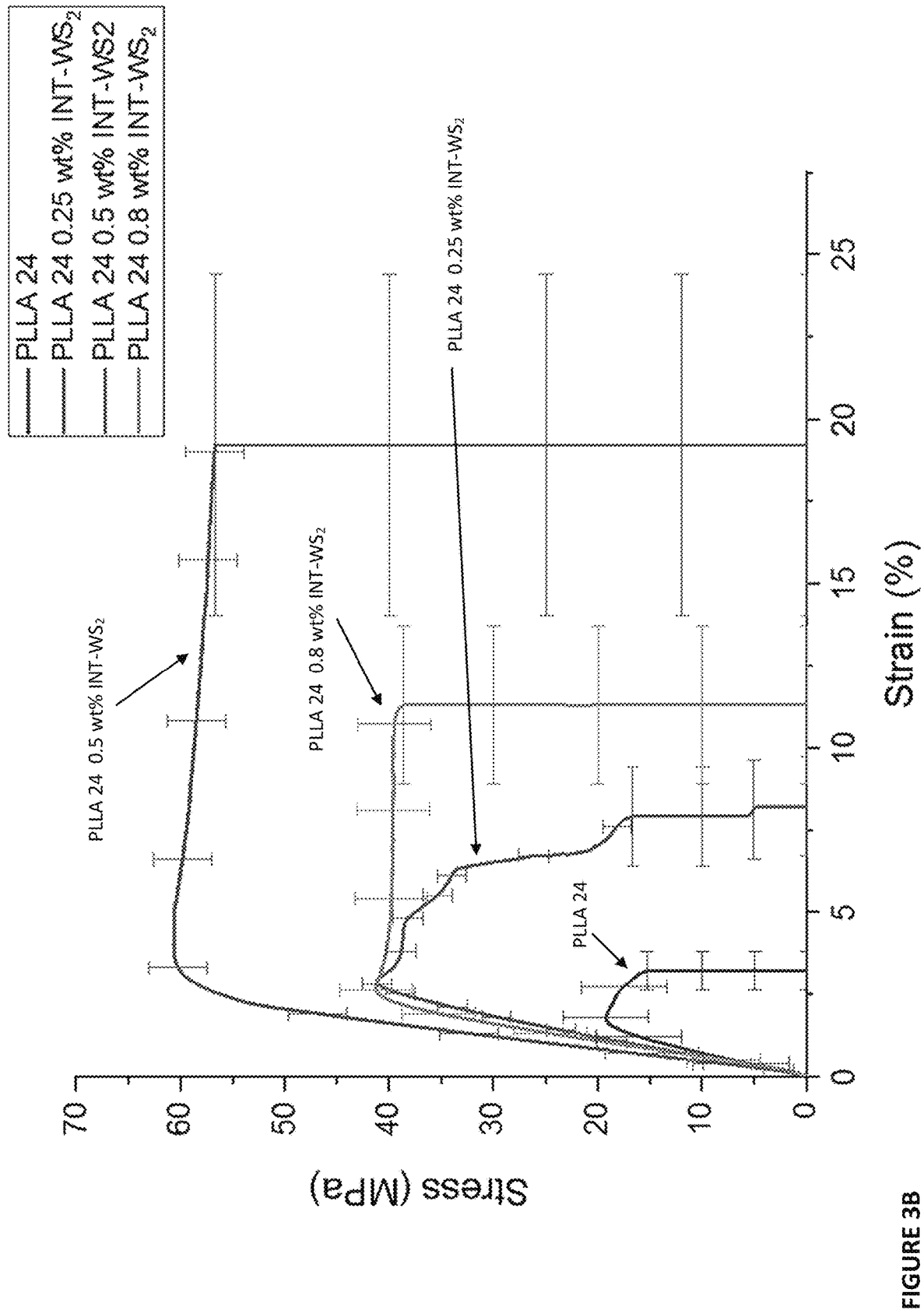
Figure 4:
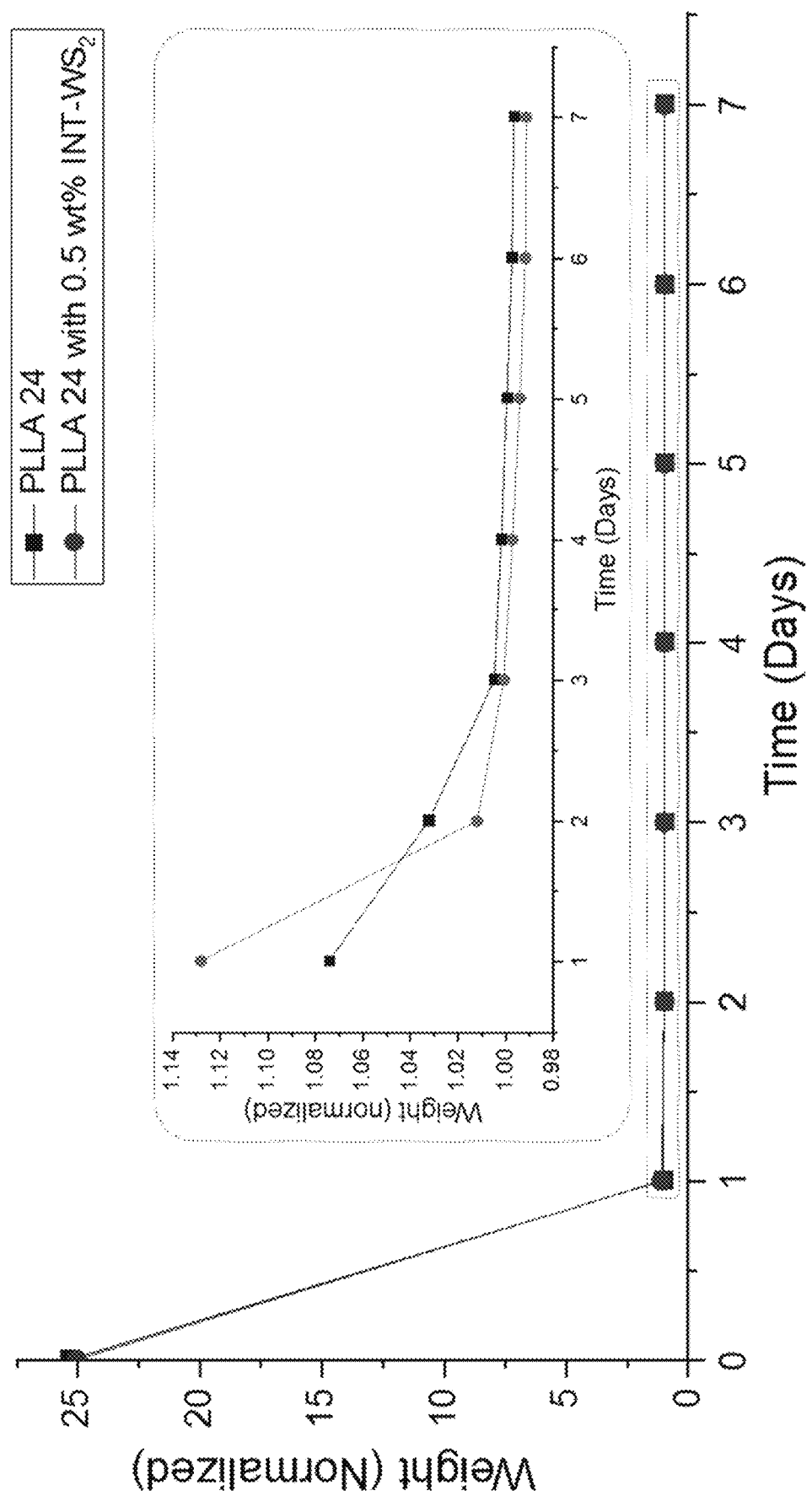
FIG. 4 depicts weight loss of the films annealed at 30° C. under vacuum for one week: squares denote PLLA 24; and circles denote PLLA 24 with 0.5% wt $INT-WS_2$. Inset graph shows a magnified region from day 1 to 7.

Table 3 and Table 4 show the mechanical properties of PLLA 38 and PLLA 24 respectively after vacuum annealing at 30° C. for 7 days, which is under the glass-transition temperature and boiling temp. of DCM. The results show improvement in the mechanical properties of the PLLA 38 as the concentrations of the nanotubes increase, and even larger improvements in the PLLA 24 film compared to the blank. On the other hand, the elongation and toughness (area under the stress-strain curve—see FIGS. 3A-B) showed the largest improvement around 0.5 wt % INT (the same as for carbon nanotubes). In addition, the modulus and the strength of PLLA 24 films exhibited the largest improvement around 0.5 wt % nanotubes, but the elongation and toughness increased as the concentration of nanotubes increased to 0.8 wt %. In addition, the weight loss of the polymer films during heating at 300 under vacuum for 7 days, is reported in FIG. 4. A significant weight loss occurs in the first day of the drying and subsequently more gradual weight loss is observed for the film. The addition of the nanotubes to the polymer did not have a marked effect of the solvent evaporation.

TABLE 3

Mechanical properties of PLLA 38 films after vacuum annealing at different temperatures and duration periods.

| | Modulus (GPa) | Yield strength (MPa) | Strain at Break (%) | Toughness (MPa/%) |
|---|---|---|---|---|
| PLLA 38 film after vacuum annealing for 1 h at 120° C. | 2.0 ± 0.03 | 48.25 ± 0.4 | 3.8 ± 1.0 | 1.0 ± 0.5 |
| PLLA 38 film with 0.25 wt % INT-$WS_2$ after vacuum annealing for 1 h at 120° C. | 2.5 ± 0.1 | 48.9 ± 3.8 | 3.6 ± 0.6 | 1.1 ± 0.3 |
| PLLA 38 film with 0.4 wt % INT-$WS_2$ after vacuum annealing for 1 h at 120° C. | 2.25 ± 0.04 | 45.6 ± 0.6 | 3.8 ± 0.3 | 1.1 ± 0.1 |
| PLLA 38 film after vacuum annealing for 6 h at 120° C. | 2.0 ± 0.3 | 50.6 ± 9.2 | 3.1 ± 0.6 | 1.0 ± 0.65 |

TABLE 3-continued

Mechanical properties of PLLA 38 films after vacuum annealing at different temperatures and duration periods.

| | Modulus (GPa) | Yield strength (MPa) | Strain at Break (%) | Toughness (MPa/%) |
|---|---|---|---|---|
| PLLA 38 film with 0.25 wt % INT-WS$_2$ after vacuum annealing for 6 h at 120° C. | 2.35 ± 0.25 | 60.1 ± 11.9 | 3.8 ± 0.8 | 1.3 ± 0.4 |
| PLLA 38 film with 0.4 wt % INT-WS$_2$ after vacuum annealing for 6 h at 120° C. | 2.1 ± 0.1 | 45.2 ± 2.7 | 4.2 ± 1.9 | 1.3 ± 0.8 |
| PLLA 38 film after vacuum annealing for 48 h at 40° C. | 2.0 ± 0.2 | 36.2 ± 7.5 | 4.1 ± 2.8 | 0.9 ± 0.9 |
| PLLA 38 film with 0.25 wt % INT-WS$_2$ after vacuum annealing for 48 h at 40° C. | 1.9 ± 0.1 | 39.4 ± 0.9 | 11.3 ± 3.5 | 3.2 ± 0.6 |
| PLLA 38 film with 0.4 wt % INT-WS$_2$ after vacuum annealing for 48 h at 40° C. | 2.4 ± 0.1 | 46.2 ± 1.9 | 6.5 ± 0.5 | 2.3 ± 0.3 |
| PLLA 38 film after vacuum annealing for 7 days at 30° C. | 1.6 ± 0.1 | 26.6 ± 1.5 | 3.2 ± 0.4 | 0.6 ± 0.1 |
| PLLA 38 film with 0.25 wt % INT-WS$_2$ after vacuum annealing for 7 days at 30° C. | 1.8 ± 0.02 | 29.7 ± 1.2 | 2.9 ± 0.3 | 0.6 ± 0.1 |
| PLLA 38 film with 0.4 wt % INT-WS$_2$ after vacuum annealing for 7 days at 30° C. | 1.9 ± 0.1 | 39.5 ± 2.0 | 5.4 ± 0.7 | 1.5 ± 0.2 |
| PLLA 38 film with 0.7 wt % INT-WS$_2$ after vacuum annealing for 7 days at 30° C. | 2.4 ± 0.1 | 46.1 ± 1.5 | 3.7 ± 0.5 | 1.1 ± 0.2 |

TABLE 4

Mechanical properties of PLLA 24 films after vacuum annealing in 30° C. for 7 days.

| | Modulus (GPa) | Yield strength (MPa) | Strain at failure (%) | Toughness (MPa/%) |
|---|---|---|---|---|
| PLLA 24 film after vacuum annealing for 7 days at 30° C. | 1.4 ± 0.05 | 22.0 ± 4.1 | 3.5 ± 0.6 | 1.2 ± 0.3 |
| PLLA 24 film with 0.25 wt % INT-WS$_2$ after vacuum annealing for 7 days at 30° C. | 1.8 ± 0.05 | 41.5 ± 1.4 | 8.1 ± 1.5 | 2.0 ± 0.4 |
| PLLA 24 film with 0.5 wt % INT-WS$_2$ after vacuum annealing for 7 days in 30° C. | 2.8 ± 0.2 | 60.9 ± 2.8 | 18.4 ± 5.2 | 5.7 ± 0.7 |
| PLLA 24 film with 0.8 wt % INT-WS$_2$ after vacuum annealing for 7 days in 30° C. | 2.2 ± 0.2 | 43.7 ± 3.5 | 10.3 ± 2.4 | 3.8 ± 1.2 |

Example 5

High-Resolution Scanning Electron Microscopy (HRSEM)

Figure 5A:
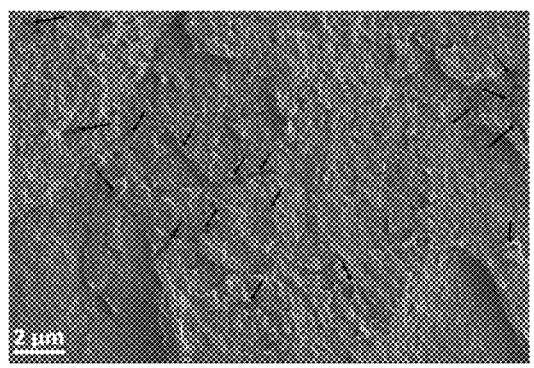
FIGS. 5A-5B depict HRSEM images of the cross-section of a film of PLLA with 0.5 wt % $INT-WS_2$.
Figure 5B:
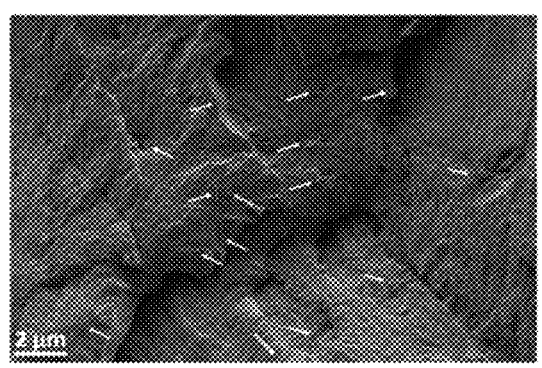
Figure 6A:
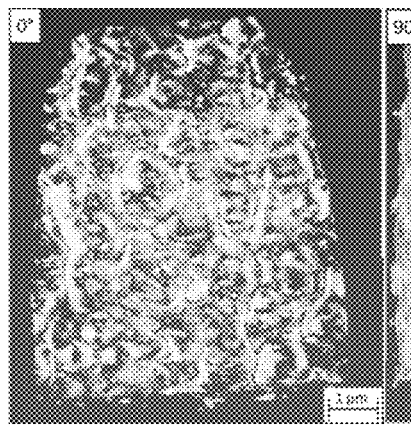
FIGS. 6A-6D depict images from 360° revolving of the sample (sample 1; see table 5) obtained with micro-XCT of PLLA 38 film with 0.5 wt % $INT-WS_2$ before tensile test. Please note that the pictures are shown in 3D perspective.
Figure 6B:
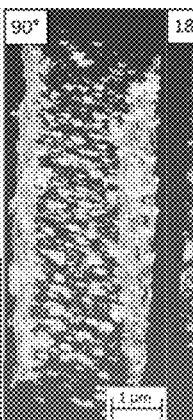
Figure 6C:
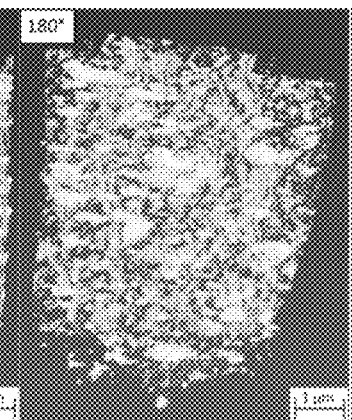
Figure 6D:
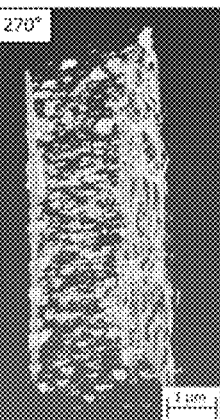
Figures 7A, 7B, 7C, 7D:
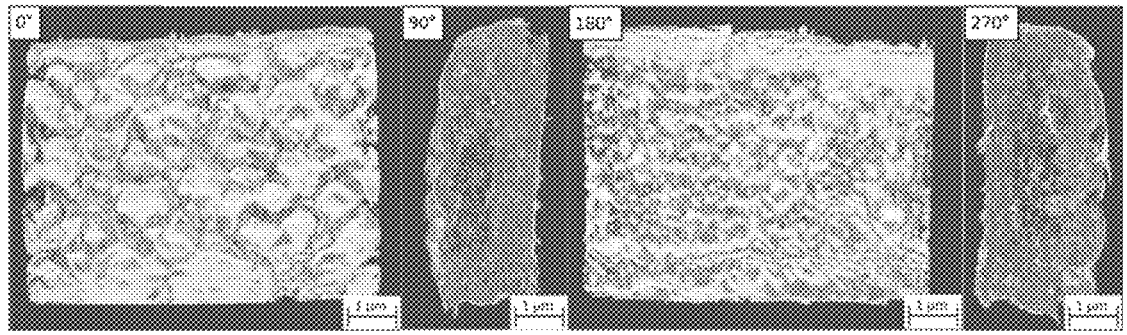
FIGS. 7A-7D depict images from 360° revolving of the sample (sample 1; see table 5) obtained by micro-XCT of PLLA 38 Film with 0.5 wt % $INT-WS_2$ after tensile test in the neck zone near the fracture point. Please note that the sample width is reduced compared to the untested sample. Furthermore, the nanotubes are visibly oriented in the cross-section view.
Figures 8A, 8B, 8C, 8D:
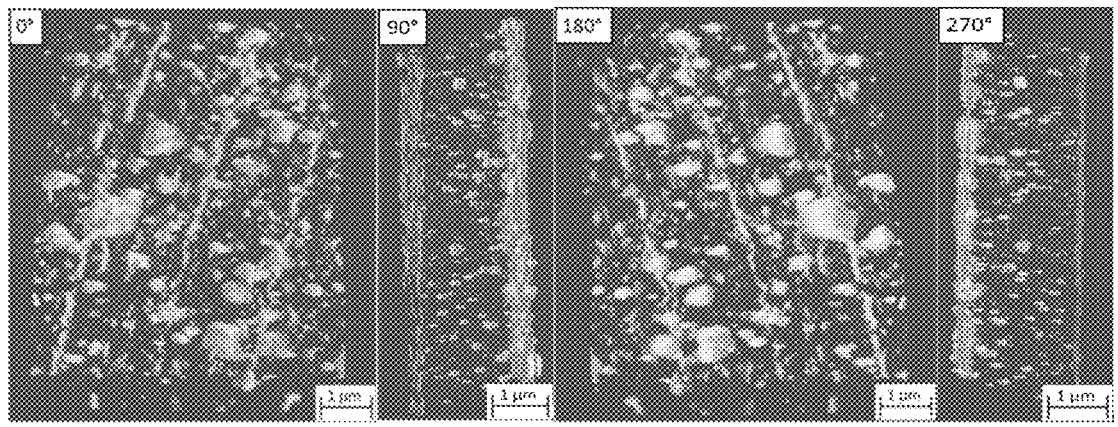
FIGS. 8A-8D depict images from 360° video in the micro-XCT of PLLA 38 film with 1 wt % $INT-WS_2$ (sample 2; see table 5) before tensile test. The nanotubes are highly agglomerated compared with the 0.5 wt % specimen. Note the difference between the top (thin) and bottom (thick) surfaces of the sample. The stripes in 0 and 180° are obtained by the modulated morphology of the Teflon surface.
Figures 9A, 9B, 9C, 9D:
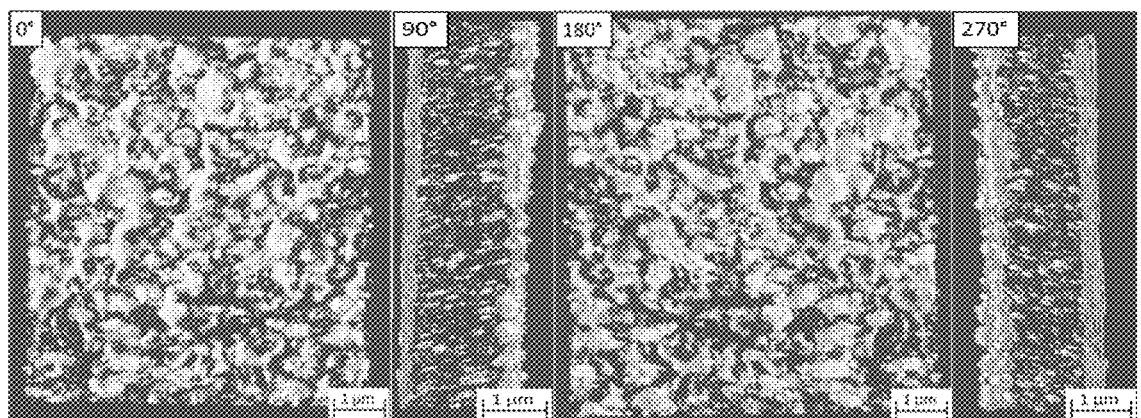
FIGS. 9A-9D depict images from the 360° video in the micro-XCT of PLLA 38 film with 1 wt % $INT-WS_2$ (sample 2; see table 5) after tensile test.
Figures 10A, 10B, 10C, 10D:
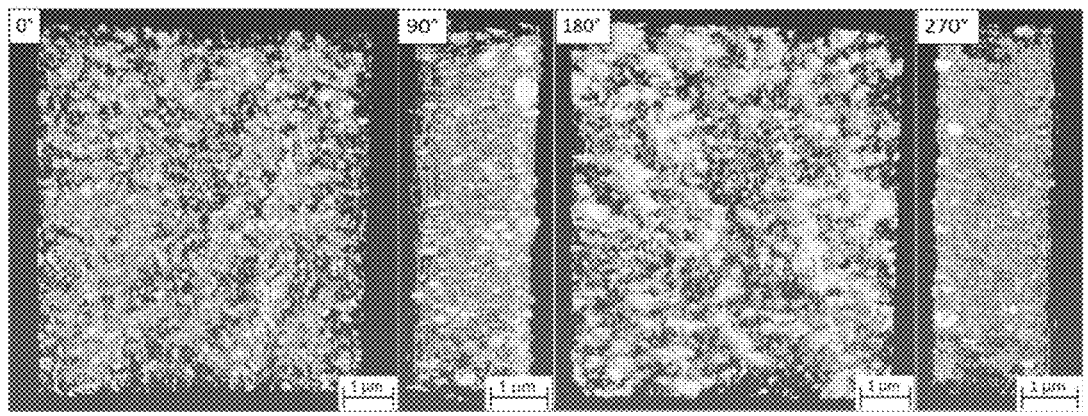
FIGS. 10A-10D depict images from the 360° video in the micro-XCT of PLLA 38 film with 3 wt % $INT-WS_2$ (sample 3; see table 5) before tensile test.
Figures 11A, 11B, 11C, 11D:
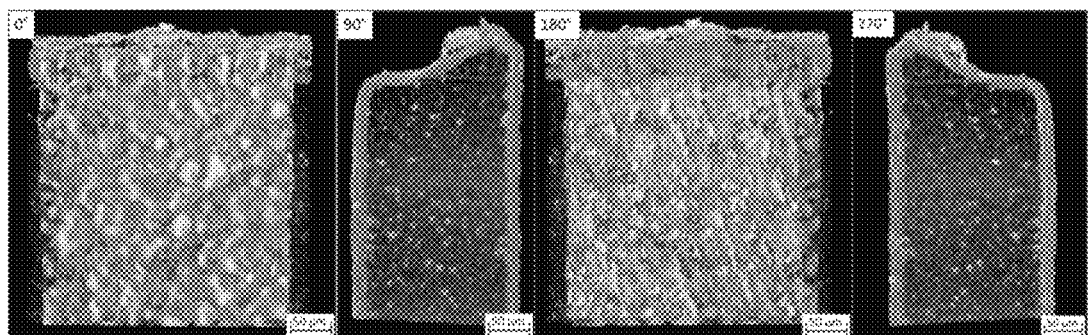
FIGS. 11A-11D depict images from the 360° video in the micro-XCT of PLLA 24 film with 0.5 wt % $INT-WS_2$ (sample 4; see table 5) with long extension before tensile test; scale: 50 μm. The stripes visible in 180° are obtained by the surface modulation of the Teflon container used for the preparation of the specimen.
Figures 12A, 12B, 12C, 12D:
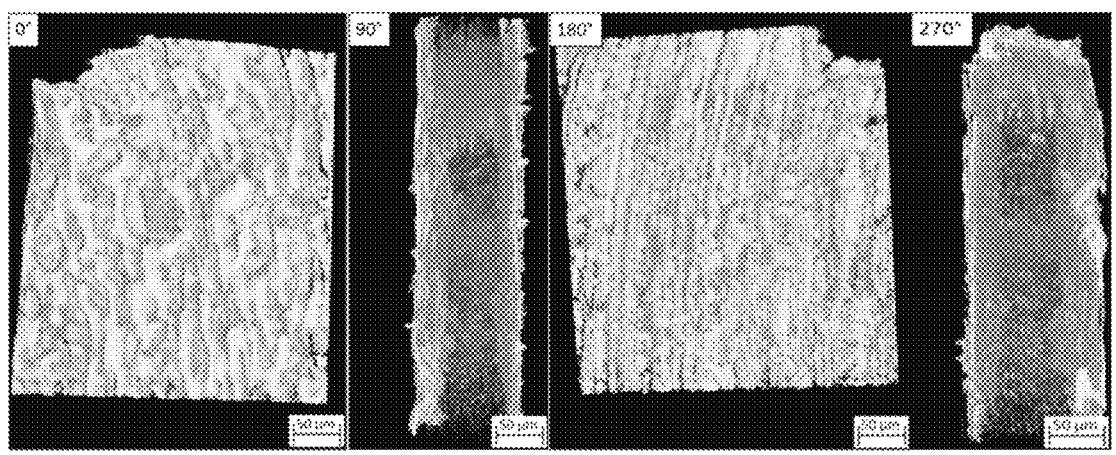
FIGS. 12A-12D depict images from the 360° video in the micro-XCT of PLLA 24 film with 0.5 wt % $INT-WS_2$ (sample 4; see table 5) with long extension after tensile test; scale: 50 μm.

The morphology of the cross-section of the PLLA films without and with different concentrations of INT-WS$_2$ was examined by HRSEM. This analysis showed that the nanotubes (prepared via drying/annealing for 7 days at 30° C.) were successfully embedded in the polymer and they were very well dispersed in the polymer matrix, see FIGS. 5A-B for PLLA 24 and PLLA 38, respectively. The specimen were prepared by immersion in liquid nitrogen and breaking. The morphology of the two specimen are quite different. While the PLLA 24 presents a relatively smooth surface, the surface of the broken PLLA 38 (B) is rather rough. The surface of the PLLA 38 is quite rough due likely to its low fracture toughness and brittleness. The nanotubes are positioned between the fracture planes, which is a common behavior of nanotubes as nanofillers in reinforced polymer matrices and hence contribute to the polymer reinforcement.

Example 6

X-Ray Tomographic Microscopy (Micro-XCT)

The micro-XCT analysis was done with the PLLA 38 films before and after tensile test with 0.5 and 1 wt % and PLLA 38 film and before the tensile test with 3 wt % INT-WS$_2$. Table 5 shows the mechanical properties of the films. The micro-XCT analysis helped to understand the dispersion of the nanotubes by showing 3D imaging of the samples. The film with 0.5 wt % INT-WS$_2$ before and after the tensile test (FIGS. 6A-6D and FIGS. 7A-7D) showed good dispersion of the nanotubes in the film with very little agglomerates. In FIGS. 6A-6D and FIGS. 7A-7D, the thickness of the surface layer enriched with nanotubes is largely exaggerated. However, the difference between the top (thin) and bottom (thick) layer enriched with agglomerated nanotubes is clearly visible. In contrast to that, the PLLA 38 film with 1 wt % INT-WS$_2$ before and after tensile test (FIGS. 8A-8D and FIGS. 9A-9D) and PLLA 38 film with 3 wt % INT-WS$_2$ after tensile test (FIGS. 10A-10D), showed extensive agglomeration of the nanotubes and their sedimentation at the bottom of the film, near the surface of the Teflon plates. In the figures below, snapshots are taken from the video movie. Note that the video pictures are taken with 3D-proportions (perspective). Consequently, the view of the films pointing to us (head-on) are distorted and thus misleading. In particular, the surface films (brighter contrast) on the two sides (in reality the bottom and upper sides of the film) are few microns thick and not 100 microns.

TABLE 5

Mechanical properties of PLLA films measured in micro-XCT analysis.

| | Modulus (GPa) | Yield strength (MPa) | Strain at Break (%) | Toughness (MPa/%) |
|---|---|---|---|---|
| PLLA 38 film with 0.5 wt % INT-WS$_2$ sample 1 | 2.4 | 49.3 | 14.0 | 6.1 |
| PLLA 38 film with 1 wt % INT-WS$_2$ sample 2 | 4.0 | 68.25 | 29.8 | 20.0 |
| PLLA 38 film with 3 wt % INT-WS$_2$ sample 3 | 3.4 | 57.4 | 11.7 | 4.9 |
| PLLA 24 film with 0.5 wt % INT-WS$_2$ sample 4 | 2.4 | 60.7 | 75.7 | 40.5 |
| PLLA 24 film with 0.5 wt % INT-WS$_2$ sample 5 | 2.0 | 40.7 | 3.2 | 1.0 |

The resolution of the micro-XCT is limited to about half a micron in the current situation. The nanotubes consist of a heavy element (tungsten) but they are tiny and their concentration is small. Their large aspect ratio, though, allows direct viewing of small nanotubes'-agglomerates and even single ones. The orientation of the nanotubes in the PLLA is an important parameter in their function as a reinforcement element. Therefore, images from the videos of PLLA film with 0.5 wt % INT-WS$_2$ were analyzed. The white spots were thought to be associated with nanotubes' agglomerates.

However, due to the lack of resolution in the micro-XCT instrument, it could not tell exactly how many nanotubes there were in every spot but it definitely could show the agglomerates of the nanotubes, which were large blocks of the white area. It can be concluded from the micro-XCT analysis that the agglomeration of the nanotubes was relatively minor below 1 wt %. The main conclusion from samples of PLLA film with 0.5 wt % INT-WS$_2$ before and after the tensile test is the change in the orientation of the nanotubes due to the loading of the sample. For example, the surface area of the sample before the stretch is a combination of bright (nanotubes) and dark (polymer) areas (see FIGS. 6A-D and FIGS. 7A-D). The bright area is largely due to the random orientation of the tubes. After the stretch, the surface area of the bright zones is reduced, especially in the middle of the sample in the head-on configuration. This effect is believed to be caused due to the aligning of the nanotubes in the direction of the loading.

The images from the videos of PLLA film with 1 wt % INT-WS$_2$ (sample 2; see table 5) show significant agglomerations of nanotubes and sedimentation at the bottom of the samples. The sedimentation is clearly visible by the difference in contrast between the two sides of the samples in a head-on view. The bottom bright film is much thicker than the upper surface film. The agglomeration-sedimentation is the result of the lengthy drying process, which is required in order to get rid of the solvent.

The images from the videos of PLLA film with 3 wt % INT-WS$_2$ (sample 3; see table 5) show clearly the nanotubes agglomerations and sedimentation at the bottom of the film. The agglomeration in this sample explains the premature failure of the film in this concentration.

Another micro-XCT analysis was intended to compare the nanotubes distribution in specimens showing very good and worse mechanical properties. Two samples were selected for this comparison and their mechanical properties are summarized also in Table 5. The Micro-XCT results for PLLA 24 films with 0.5 wt % INT-WS$_2$ with long extension (75%) before and after tensile test are summarized in FIGS. 11A-11D and FIGS. 12A-12D. The results for a similar specimen with short extension (3.2%) are summarized in FIGS. 13A-13D and FIGS. 14A-14D) extension. First, the micro-XCT analysis shows a big improvement in the dispersion of the nanotubes in PLLA 24 compared with PLLA 38 (FIGS. 6A-6D—FIGS. 10A-10D). Furthermore, the film with the long extension (FIGS. 11A-11D and FIGS. 12A-12D) show very good dispersion of the nanotubes in the film with a smooth surface and homogeneous thickness. Please note that the thickness of the strained sample visible at 90 and 270° are appreciably smaller than those in FIGS. 11A-11D (before straining). Also, shear bands of the strained sample are clearly observed at 0 and 180° of FIGS. 12A-12D (after straining). In contrast to that, the PLLA with the short extension (FIGS. 13A-13D and FIGS. 14A-14D) shows agglomeration of the nanotubes along the surface and their sedimentation at the bottom of the film, (near the surface of the Teflon plates), which could make a rough surface and homogeneous thickness.

The images from the videos of PLLA film with 0.5 wt % INT-WS$_2$ with long extension (sample 4; see table 5) before and after the tensile test shows big improvement in the dispersion of the nanotubes. The agglomerates of the nanotubes are rather small and the thickness of the film is homogeneous. The even distribution of the nanotubes prevents weak links, which helps the sample to achieve longer extension by dividing the load uniformly along its entire length.

The images from the videos of PLLA 24 film with 0.5 wt % INT-WS$_2$ (sample 5; see table 5) with short extension before and after the tensile test are shown in FIGS. 13A-13D and FIGS. 14A-14D. The agglomeration of nanotubes led to their partial precipitation during the drying of the specimen, which can be clearly observed in 90 and 270° in FIGS. 13B and 13D. The appearance of bowls in the surface, makes it highly non-uniform producing weak links and poor mechanical behavior for this specimen. The Micro-XCT analysis can also show the cross-section across the sample in all three planes; from this analysis (FIG. 15), the bowl in the surface is placed above a nanotubes' agglomerate which precipitates at the bottom of the sample. Therefore, the nanotubes' agglomerate is a failure point (weak link) in the matrix, which prevents uniform evaporation of the solvent, eventually causing roughness in the surface.

Example 7

Functionalization of the INT-WS$_2$

Figure 16:
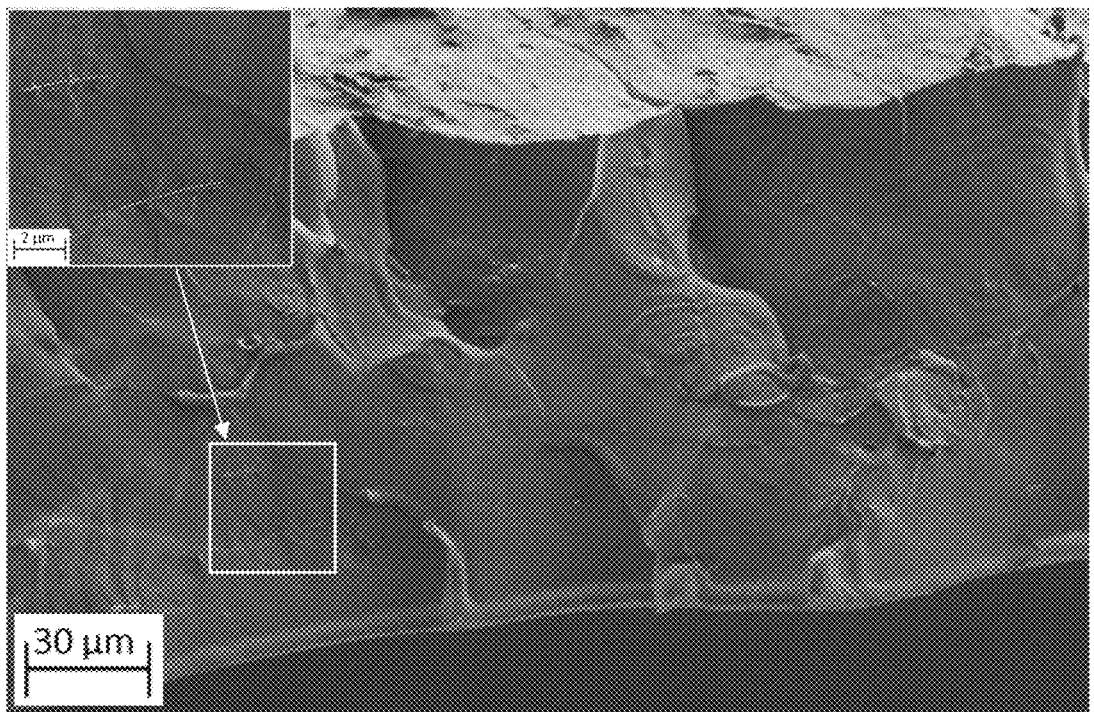
FIG. 16 depicts a SEM image of the cross-section of PLLA 24 film with 0.5 wt % $INT-WS_2$ after breaking in nitrogen liquid. The figure shows circles around the nanotubes, which are the breaking point. Top left square shows a magnification of the indicated area.

FIG. 16 shows SEM image of the cross-section of PLLA 24 film with 0.5 wt % INT-WS$_2$ after breaking in liquid nitrogen. The figure shows circles around the nanotubes, which are the breaking point. This phenomenon indicates the relatively poor adhesion between the nanotubes and the polymers. This observation led to performing functionalization to the nanotubes surface in order to enhance their binding to the polymer matrix.

Functionalization of INT-WS$_2$ with NMP
(N-Methyl-2-pyrrolidone)

Figures 17A, 17B:
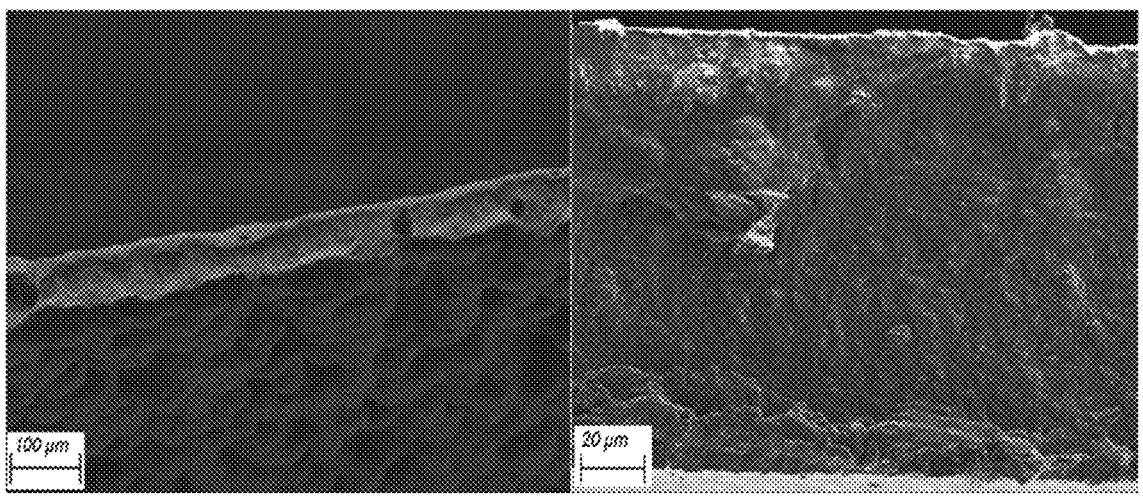

FIGS. 17A-B show SEM analysis of the PLLA 38 film with 1 wt % INT-WS$_2$ after treatment with NMP. The INT-WS$_2$ were found to disperse well in the film (FIG. 17B), but the morphology of the film with the functionalized nanotubes, shows high surface roughness. Table 6 shows the mechanical properties of the PLLA 38 films with different weight percent of INT-WS$_2$ and after annealing for 6 h in 120° C. The PLLA with NMP-treated tubes showed improved mechanical properties compared with the PLLA blank up to 120% but lower strength compared to the PLLA with neat nanotubes. Annealing the films at 120° C. resulted in improved strength up to 130% compared to the blank PLLA 38 but the ductility of the specimen went down, substantially due to the surface roughening (see FIG. 17A).

TABLE 6

Mechanical properties of - PLLA 38 film with INT-WS2 after treatment with NMP.

|  | Modulus (GPa) | Yield strength (MPa) | Strain at Break (%) | Toughness (MPa/%) |
|---|---|---|---|---|
| PLLA 38 film | 1.5 ± 0.05 | 41.9 ± 10.9 | 1.5 ± 0.6 | 0.6 ± 0.05 |
| PLLA 38 film with 0.25 wt % INT-WS$_2$ after functionalized with NMP | 1.75 ± 0.05 | 38.0 ± 1.6 | 10.4 ± 1.6 | 7.9 ± 2.2 |
| PLLA 38 film with 0.5 wt % INT-WS$_2$ after functionalized with NMP | 1.4 ± 0.02 | 31.7 ± 2.3 | 9.5 ± 2.1 | 2.4 ± 0.6 |
| PLLA 38 film with 1 wt % INT-WS$_2$ after functionalized with NMP | 1.4 ± 0.3 | 67.4 ± 48.9 | 15.4 ± 1.3 | 3.9 ± 0.3 |
| PLLA 38 film with 0.25 wt % INT-WS$_2$ after functionalized with NMP and after vacuum annealing for 6 h in 120° C. | 2.1 ± 0.2 | 38.9 ± 0.5 | 3.3 ± 0.2 | 0.8 ± 0.1 |
| PLLA 38 film with 0. 5wt % INT-WS$_2$ after functionalized with NMP and after vacuum annealing for 6 h in 120° C. | 2.3 ± 0.05 | 56.4 ± 1.0 | 3.8 ± 1.1 | 1.1 ± 0.4 |

Functionalization of INT-WS$_2$ with PEI (polyethylenimine)

The solvent was changed in these experiments because PEI does not dissolve in dichloromethane. Moreover, after functionalization with PEI the nanotubes did not disperse in dichloromethane, but did fully disperse in chloroform. Fortunately, the PEI dissolves in chloroform as well. Table 7 shows the mechanical properties of PLLA 24 film prepared in chloroform as a solvent. Table 8 shows the mechanical properties of PLLA 24 film prepared in the solvent chloroform after functionalization of the nanotubes in PEI. The functionalization of the nanotubes led to improved mechanical properties around 0.5 wt % INT-WS$_2$ (165% improvement compared with neat nanotubes). However, no improvement was observed with 0.25 wt % INT-WS$_2$ compared to the PLLA 24 blank film.

TABLE 7

Mechanical properties of PLLA 24 film (solvent: chloroform).

|  | Modulus (GPa) | Yield strength (MPa) | Strain at Break (%) | Toughness (MPa/%) |
|---|---|---|---|---|
| PLLA 24 film | 1.2 ± 0.1 | 22.0 ± 1.7 | 14.9 ± 6.7 | 1.5 ± 0.7 |
| PLLA 24 film with 0.5 wt % INT-WS$_2$ | 1.6 ± 0.1 | 31.5 ± 0.7 | 9.2 ± 1.4 | 2.3 ± 0.4 |

TABLE 8

Mechanical properties of PLLA 24 film with INT-WS$_2$ after treatment with PEI.

|  | Modulus (GPa) | Yield strength (MPa) | Strain at Break (%) | Toughness (MPa/%) |
|---|---|---|---|---|
| PLLA 24 film | 2.1 ± 0.3 | 39.0 ± 3.0 | 26.6 ± 6.2 | 9.2 ± 2.2 |
| PLLA 24 film with 0.25 wt % INT-WS$_2$ after functionalization with PEI | 1.2 ± 0.1 | 24.6 ± 3.0 | 58.3 ± 44.2 | 14.0 ± 12.0 |
| PLLA 24 film with 0.5 wt % INT-WS$_2$ after functionalization with PEI | 2.65 ± 0.2 | 47.3 ± 3.8 | 41.5 ± 29.5 | 16.3 ± 13.5 |
| PLLA 24 film with 1 wt % INT-WS$_2$ after functionalization with PEI | 2.15 ± 0.2 | 39.4 ± 1.9 | 15.1 ± 16.6 | 4.4 ± 5.35 |

Functionalization of INT-WS$_2$ with PEG (Polyethylene glycol)

Table 9 shows the mechanical properties of PLLA 24 film with different concentrations of INT-WS$_2$ after functionalization in PEG. Both strength and ductility of the films with nanotubes were improved after functionalization. As the concentrations of the nanotubes increased, the ductility of the film improved first. Further increase of the nanotube concentration led also to improvement in the strength. The big improvement is also around 0.5 wt % INT-WS$_2$ (by 150% from the neat PLLA 24). Similar trend was observed for the polymer films with nanotubes after functionalization in PEI.

TABLE 9

Mechanical properties of PLLA 24 film with INT-WS2 after treatment with PEG.

|  | Modulus (GPa) | Yield strength (MPa) | Strain at Break (%) | Toughness (MPa/%) |
|---|---|---|---|---|
| PLLA 24 film | 1.3 ± 0.1 | 22.3 ± 1.8 | 2.9 ± 0.7 | 0.4 ± 0.1 |
| PLLA 24 film with 0.25 wt % INT-WS$_2$ after functionalization with PEG | 1.9 ± 0.05 | 28.6 ± 1.8 | 9.1 ± 1.3 | 1.8 ± 0.6 |
| PLLA 24 film with 0.5 wt % INT-WS$_2$ after functionalization with PEG | 1.9 ± 0.3 | 40.6 ± 7.6 | 10.0 ± 5.1 | 1.8 ± 0.5 |
| PLLA 24 film with 1 wt % INT-WS$_2$ after functionalization with PEG | 2.0 ± 0.05 | 34.8 ± 1.0 | 2.9 ± 0.2 | 0.7 ± 0.1 |

Example 8

Differential Scanning Calorimetry (DSC)

Figure 18A:
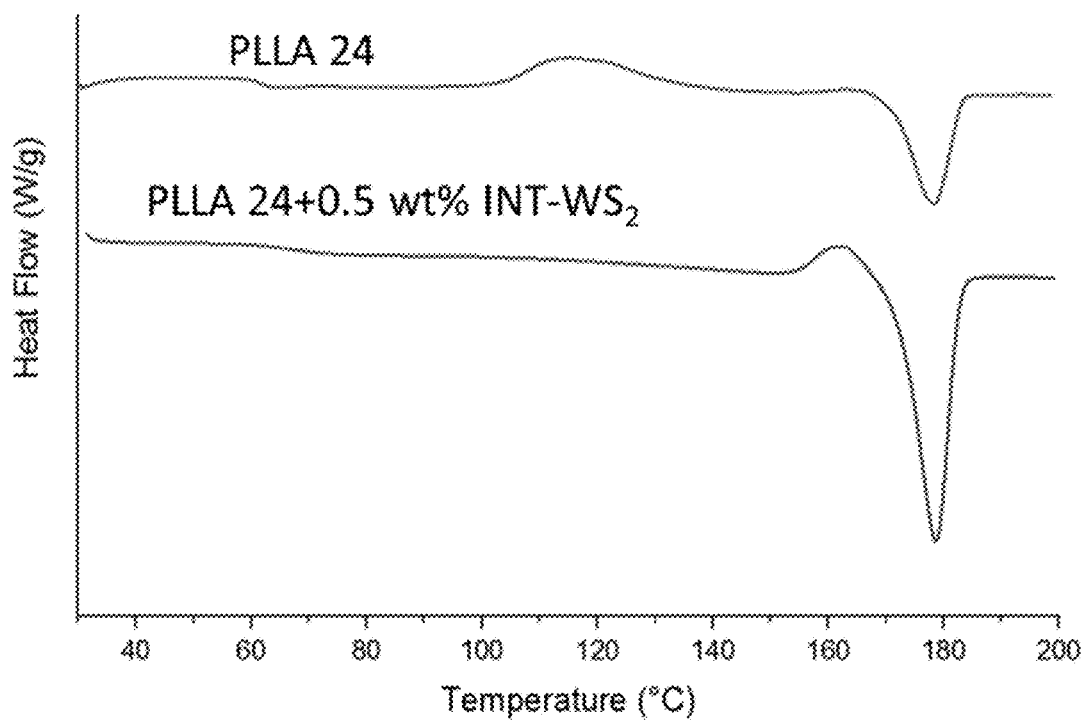
FIGS. 18A-18B depict differential scanning calorimetry (DSC) melting thermograms (heating) of neat PLLA 24 (top thermograms) and PLLA 24 with 0.5 wt % $INT-WS_2$ (bottom thermograms).
Figure 18B:
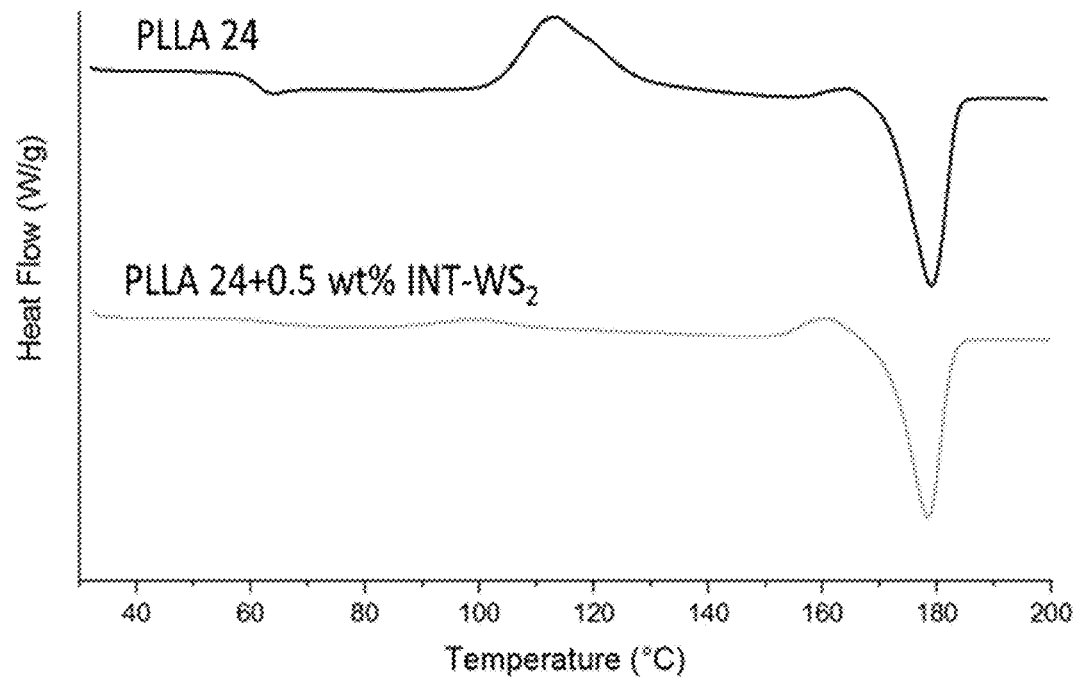

The $T_g$, $T_{cc}$, $T_m$ $\Delta H_{cc}$ and $\Delta H_m$ were calculated from the DSC heating curves (see FIG. 18A-18B). $T_c$ and $\Delta H_c$ were obtained from the cooling curves.

TABLE 10

DSC parameters of PLLA 24 and PLLA with 0.5 wt % INT-WS$_2$ films.
A-immediately after preparation and B-after one year

|   |   | $T_g$ (C.) | $T_{cc}$ (C.) | $H_{cc}$ (J/g) | $T_m$(C.) | $H_m$ (J/g) |
|---|---|---|---|---|---|---|
| A | PLLA 24 | 61.7 ± 0.4 | 114.8 ± 0.3 | 32.4 ± 12.0 | 178.6 ± 0.4 | 33.9 ± 12.2 |
|   | PLLA 24 with 0.5 wt % INT-WS$_2$ | 65.5 ± 1.7 | 107.9 ± 7.9 | 3.1 ± 0.6 | 178.9 ± 0.3 | 37.9 ± 1.5 |
| B | PLLA 24 | 61.8 ± 0.3 | 114.6 ± 0.6 | 38.9 ± 3.4 | 178.8 ± 0.5 | 39.2 ± 3.4 |
|   | PLLA 24 with 0.5 wt % INT-WS2 | 62.2 ± 0.2 | 100.4 ± 0.8 | 6.7 ± 2.2 | 178.8 ± 0.4 | 35.4 ± 0.8 |

|   |   | $T_c$(° C.) | $\Delta H_c$ (J/g) | $X_c$ (%) | $(1-\lambda)_c$ (%) |
|---|---|---|---|---|---|
| A | PLLA 24 | 101.6 ± 0.4 | 2.0 ± 0.1 | 1.6 ± 0.2 | 2.1 ± 0.4 |
|   | PLLA 24 with 0.5 wt % INT-WS$_2$ | 103.0 ± 0.9 | 30.6 ± 6.1 | 37.4 ± 2.1 | 32.9 ± 6.6 |
| B | PLLA 24 | 101.8 ± 0.2 | 2.2 ± 0.4 | 0.3 ± 0.01 | 2.4 ± 0.4 |
|   | PLLA 24 with 0.5 wt % INT-WS2 | 100.3 ± 0.2 | 23.9 ± 1.2 | 30.9 ± 2.5 | 25.6 ± 1.3 |

Table 10 shows the degree of crystallinity as well as the glass transition temperature of pristine PLLA 24 films and films with 0.5 wt % INT-WS$_2$ immediately after preparation and after a year. The neat PLLA 24 presented very low degree of crystallinity (1.6%-heating; 2.1—cooling), which could be attributed to the preparation processing, i.e. solvent casting and vacuum annealing at 30° C. The low value of crystallinity remained virtually unchanged after one year. In contrast, the PLLA 24 film containing 0.5 wt % INT-WS$_2$ presented a relatively high value of crystallinity (37.4%-heating and 32.9%-cooling). After one year the specimen with the nanotubes showed a ~20% drop in crystallinity. It can be concluded therefore, that the nanotubes function as a promoter for nucleation and crystallization in the polymer matrix, i.e. the DSC analysis showed that the nanotubes induce higher crystallinity in the PLLA, due likely to their serving as nucleation center (M. Naffakh, C. Marco, and G. Ellis, "Development of novel melt-processable biopolymer nanocomposites based on poly(l-lactic acid) and WS$_2$ inorganic nanotubes," *CrystEngComm*, vol. 16, no. 23, pp. 5062-5072, 2014). In addition, the crystallinity suffered mild depreciation after a delay of one year (~20%), which entails that the nanotubes function also as inhibitor for the PLLA degradation.

Example 9

X-Ray Diffraction (XRD) Analysis

Figure 19A:
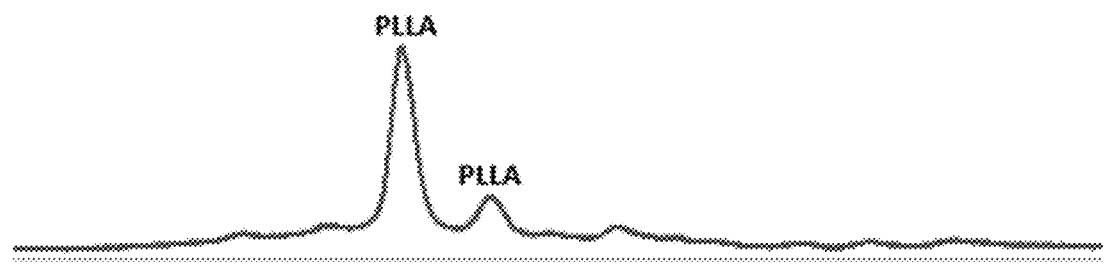
FIGS. 19A-19C depict XRD patterns of FIG. 18A: PLLA 38 film.
Figure 19B:
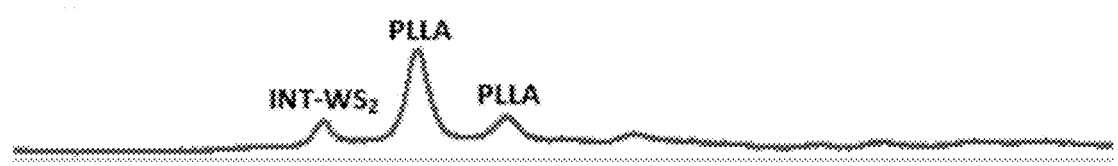
Figure 19C:
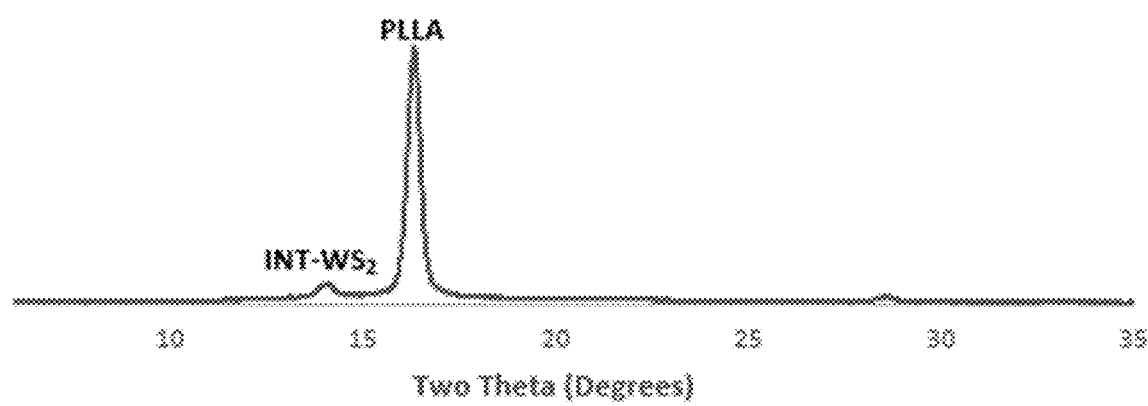
Figure 20:
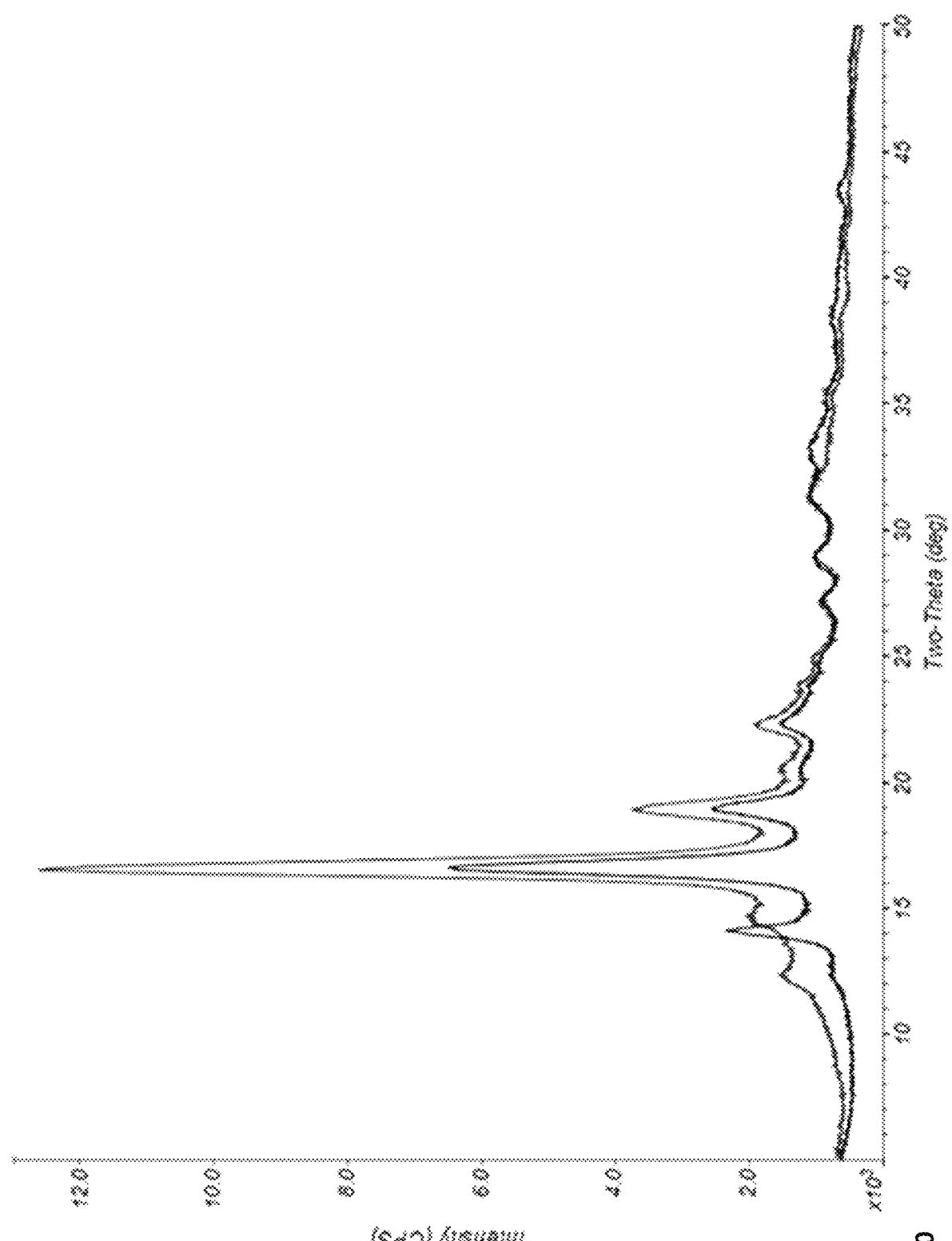
FIG. 20 depicts XRD patterns of PLLA 38 film (top curve) and PLLA 38 film (bottom curve) with 1 wt % INT-WS$_2$.
Figure 21:
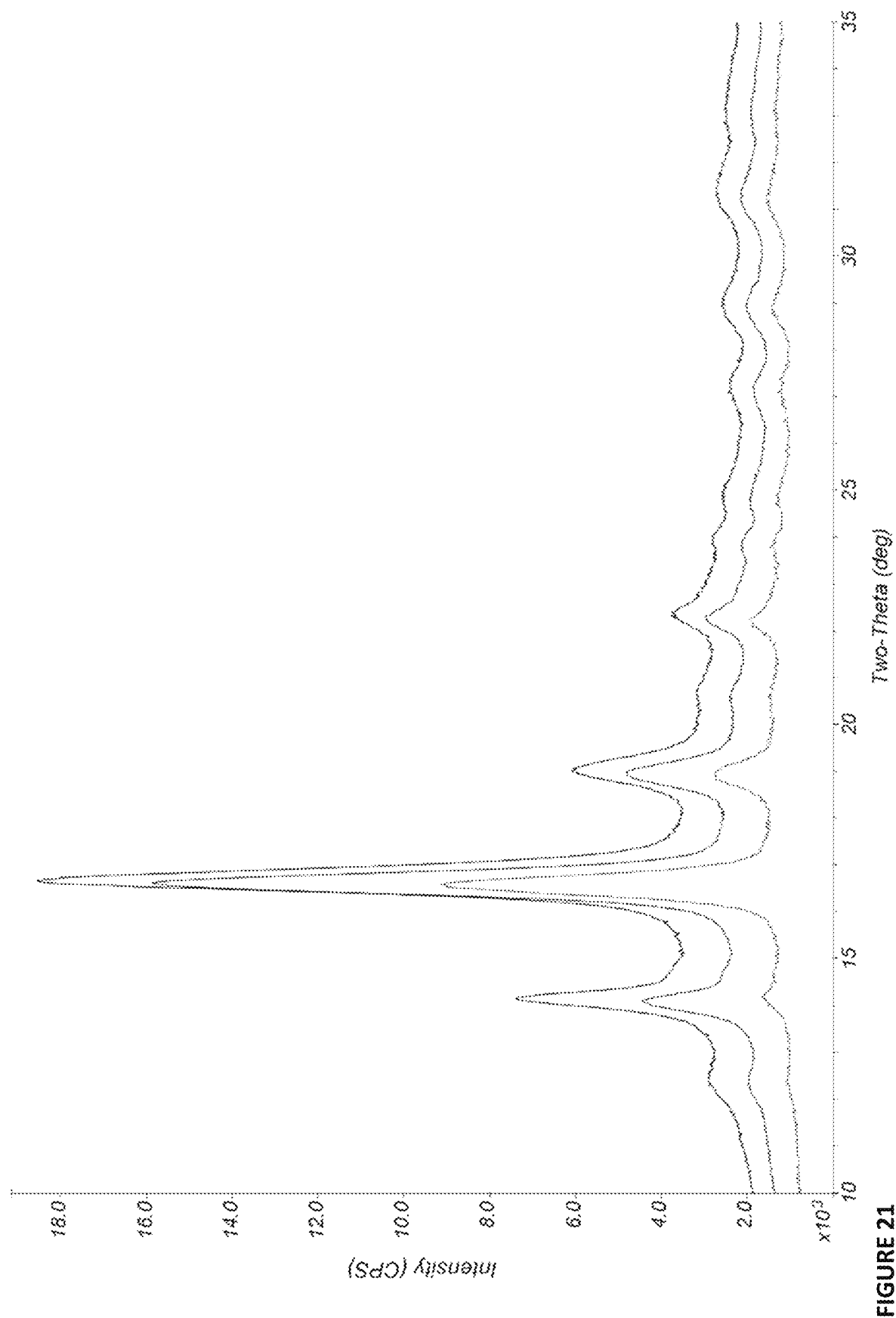
FIG. 21 depicts XRD pattern of the PLLA 24 specimen with 0.5 wt % INT-WS$_2$ immediately after preparation (top curve); and of the same sample one year later from both sides: back surface (middle curve) and front surface (bottom curve).

FIGS. 19A-19C show the XRD analysis of PLLA 38 in two forms: blank film (FIG. 19A) and film with 1 wt % INT-WS$_2$ (FIG. 19B); and PLLA 38 wires with 1 wt % INT-WS$_2$ (FIG. 19C). The samples of FIGS. 19A-19B were prepared by solvent casting and sample C was prepared by extrusion. Not surprisingly, the extruded wire showed the narrowest FWHM of the 16.5° PLLA peak, i.e. the largest crystallites. This observation suggests that the polymer in the extruded wire has a preferred orientation. Due to the texture in the sample of FIG. 19C, it is not possible to compare its degree of crystallinity with the other samples (FIGS. 19A-19B). FIG. 20 displays the XRD pattern of the two samples presented in FIGS. 19A-19B but in a higher resolution scanning mode. This result shows a decreasing intensity of the spectrum profile at angles between 5 and 25 degrees for the sample with INT-WS$_2$ in comparison with the neat polymer (PLLA 38). This reduction is attributed to the lower irradiation volume (lower X-ray penetration depth) in the sample with INT-WS$_2$ (tungsten has much higher X-ray absorption coefficient than the light elements of the polymer). The degree of crystallinity of the samples of FIGS. 19A-19B was calculated by comparing the total area under all the crystal peaks and the area under the amorphous halo. This calculation shows that the crystallinity of the neat PLLA 38 is about 60%, while the PLLA 38 with 1 wt % INT-WS$_2$ has a crystallinity of about 70%. Thus, the nanotubes induce increased crystallinity of the polymer but the error range for the XRD of all the samples was too large to make a definite conclusion regarding the influence of the nanotubes on the PLLA crystallinity. Another XRD analysis was performed on the neat PLLA 24 film and the one with 0.5 wt % INT immediately after fabrication and one year later (kept in a desiccator). The top curve in FIG. 21 shows the XRD pattern of the PLLA 24 specimen with nanotubes immediately after preparation. The same sample one year later was examined by XRD (FIG. 21, middle and bottom curves). The sample was exposed to the XRD radiation from both sides. It appears that the two faces of the specimen exhibited a similar XRD pattern for the PLLA 24 peaks (16.5, 18 and 22°) and did not vary compared with the sample analyzed immediately after fabrication (FIG. 21, top curve). The blank sample (not shown) did not reveal any degradation in its crystallinity after one year in desiccator, either. One can therefore conclude that the PLLA 24 fabricated by casting a film from DCM is stable for at least one year under the vacuum of the desiccator (FIG. 21, middle and bottom curves). Interestingly though, the two sides of the samples showed different signal, with the back surface (FIG. 21, middle curve) showing higher intensity of the 14 signal than the front surface (bottom curve). This result is consistent with the Micro-XCT analysis, which clearly showed partial sedimentation of the nanotubes during the evaporation of the solvent.

Example 10

Coefficient of Friction

The structure of $INT-WS_2$ allow rolling under pressure, therefore they are commercially used as superior solid lubricants for a variety of tribological applications and for polymer reinforcement. However, measurements done on native samples containing the nanotubes (without any surface treatment or run-in procedure) did not show any improvement compared to the neat polymer samples. Running in the sample 20 times back and forth, or rubbing the surface with SiC paper had major influence with precipitous reduction of the friction coefficient for samples containing the nanotubes as shown in Table 11.

TABLE 11

Friction coefficients of PLLA 24 films: $\mu_s$—static friction, $\mu_k$—kinetic friction.

| Type of test | | PLLA 24 film | PLLA 24 film with 0.5 wt % $INT-WS_2$ |
|---|---|---|---|
| Run 20 times on steel plate | $\mu_s$ | 0.198 ± 0.008 | 0.063 ± 0.005 |
| | $\mu_k$ | 0.186 ± 0.002 | 0.034 ± 0.013 |
| After 5 (run-in) runs | $\mu_s$ | 0.209 ± 0.014 | 0.071 ± 0.005 |
| With 1200 SiC paper | $\mu_k$ | 0.183 ± 0.018 | 0.032 ± 0.012 |
| After run 5 times 150 SiC paper | $\mu_s$ | 0.244 ± 0.017 | 0.065 ± 0.003 |
| | $\mu_k$ | 0.209 ± 0.005 | 0.028 ± 0.002 |

Table 11 shows the static (s) and kinetic friction (k) of the PLLA 24 films. The results show a major reduction in the friction of PLLA 24 films with nanotubes compared to the blank (PLLA 24 film). The rubbing of the sample with SiC paper led to a wear and partial release of nanotubes buried in the polymer matrix under the surface. Therefore, the rubbed specimen exhibited a larger reduction in the friction values compared to the samples run 20 times back and forth (run-in). Quantitatively, the static friction was reduced 3 times and the kinetic friction 7.5 times, compared with neat PLLA films from samples rubbed 5 times with SiC 150 grit. After running 5 times on 1200 SiC paper, the static friction was reduced 3.7 times and only 5.7 times in the kinetic friction.

Example 11

Friction Force

Figure 22A:
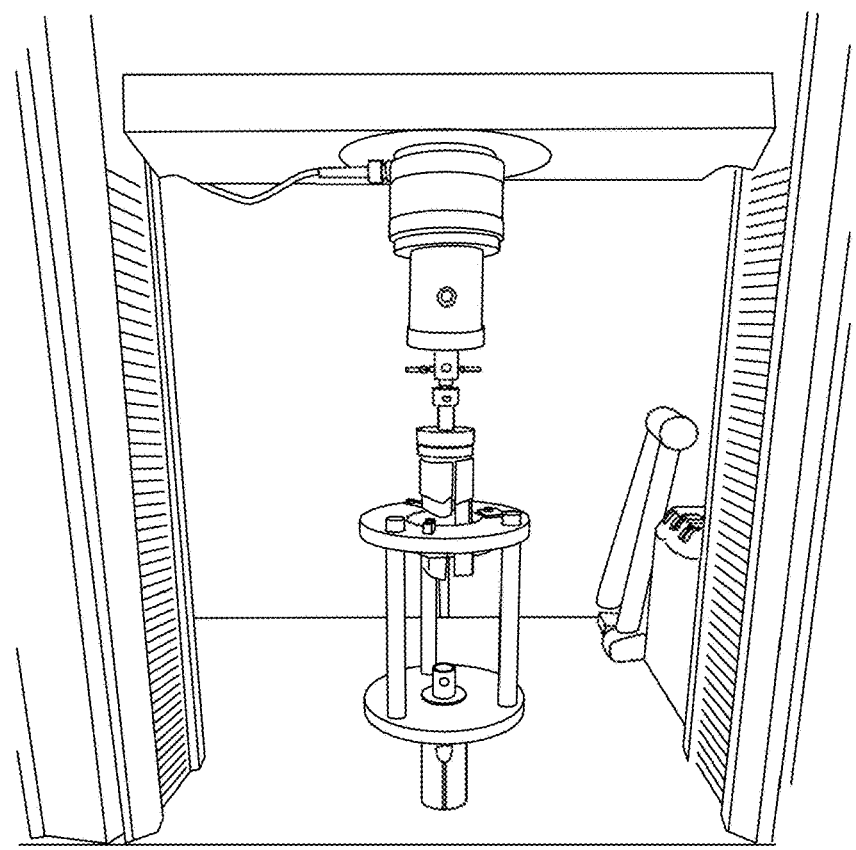
FIGS. 22A-22B depict pictures of modified mock-up model of the urethra-endoscope (UM model) pair on the Instron and attached to the load cell.
Figure 22B:
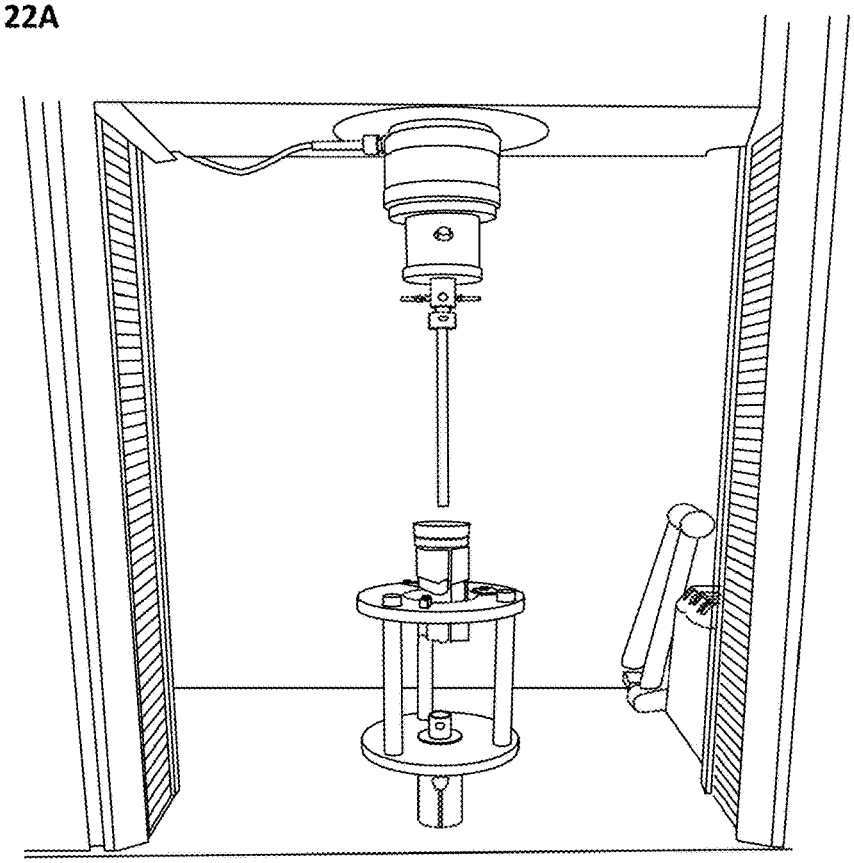

Table 12 summarizes the normalized average friction force for uncoated and polymer or nanocomposite coated stainless steel rod (see experimental setup at FIGS. 22A-22B). The coatings were prepared from different polymers without nanoparticles or nanotubes or from nanocomposites comprising the same polymers and 0.5 wt % $INT-WS_2$. Measurements were carried out in both dry and wet (water) conditions. The coating of the rods were made by dip coatings. A very thin coating film (50-100 µm) was obtained, which allowed to see right away the tribological effects of the nanotubes in the thin polymer's coatings, without any run-in or rubbing procedure. Friction measurements in wet conditions were measured to simulate more closely in-vivo tests.

TABLE 12

Normalized friction force of uncoated and coated stainless steel rod samples. Each number in the table represents an average of three measurements in dry and wet conditions.

| | PLLA 38 | | PLLA 24 | | PLLA (2.1 dL/g) | | PDLLA (0.55 dL/g) | | PDLGA 50/50 (0.4 dL/g) | |
|---|---|---|---|---|---|---|---|---|---|---|
| | Dry | Wet | Dry | Wet | Dry | Wet | Dry | Wet | Dry | Wet |
| Uncoated stainless steel rod | 1.00 | 1.00 | 1.00 | 1.00 | 1.00 | 1.00 | 1.00 | 1.00 | 1.00 | 1.00 |
| Stainless steel rod coated with polymer | 1.73 | 1.73 | 1.75 | 2.66 | 1.42 | 1.41 | 1.57 | 1.38 | 1.47 | 1.30 |
| Stainless steel rod coated with nanocomposite comprising polymer/0.5 wt % INT-WS2 | 0.27 | 0.23 | 0.43 | 0.35 | 0.31 | 0.09 | 1.29 | 1.03 | 1.26 | 0.43 |

The favorable effect of the nanotubes on the friction is significant in all cases. Also, in all cases, the wet friction was smaller than in dry conditions (excluding the case of the PLLA 24 coating without nanotubes/nanoparticles). Importantly, the polymer coating containing the nanotubes exhibit smaller friction (excluding the case of PDLLA in both conditions and PDLGA in dry conditions) than the stainless-steel rod (8 mm), although the coated rod is thicker (on the average-8.1 mm). The nanotubes have the smallest effect on PDLLA, which is amorphous.

Example 12

Rheological Characterization

Figure 23:
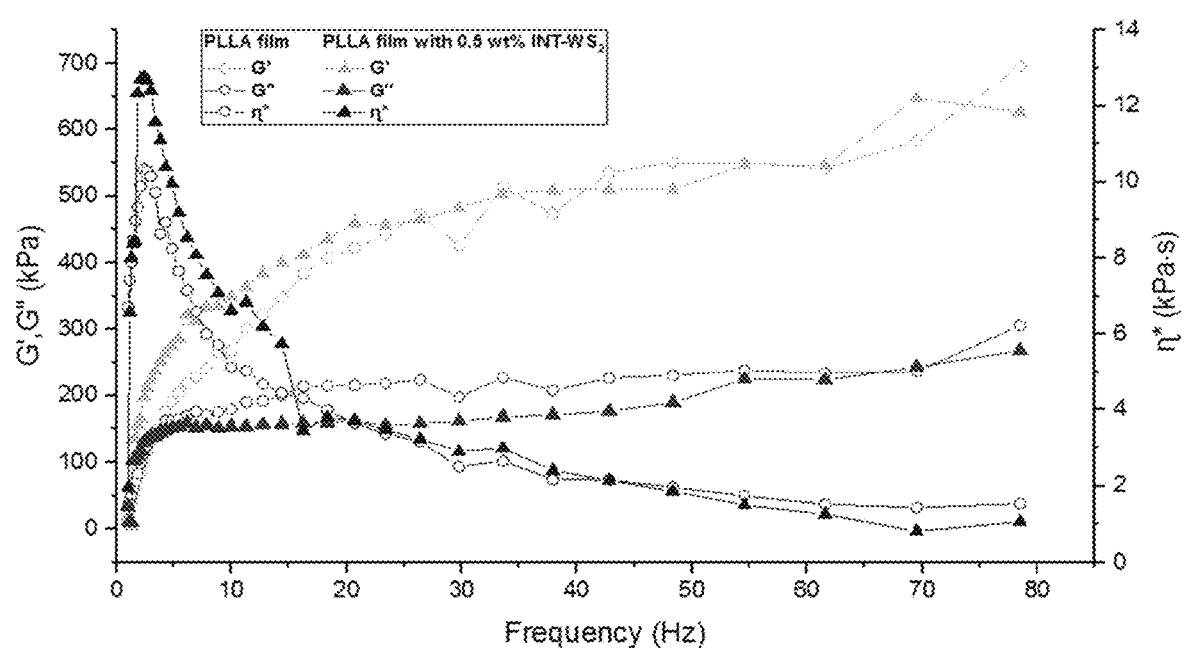
FIG. 23 depicts the complex viscosity ($\eta^*$), the storage modulus (G') and loss modulus (G") versus frequency for PLLA film and PLLA film with 0.5 wt % INT-WS$_2$ at 185° C. For both samples: G' is light grey, G" is darker grey and $\eta^*$ is the darkest grey-black.

Rheological measurements were performed on neat PLLA and PLLA with 0.5 wt % INT-WS$_2$ samples in order to study the influence of the nanotubes on the polymer matrix. FIG. 23 shows the variation of the storage (G') and loss (G") moduli and complex viscosity ($\eta^*$) vs sweep frequency for the samples. The storage and the loss moduli increased as a function of the frequency, which indicate that the polymer chains are fully relaxed and the polymer is in its rubbery zone. The complex viscosity decreased as a function of the frequency showing typical non-Newtonian shear thinning viscosity (A. V. Shenoy, Rheology of Filled Polymer Systems. 1999) behavior in which the complex viscosity decreased linearly with logarithmic increase of the angular frequency. The addition of the nanotubes to the polymer matrix did not lead significant changes in the results.

It is well accepted that addition of even small amounts of carbon nanotubes to polymers increases the static and the dynamic viscosities as well as the storage and loss moduli of the nanocomposite considerably (P. Pötschke, T. D. Fornes, and D. R. Paul, "Rheological behavior of multiwalled carbon nanotube/polycarbonate composites," Polymer (Guildf)., vol. 43, no. 11, pp. 3247-3255, May 2002; and Y. S. Song and J. R. Youn, "Influence of dispersion states of carbon nanotubes on physical properties of epoxy nanocomposites," Carbon N. Y., vol. 43, no. 7, pp. 1378-1385, June 2005). Conversely, the WS$_2$ nanotubes exhibit little tendency to agglomerate and their influence the rheological properties of the nanocomposites (e.g. viscosity and moduli) is very minor, if any. These characteristics have important ramifications on the dispersion of the WS$_2$ nanotubes in the polymer matrix and the future manufacturing processes of such nanocomposites.

Example 13

Raman Spectroscopy

Figure 24:
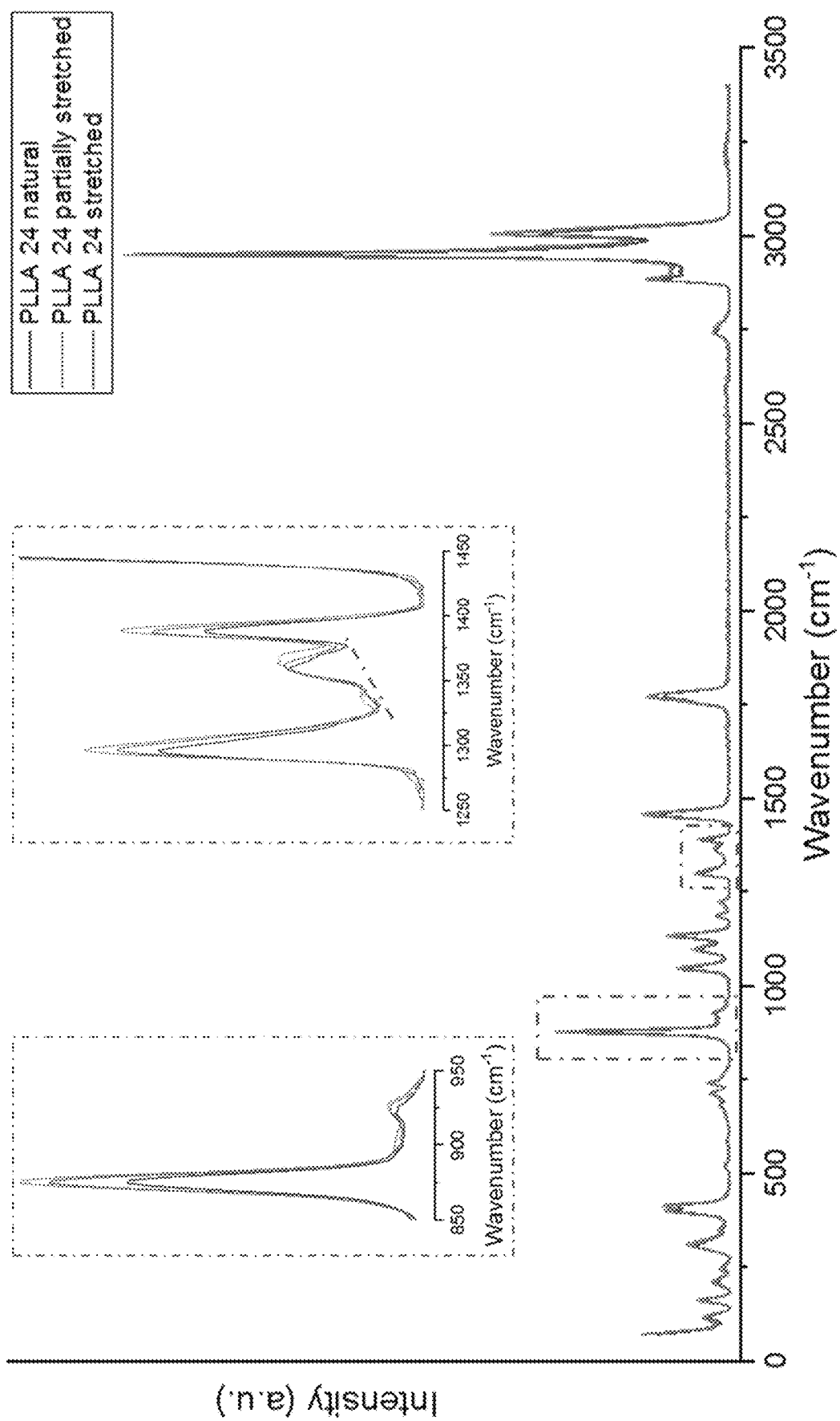
FIG. 24 depicts Raman spectra of PLLA 24 film before (natural) and after tensile test (partially stretched and stretched). Inset: Raman spectra in 850-950 cm$^{-1}$ and 1250-1450 cm$^{-1}$ regions; top spectrum is PLLA 24 partially stretched, middle spectrum is PLLA 24 stretched and bottom spectrum is natural PLLA 24. The dashed line represents the slope between 1250-1450 cm$^{-1}$ bands of PLLA.
Figure 25A:
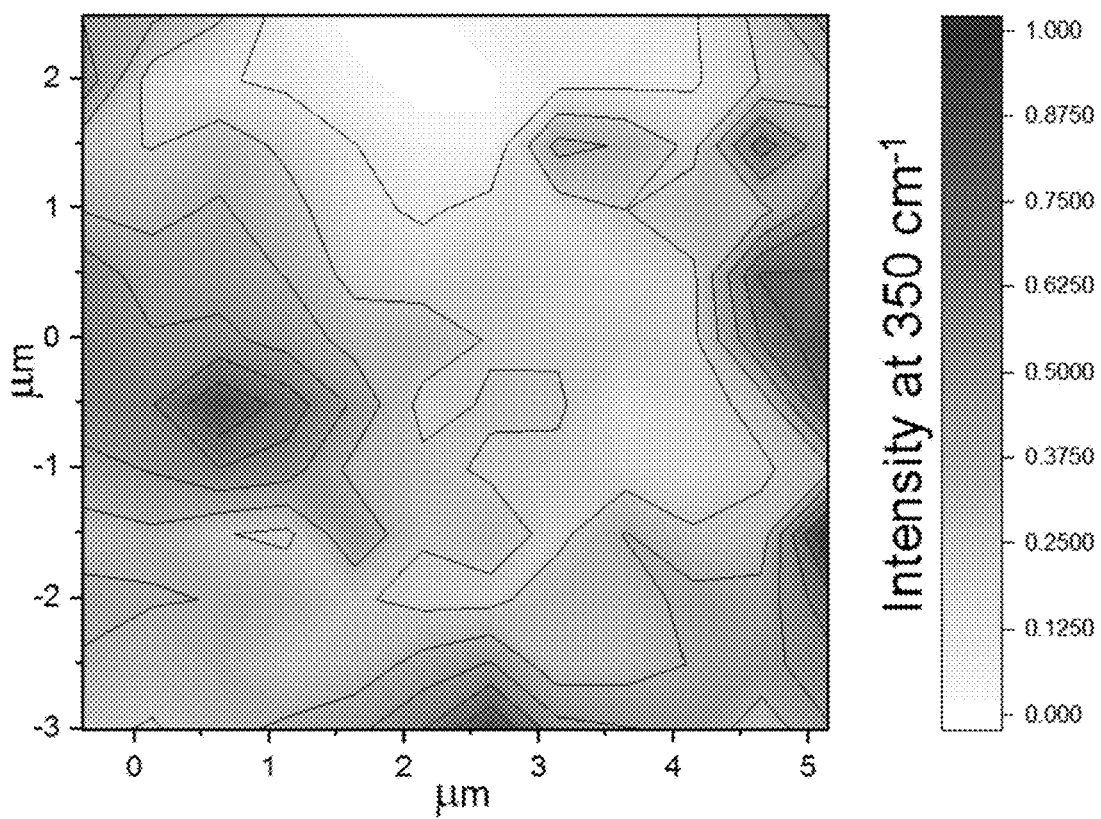
FIGS. 25A-25D depict Raman intensity mapping of PLLA 24 film with 0.5 wt % before (natural) tensile test. Intensity mapping at the same area (5 µm×5 µm) are presented for FIG. 25A: INT-WS$_2$ (at 350 cm$^{-1}$)
Figure 25B:
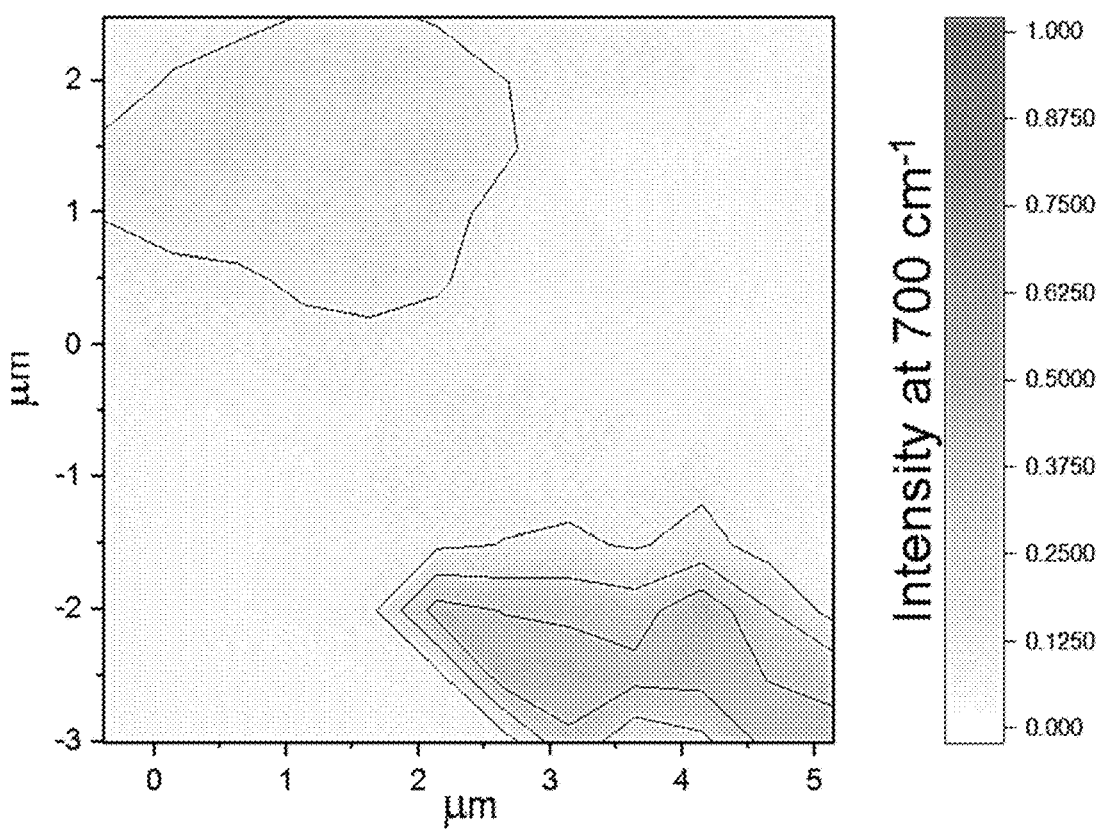
Figure 25C:
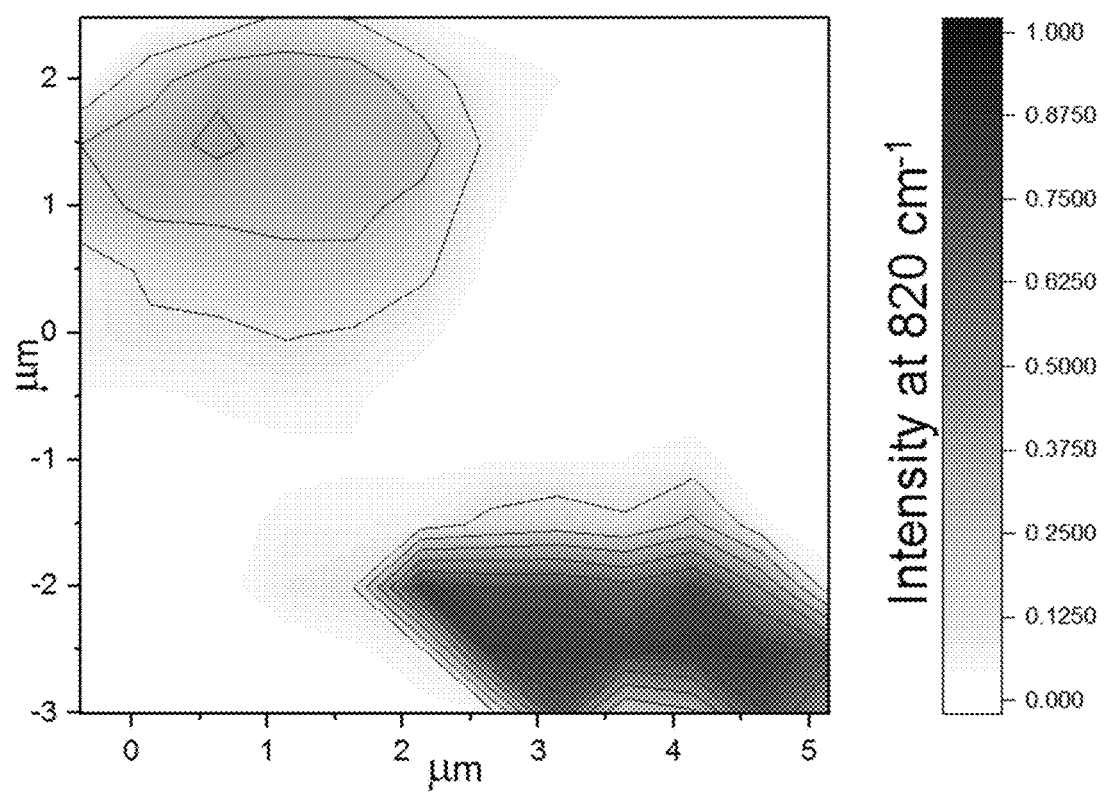
Figure 25D:
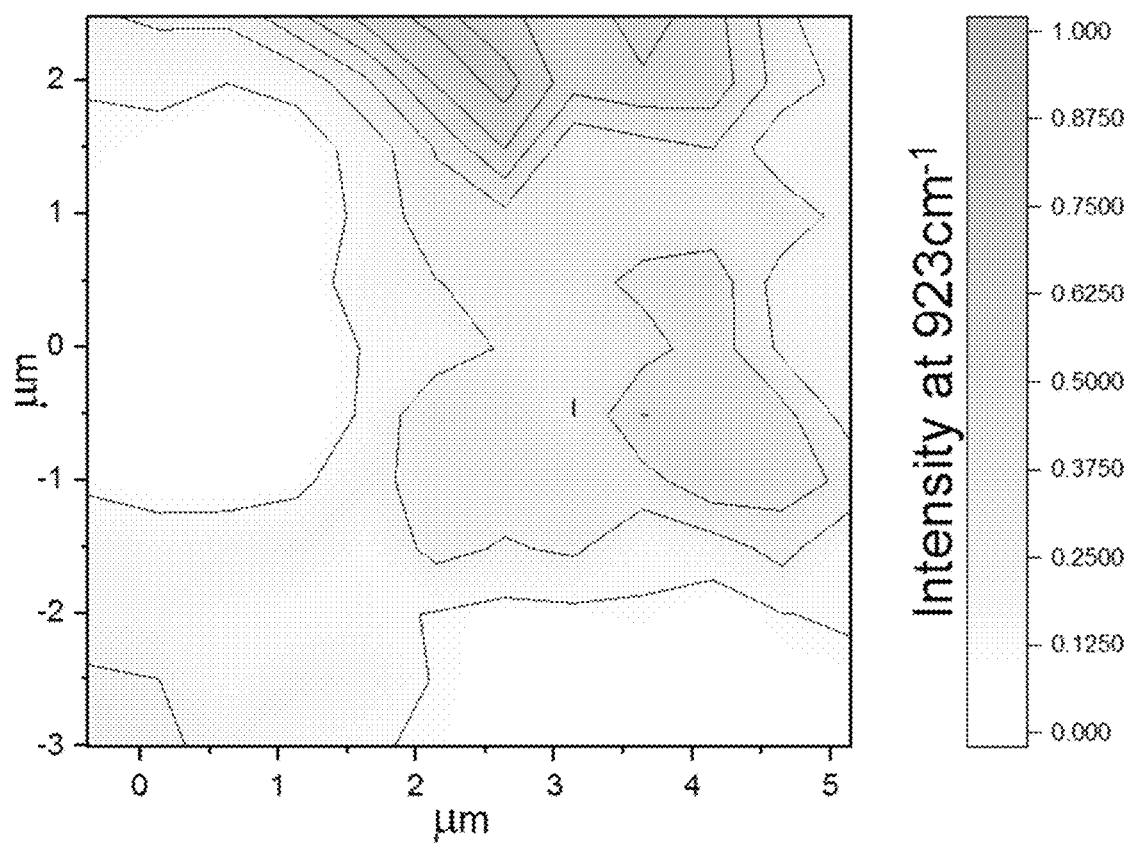
Figure 26A:
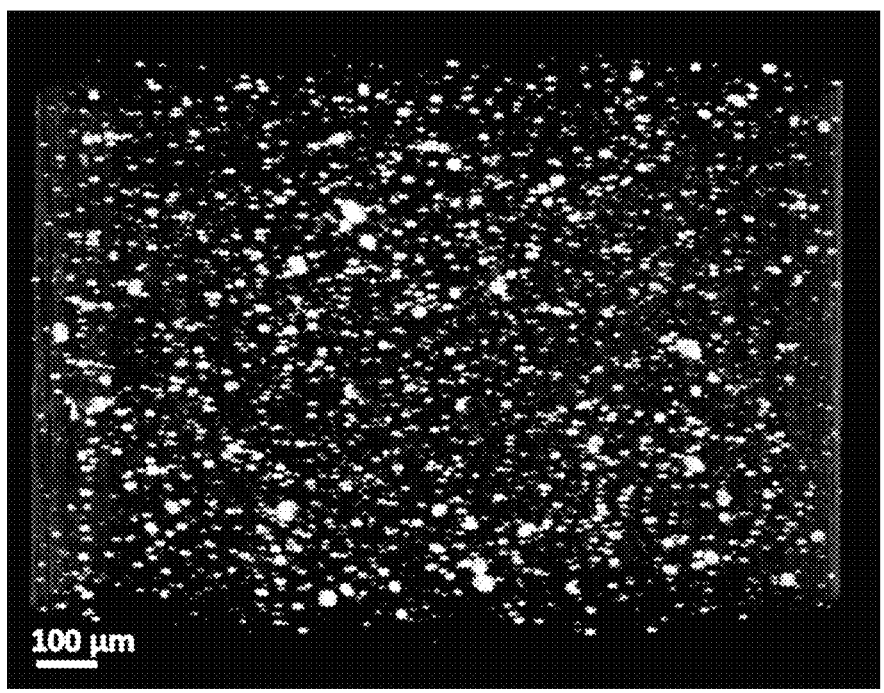
FIGS. 26A-26D depict p-XCT of pre-printed filament.
Figure 26B:
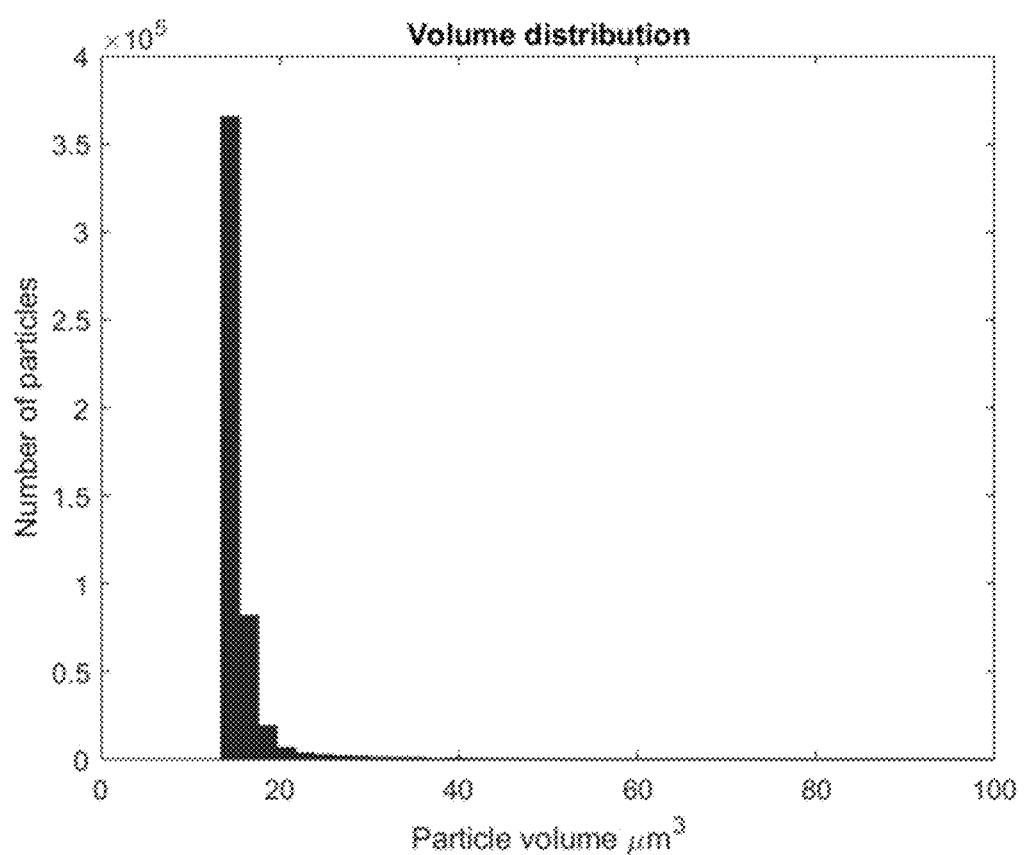
Figure 26C:
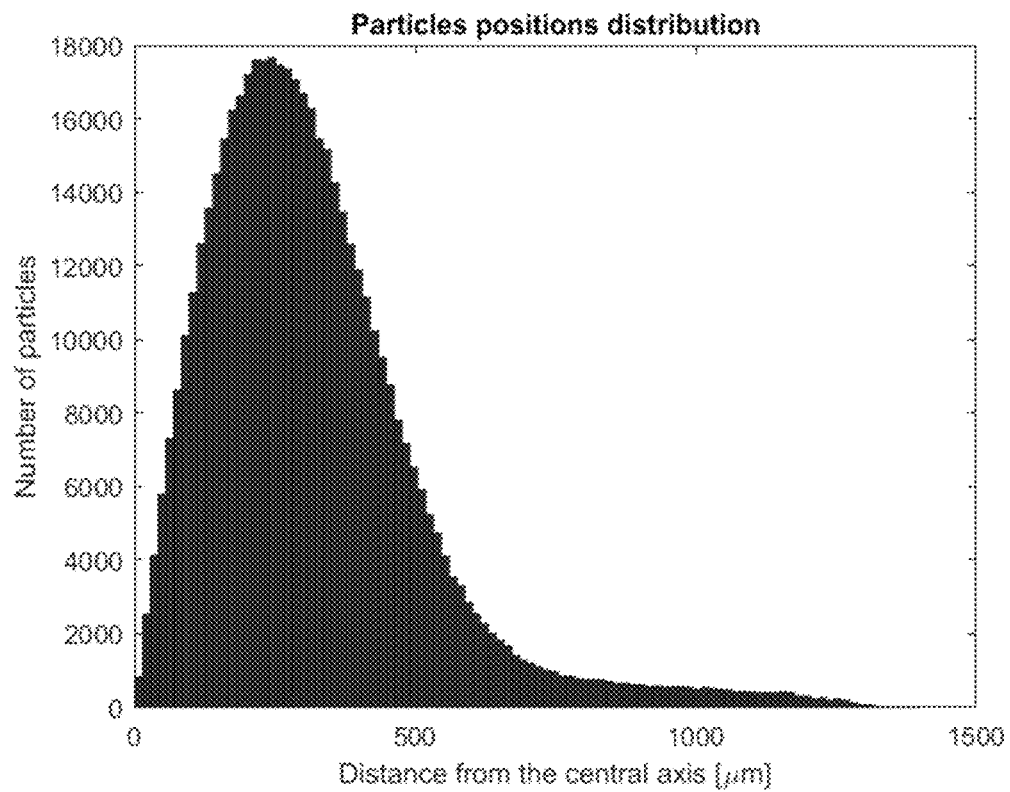
Figure 26D:
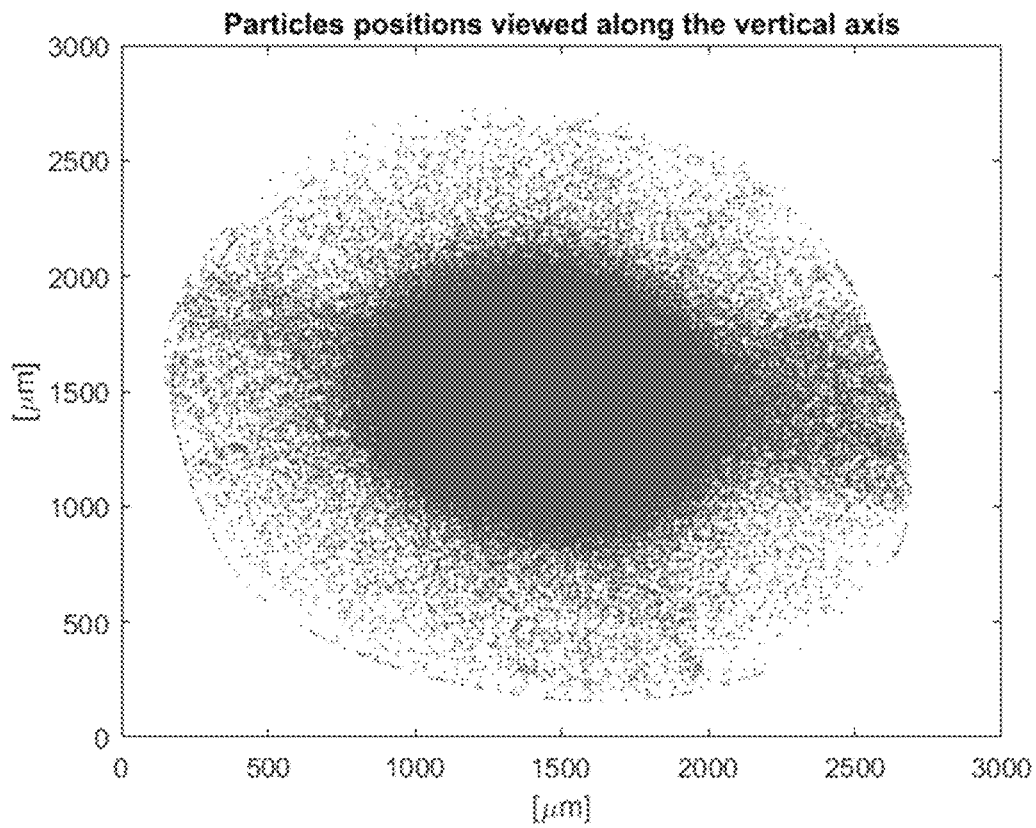
Figure 27A:
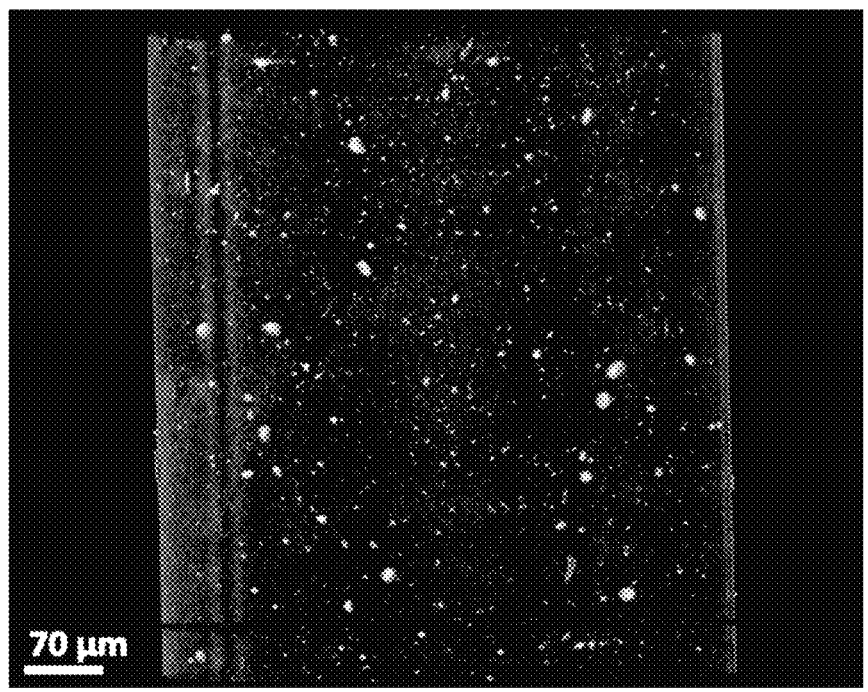
FIGS. 27A-27D depict: p-XCT of post-printed filament.
Figure 27B:
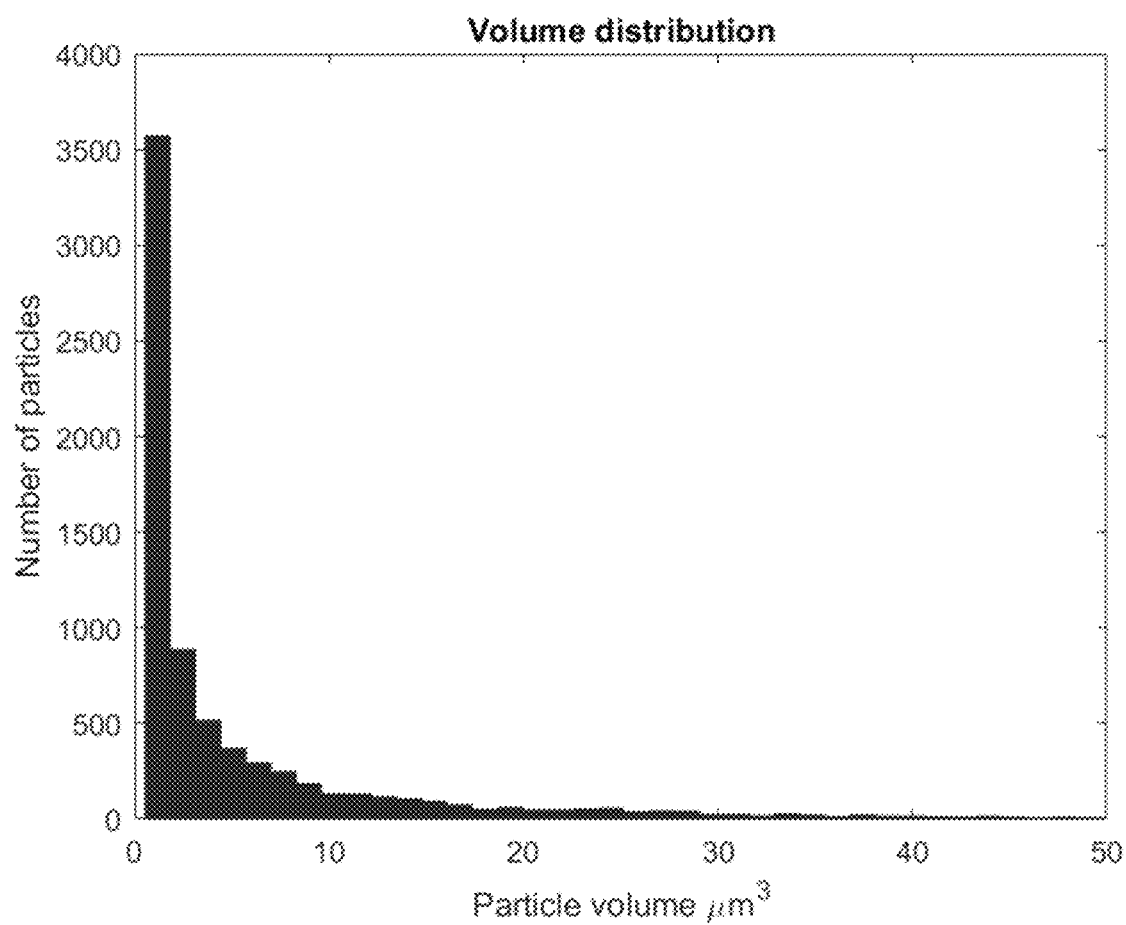
Figure 27C:
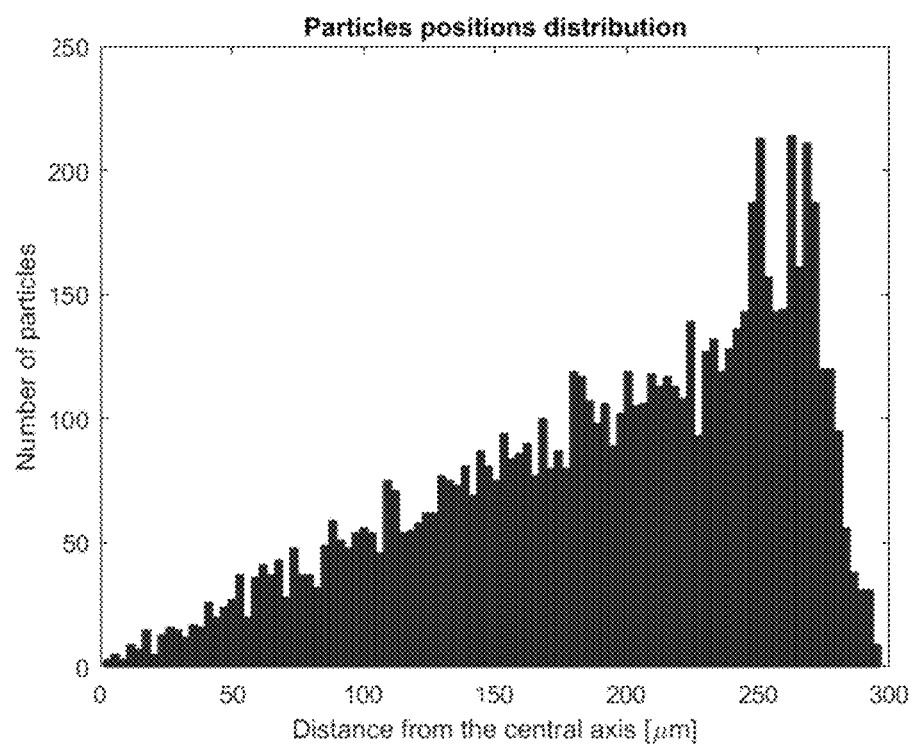
Figure 27D:
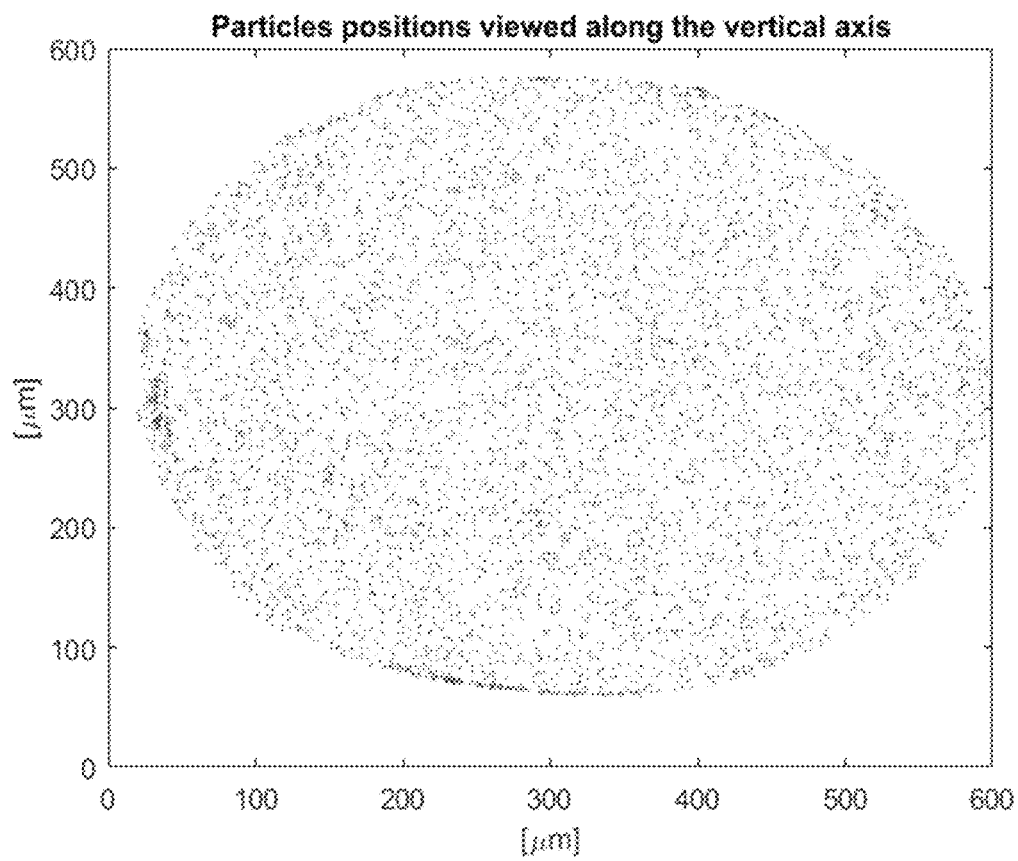

The Raman spectrum of PLA, including PLLA, was studied before (G. Kister, G. Cassanas, M. Vert, B. Pauvert, and A. Térol, "Vibrational analysis of poly(L-lactic acid)," J. Raman Spectrosc., vol. 26, no. 4, pp. 307-311, 1995; and G. Kister, G. Cassanas, and M. Vert, "Effects of morphology, conformation and configuration on the IR and Raman spectra of various poly(lactic acid)s," Polymer (Guildf)., vol. 39, no. 2, pp. 267-273, 1998). The Raman spectrum of INT-WS$_2$ has been reported in several studies, see O. Grinberg, S. Deng, E. Zussman, T. Livneh, and A. Zak, "Raman scattering from single WS2 nanotubes in stretched PVDF electrospun fibers," Phys. Chem. Chem. Phys., vol. 19, no. 28, pp. 18443-18451, 2017. Raman spectra of PLLA 24 films in three different situations: natural, partially stretched and fully stretched (close to the fracture) is displayed in FIG. 24.

The Raman spectra does not vary upon stretching and hence provides no evidence for any change in the composition and crystallinity of the specimen due to the stretching.

Furthermore, Raman mapping of the PLLA 24 with 0.5 wt % INT-WS$_2$ before tensile test (see Table 5 sample entry 4) is shown for four peaks: 350 (red-nanotubes), 700 (yellow-dicholoromethane), 820 (blue-monomers of lactic acid) and 923 (green-semicrystalline PLLA) cm$^{-1}$ are displayed in FIGS. 25A-25D. The intensity mapping for nanotubes of WS$_2$ (350 cm$^{-1}$) and for semicrystalline PLLA (973 cm$^{-1}$) shows correlation in the intenstiy maps for these two components and good compatibility between them. In addition, the intensities of the band lines at 700 and 820 cm$^{-1}$ associated with the presence of residual DCM solvent molecules (S. J. H. Chen and M. Schwartz, "Raman study of vibrational relaxation in dichloromethane and [2H2] dichloromethane," J. Chem. Soc. Faraday Trans. 2 Mol. Chem. Phys., vol. 81, no. 2, pp. 235-243, 1985) and monomers of lactic acid (G. Cassanas, M. Morssli, E. Fabregue, and L. Bardet, "Vibrational spectra of lactic acid and lactates," J. Raman Spectrosc., vol. 22, no. 7, pp. 409-413, 1991), are highly correlated. This result could suggest that the presence of solvent molecules residues prevented the completion of the polymerization of the lactic acid monomers.

Raman mapping of the stretched PLLA 24+INT indicated no monomer residues (not shown) left in the nanocomposite after the failure. The absence of the solvent moieties can be attributed to the weaker signal from the distorted sample, or perhaps to a solvent evaporation resulting from the thermal energy dissipated in the stretching of the specimen.

Example 14

Fused Deposition Modeling (FDM) Printing Using the Nanocomposites of This Invention Preparation of the Nanocomposites Filaments To prepare the nanocomposite filament, WS$_2$—INT (12.5 g; 1-20 micron long with a diameter of 30-150 nm) were initially vacuum annealed for 1.5 h at 150° C. Following the vacuum annealing, PLA pellets (5 kg; 4032D grade, NatureWorks, density of 1.24 g/cm$^3$, ReprapWorld, Netherlands) and the vacuum annealed WS$_2$—INT were dried in a vacuum oven at 50° C. overnight before processing. Then, PLA pellets were mixed with 0.5 wt % of WS$_2$—INT in the melt state using a lab-scale co-rotating twin screw extruder (EUROLAB Digital 16 'Prism', D=16 mm, L/D=24) operated at 160° C. and 60 rpm. The melted compound was continuously cooled down to solidify under cold water at 10° C., then pelletized—creating PLA/WS$_2$—INT composite pellets. Pellets of either neat PLA or PLA/WS$_2$—INT composite were processed into filaments of the desired diameter (2.85 mm) by extrusion at 160° C. and 60 RPM followed by water cooling at 10° C.

FDM Printing Process

PLA and PLA/WS$_2$—INT filaments (diameter of 2.85 mm) were printed using a Sigma R19 FDM printer (BCN3D Technology, Barcelona, Spain). Brass nozzles with 0.5 mm diameter were used with the printed temperature at 205° C. and platform temperature at 55° C. The printing head was set at the rate of 60 mm/s. Specimens were printed with no shell layer and the infill was set to 100%. Every printed specimen was sliced to G-code using BCN3D Cura 1.1.0 software. The samples were printed to films 5 mm wide and 50 mm long, to allow gauge length test at 30 mm. Also, wires with an average diameter of 0.5 mm were tested with a gauge length of 30 mm.

The dispersion of the nanotubes in the PLA matrix was imaged with a Zeiss Xradia 520 Versa (Zeiss X-ray Microscopy, Pleasanton, CA, USA), under working conditions of a source voltage (100 kV) and current (90 μA). Image processing and analysis were done with the Avizo software. The 2.35 mm diameter filament was imaged at 0.36 μm voxel size, while the 0.5 mm filament was imaged at 0.81 μm voxel size. The images were corrected for beam hardening.

Characterization of the Nanocomposites/Filaments Pre- and Post-Printing morphology The morphology of PLA/WS$_2$—NT composite before and after printing was compared using micro-X-ray computerized tomography (μ-XCT). The contrast between the heavy atoms of the WS$_2$—NT and the light carbon atoms in the polymer backbone allows for good separation between the materials even at the relatively low resolution (0.5 μm) of the instrument, in which individual nanotubes cannot be determined. Pre-printed filament (FIGS. 26A-26D), with an average diameter of 2.35 mm, exhibits very few large agglomerates overall, but most of the nanotubes are concentrated at the filament center—showing uneven dispersion of the nanotubes throughout the filament diameter. In contrast, the 0.5 mm diameter post-printed filament (FIGS. 27A-27D) exhibits even smaller WS$_2$-NT clusters that are now evenly dispersed along the filament diameter, apart from what appears to be dust artifact condensed around the hot, semi-liquid filament surface during printing. Comparing the PLA/WS2-NT pre- and post-printing suggest that one of the main advantages in using FDM for nanocomposites processing is the improved dispersion of nanoparticles without the need for solvent-supported dispersion.

Thermal Behavior

Thermal characterization was performed with DSC 250 (TA Instruments, New Castle, DE, USA). Both PLA and PLA with 0.5 wt % INT-WS2 were measured before and after printing, and compared to their respective solvent-cast (Example 8) Temperature and enthalpy calibrations were performed using indium. Samples 5 mg in weight were placed in an aluminum pan and measured against an empty pan as a reference. Measurements were carried out under 50 mL/min nitrogen flow rate according to the following protocol: First, heating from 30 to 200° C. and 3 min at 200° C. (in order to erase the thermal history). Then, cooling down to 30° C., and, finally, a 2nd heating until 200° C. All scans were performed at 10 C/min under 50 mL/min nitrogen flow rate. From the mid-point of the (heating scan) thermograms, the glass transition (Tg), cold crystallization (Tcc), and melting (Tm) temperatures were determined. The crystallization temperature (Tg) was determined from the cooling scan. The degree of crystallinity was calculated from the DSC curves in two ways:

1.

$$X_c = \frac{(\Delta H_m - \Delta H_{cc})}{\Delta H_m^\circ} \times 100\%$$

for heating[13], and

2.

$$(1 - \lambda) = \frac{\Delta H_c}{\Delta H_m^\circ}$$

for cooling[14].

$\Delta H_m$, $\Delta H_{cc}$ (heating), and $\Delta H_c$ (cooling) are the melting enthalpy, cold crystallization enthalpy, and crystallization enthalpy (J/g), respectively; $\Delta H_m^\circ$ is the heat of fusion for completely crystallized PLA (93 J/g).

Figure 28A:
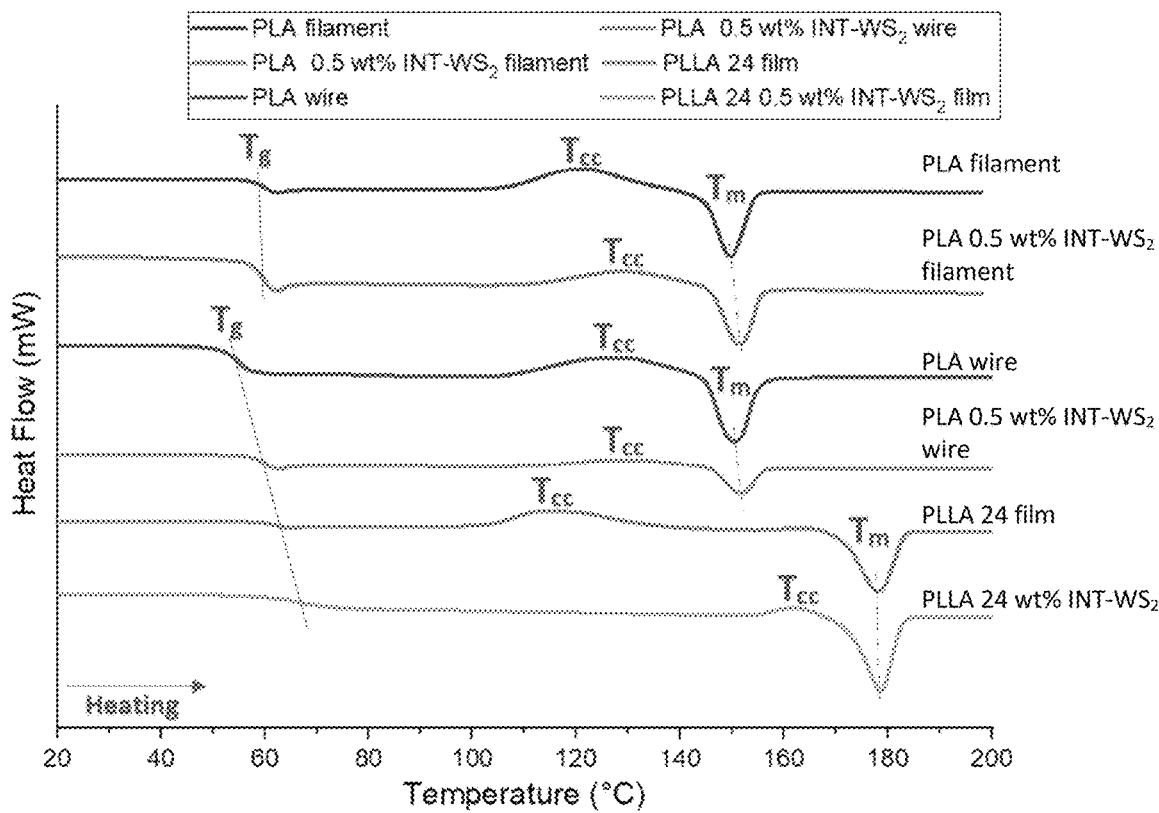
FIGS. 28A-28B depict DSC Thermograms of heating (FIG. 27A) and cooling (FIG. 27B) PLA and PLA/WS$_2$—NT pre- and post-printed filament, compared to solvent-casted thermograms [FIGS. 18A and 18B].
Figure 28B:
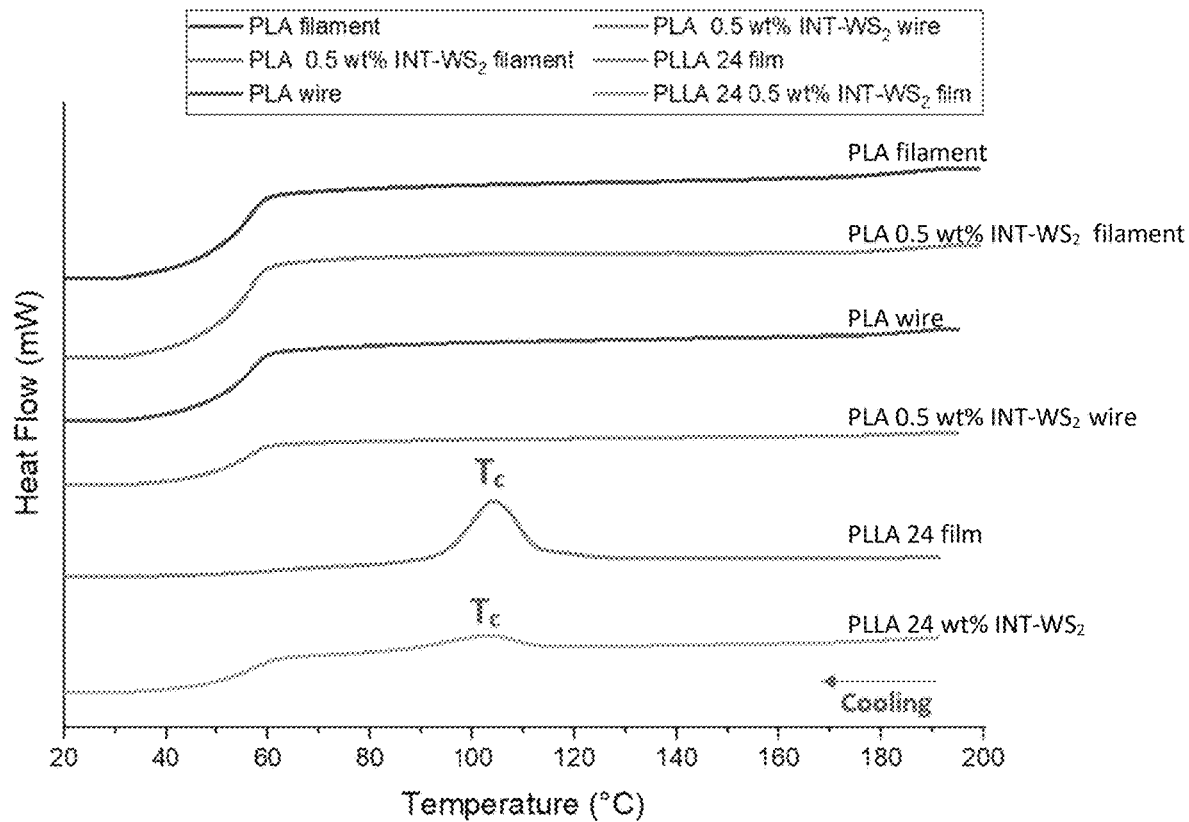

The thermal behavior of PLA with and without WS$_2$—NT, pre- and post-printing, as measured by Dynamic Scanning Calorimetry (DSC) (FIGS. 28A-28B) was used to calculate the glass transition, crystallization temperature and enthalpy, melting temperature and crystallinity percentage (Table 13). The results show negligible effect of the printing process on the composite crystallinity. It should be noted, that no changes were required in the printing parameters. Transition between the pure matrix and the nanocomposite in printing are thus simple and straight-forward.

TABLE 13

DSC parameters of PLA and PLA/WS$_2$-NT pre- and post-printed filament, compared to solvent-casted calculated parameters (Table 10).

| Method of Preparation | Sample | Tg (° C.) | Tcc (° C.) | Hcc (J/g) | Tm(° C.) | Hm (J/g) | Tc(° C.) | Hc (J/g) | % Cry (%) | (1-) (%) |
|---|---|---|---|---|---|---|---|---|---|---|
| 3D printing | PLA filament | 59.9 ± 0.5 | 121.4 ± 0.5 | 19.3 ± 2.5 | 149.5 ± 0.2 | 20.9 ± 1.5 | 91.1 ± 9.4 | 0.5 ± 0.1 | 1.7 ± 1.1 | 0.6 ± 0.1 |
|  | PLA with 0.5 wt % INT-WS$_2$ filament | 60.1 ± 0.1 | 128.8 ± 0.3 | 5.8 ± 0.3 | 151.5 ± 0.2 | 8.0 ± 0.6 | 99.3 ± 0.8 | 0.6 ± 0.1 | 2.3 ± 0.9 | 0.6 ± 0.1 |
|  | PLA wire | 59.9 ± 0.1 | 128.8 ± 0.1 | 25.5 ± 23.4 | 150.9 ± 0.6 | 26.1 ± 23.9 | 96.2 ± 2.0 | 0.7 ± 0.5 | 0.6 ± 0.5 | 0.8 ± 0.6 |
|  | PLA with 0.5 wt % INT-WS$_2$ wire | 60.1 ± 0.4 | 129.4 ± 0.3 | 5.8 ± 0.4 | 151.7 ± 0.5 | 7.5 ± 0.6 | 104.1 ± 1.3 | 0.4 ± 0.0 | 1.8 ± 0.5 | 0.5 ± 0.0 |
| Solvent casting | PLLA 24 | 61.7 ± 0.4 | 114.8 ± 0.3 | 32.4 ± 12.0 | 178.6 ± 0.4 | 33.9 ± 12.2 | 101.6 ± 0.4 | 2.0 ± 0.1 | 1.6 ± 0.2 | 2.1 ± 0.4 |
|  | PLLA 24 with 0.5 wt % INT-WS$_2$ | 65.5 ± 1.7 | 107.9 ± 7.9 | 3.1 ± 0.6 | 178.9 ± 0.3 | 37.9 ± 1.5 | 103.0 ± 0.9 | 30.6 ± 6.1 | 37.4 ± 2.1 | 32.9 ± 6.6 |

Comparing the DSC results to those of solvent-cast PLA and PLA/WS$_2$—NT show that FDM accelerates the highest degree of crystallinity in the printed and post-printed samples), most likely due to the much slower process of solvent evaporation that allows for larger crystals to grow. It is worth noting that dedicated-for-printing also reach over 30% crystallinity post-printing, so optimization of formulation might be helpful in achieving higher crystallinity.

Mechanical Tests

Mechanical tests on both extracted wires and printed films were performed using Instron-5944 (Instron, Norwood, MA, USA) equipped with a 10 N load-cell at room temperature and a stretching speed of 1 mm/min. The load and displacement were recorded by dedicated software provided by the manufacturer (Bluehill3, Norwood, MA, USA). Dog-bone samples (ASTM D638—Type IV) were 3D printed and tested using MTS-20/M tensile testing machine equipped with a 100 kN load-cell at room temperature and a stretching speed of 5 mm/min. Fifteen specimens of each type were tested, and the results are given as average values. The load and displacement were recorded by dedicated software provided by the manufacturer (TestWorks, Eden Prairie, Minnesota, USA).

Figure 29:
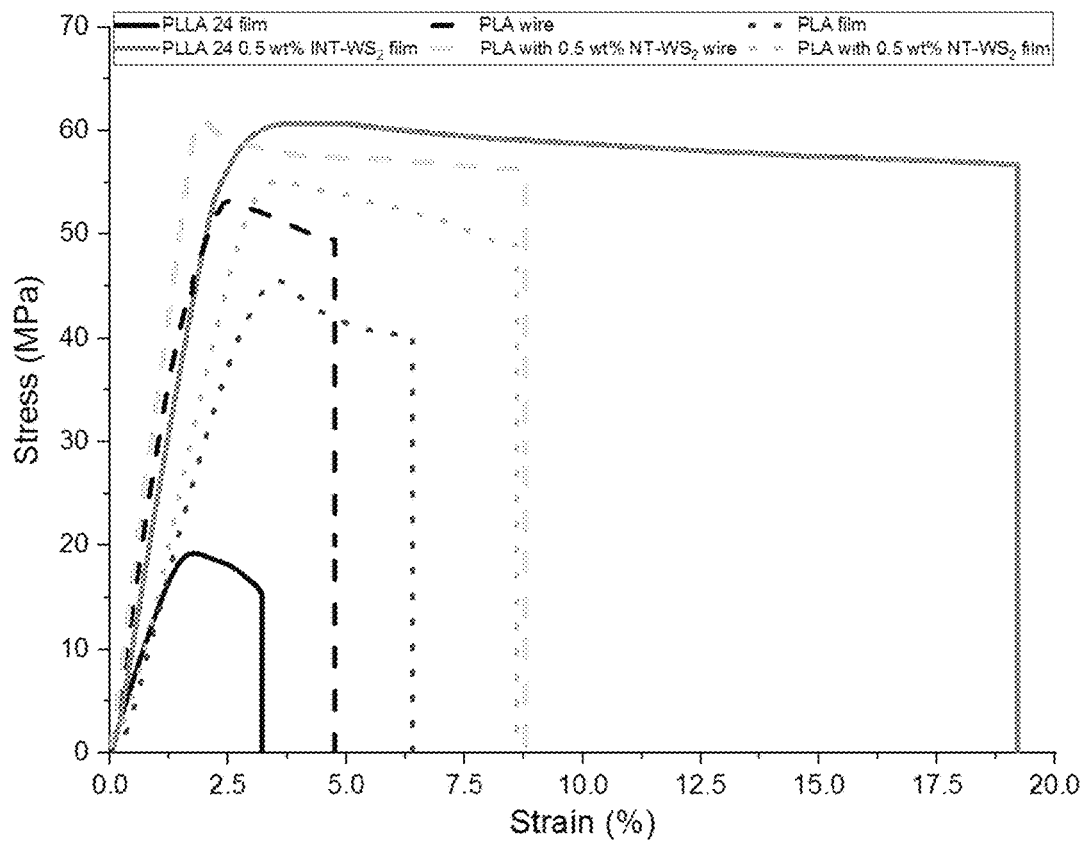
FIG. 29 presents stress-strain representing curves of PLA and PLA/WS$_2$—NT pre- and post-printed filament, compared to solvent-casted calculated parameters [FIGS. 3A and 3B].

The mechanical properties of printed PLA and PLA-$WS_2$—NT composite (FIG. 29 and Table 14) were also compared to those of solvent-cast films (Example 4, Table 4). The modulus and strength of PLA-$WS_2$ are significantly larger than those of pure PLA.

by DSC. Such increased crystallinity due to $WS_2$—NT addition was not observed in the fast-solidifying printed PLA/$WS_2$—NT, and so lower crystallinity also results in lower modulus and strength. The improved mechanical properties might also suggest better dispersion of the $WS_2$ INT by solvent-casting, countering the damage to the polymer matrix itself. As showed above, differences in dispersion can account to up to 5000 difference in strength, and 20% o in modulus, as befitting the difference between printed and cast PLA/$WS_2$—NT. The difference in dispersion can also explain the large error range of the printed PLA/$WS_2$—NT wires.

Unlike solvent casting, 3D printing allows the fabrication of many forms, including complex shapes.

Dog-Bone Mechanical Tests and Results:

Dog-bone samples (ASTM D638—Type IV) of PLA and PLA/$WS_2$—NT were 3D printed and tested using MTS-

TABLE 14

Mechanical properties of PLA and PLA/$WS_2$-NT pre- and post-printed filament, compared to solvent-casted properties (Table 4).

| Method of Preparation | Sample | Modulus (GPa) | Yield Strength (MPa) | Strain at failure (%) | Toughness (MPa*%) | Length (mm) | Thickness (mm) | Diameter (mm) |
|---|---|---|---|---|---|---|---|---|
| Solvent casting | PLLA 24 film | 1.4 ± 0.05 | 22.0 ± 4.1 | 3.5 ± 0.6 | 1.2 ± 0.3 | 30.0 ± 0.1 | 0.14 ± 0.1 | — |
| | PLLA 24 film with 0.5 wt % INT-$WS_2$ | 2.8 ± 0.2 | 60.9 ± 2.8 | 18.4 ± 5.2 | 5.7 ± 0.7 | 30.0 ± 0.1 | 0.10 ± 0.1 | — |
| 3D printing | PLA wire | 3.6 ± 0.4 | 52.8 ± 10.5 | 4.8 ± 2.8 | 1.6 ± 1.1 | 34.1 ± 0.3 | — | 0.5 ± 0.0 |
| | PLA with 0.5 wt % INT-$WS_2$ wire | 4.2 ± 0.5 | 63.2 ± 10.1 | 8.8 ± 7.5 | 4.7 ± 4.1 | 33.9 ± 1.1 | — | 0.5 ± 0.0 |
| | PLA film | 1.82 ± 0.17 | 46.76 ± 3.82 | 6.37 ± 1.95 | 2.11 ± 0.91 | 30.0 ± 0.1 | 0.22 ± 0.01 | — |
| | PLA with 0.5 wt % INT-$WS_2$ film | 2.19 ± 0.15 | 57.56 ± 4.83 | 8.63 ± 3.21 | 3.84 ± 1.78 | 30.0 ± 0.1 | 0.15 ± 0.01 | — |

Figure 30:
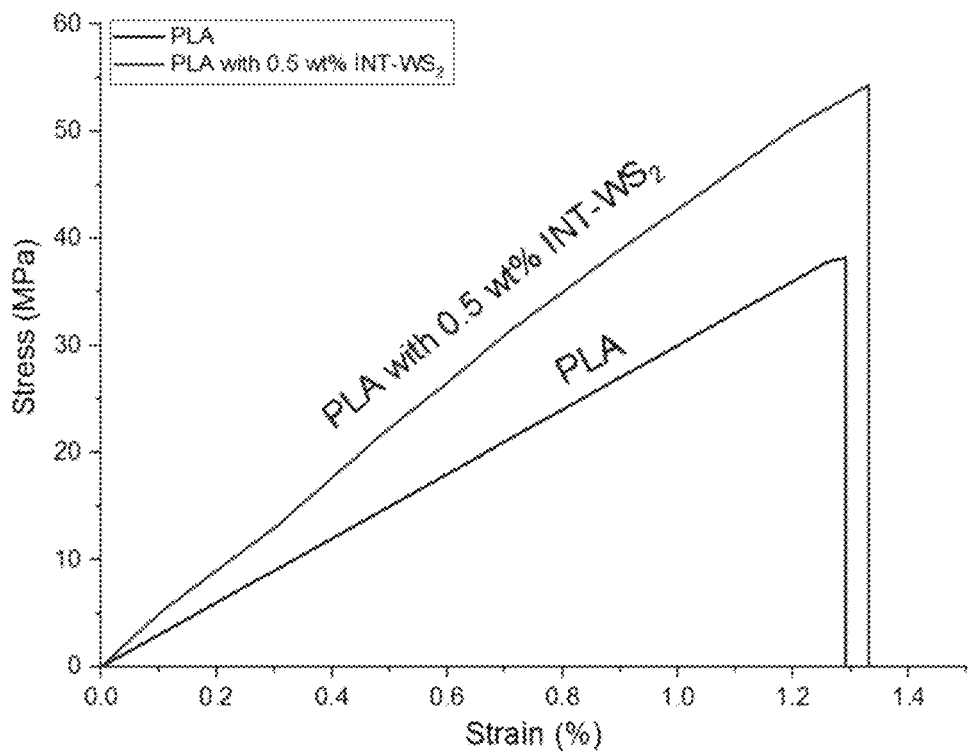
FIG. 30 presents stress-strain representing curves of PLA and PLA/WS$_2$—NT printed dog-bones.

Printed films of pure PLA outperform their solvent-cast respective in all parameters—modulus, strength and strain-at-failure. As extrusion and FDM do not require solvent—the mechanical properties improve. However, the gap is inverted, with higher modulus and strain-at-failure for the solvent-cast films (strength is similar) when $WS_2$ nanotubes are introduced to the composite. The most reasonable explanation to the favorable properties of the PLA/$WS_2$—NT solvent-cast film is its increased crystallinity, as confirmed 20/M tensile testing machine equipped with a 100 kN load-cell at room temperature and a stretching speed of 5 mm/min. 15 specimens of each type were tested (one typical curve is shown in FIG. 30 for each composition), and the results were given as average values (Table 15). The load and displacement were recorded by dedicated software provided by the manufacturer (TestWorks, Eden Prairie, Minnesota, USA).

TABLE 15

Mechanical properties of PLA and PLA/$WS_2$-NT printed dog-bones

| Sample | Modulus (GPa) | Yield Strength (MPa) | Elongation (%) | Toughness (MPa*%) | Width (mm) | Thickness (mm) |
|---|---|---|---|---|---|---|
| PLA | 3.37 ± 0.48 | 34.9 ± 7.08 | 1.29 ± 0.34 | 2.55 ± 1.11 | 3.46 ± 0.14 | 5.8 ± 0.38 |
| PLA 0.5 wt % INT-$WS_2$ | 4.45 ± 0.31 | 49.9 ± 5.84 | 1.33 ± 0.21 | 3.63 ± 0.97 | 3.28 ± 0.05 | 5.9 ± 0.36 |

Figure 31A:
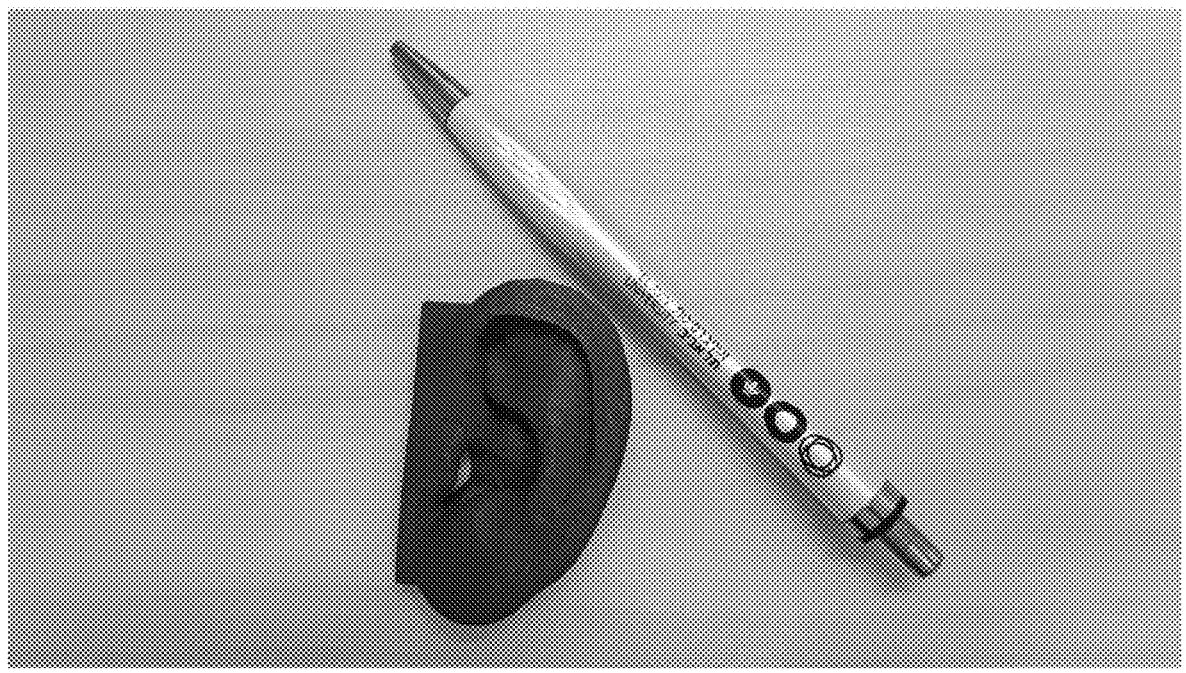
FIGS. 31A and 31B present FDM-printing using PLA/WS2-NT composite.
Figure 31B:
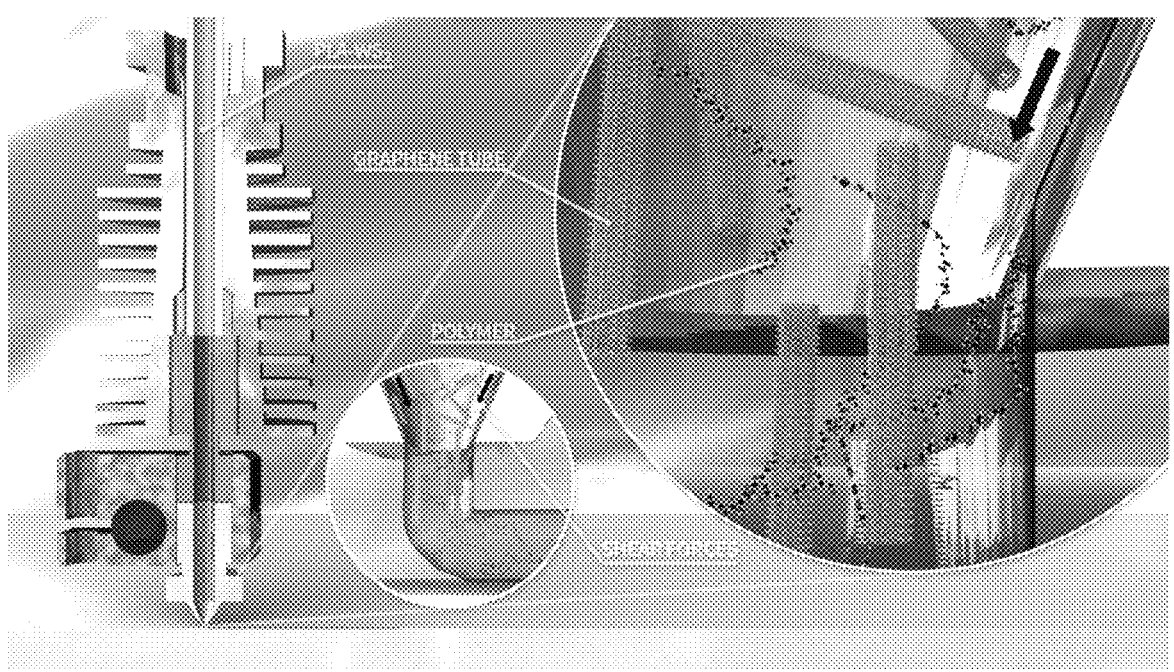

Thus, comparing 3D printed dog-bones specimens, the addition of $WS_2$—NT further increases the mechanical properties of the composite—more so than in printed films (FIG. 30). This enhanced reinforcement of thicker specimens supports the possibility of using printed PLA/$WS_2$—NT for life-size scaffolds, such as demonstrated in FIGS. 31A-31B.

Example 15

Electrical Conductivity Measurements

The volume resistivity of PLA and PLLA 24 composites was measured by two-probe and four-probe methods at room temperature in vacuum. The results are displayed in Table 16. The volume resistivity decreased as the nanotube's concentration increased. In addition, the volume resistivity was lower by four-probe then two-probe measurement. This could occur due to overcoming the contact resistance and the samples resistivity to the applied current. The volume resistivity of 3D printed PLA with 0.5 wt % INT-$WS_2$ was lower than the PLLA 24 with 0.5 wt % INT-$WS_2$ (solvent-casted), this could be possible due to better nanotubes distribution in the polymer matrix occur during the 3D printing.

The percolation threshold was calculated from the four-probe method results. The percolation threshold for solvent casted samples was 0.433 wt % (0.196 at %) and for 3D printed samples was 0.281 wt % (0.127 at %). The percolation threshold for 3D printed samples was lower compared to the solvent casted samples. This shows once more the nanotubes distribution enhanced in the polymer matrix during the 3D printing.

TABLE 16

Volume resistivity of PLLA 24 and PLA composites measured by two-probe and four-probe methods

| Method of preparation | sample | Two-probe [$\Omega$m] | Four-probe [$\Omega$m] |
|---|---|---|---|
| Solvent casted | PLLA 24 | 7.32E+09 ± 2.49E+08 | 9.79E+07 ± 4.67E+05 |
| | PLLA 24 with 0.5 wt % INT-$WS_2$ | 3.99E+09 ± 5.84E+06 | 2.64E+07 ± 4.21E+05 |
| | PLLA 24 with 1 wt % INT-$WS_2$ | 1.97E+09 ± 7.56E+06 | 8.36E+06 ± 3.61E+04 |
| | PLLA 24 with 5 wt % INT-$WS_2$ | 1.15E+08 ± 1.72E+05 | 9.69E+05 ± 3.52E+04 |
| 3D printed | PLA commercial | 1.28E+10 ± 2.38E+08 | 2.03E+07 ± 1.88E+05 |
| | PLA home-made | 2.34E+10 ± 8.79E+08 | 9.77E+06 ± 2.58E+05 |
| | PLA with 0.5 wt % INT-$WS_2$ | 6.53E+09 ± 1.76E+08 | 2.51E+06 ± 2.21E+04 |

Example 16

X-Ray Photoelectron Spectroscopy (XPS) Studies of INT-$WS_2$ Drying Processes

Three different treatments were performed for INT-$WS_2$:
Vacuum annealing for 2 h at 120° C. and storage in glovebox under nitrogen atmosphere.
Vacuum annealing for 2 h at 150° C. and storage in glovebox under nitrogen atmosphere.
HF acid: distilled water solution (1:10, v/v) treatment for 5 min. using a hook. Afterwards, each powder was washed 3 times with ethanol and acetone. The powder was dried in the hood and immediately was transferred and stored in glovebox under nitrogen atmosphere. anhydrous An XPS study was conducted for the $WS_2$ nanotubes drying processes. A distinguish is made between oxygen bound to hydrogen ($O_{H2O}$) and oxygen bound to tungsten $O_{W\text{-}O}$ in order to calculate the reduction in the water amount within the $WS_2$ nanotubes sample. It was found in all of the above processes that between 20-60% (molar percentage) reduction in the water amount (molar percentage) was achieved. This reduction is significant, showing that all of these processes are capable of producing anhydrous INT-$WS_2$ as defined hereinabove.

Example 17

Mechanical Properties of Nanocomposites of Initially Treated HF—INT-$WS_2$ with PLLA In this study, PLLA 24 and PLLA 24 with 0.5 wt % INT-$WS_2$ films were prepared as described above, with the exception that INT-$WS_2$ was initially treated with HF (hydrofluoric acid) instead of the vacuum annealing process at 150° C. for 1.5 hours:

first, the nanotubes were dispersed in DI (de-ionized water) for 3 min; secondly, the nanotubes were soaked in HF: DI solution with a ratio of 1:1 (v/v) for 5 mins., followed by washing the nanotubes 3 times with ethanol and acetone; and finally, the nanotubes were dried and stored under an inert environment.

The young modulus and yield stress values (Table 17) show improvement in the mechanical properties of PLLA24-INT-$WS_2$ compared to the PLLA24 samples. Accordingly, HF treatment is a feasible process to produce anhydrous INT-$WS_2$, as the anhydrous nature of the nanotubes is crucial in the making of the nanocomposites with the improved mechanical properties, as described further hereinabove.

TABLE 17

Mechanical properties of PLLA 24 and PLLA24-INT-WS2

| Specimen | Young's Modulus (GPa) | Yield stress (MPa) |
|---|---|---|
| PLLA 24 1 | 1.43 | 32.15 |
| PLLA 24 2 | 1.364 | 29.95 |
| PLLA 24 3 | 1.476 | 31.7 |
| PLLA 24 4 | 1.452 | 34.67 |
| PLLA 24 5 | 1.486 | 30.76 |
| Average | 1.44 | 31.85 |
| Standard deviation | 0.05 | 1.79 |
| PLLA 24 with 0.5 wt % IF-WS2 1 | 2.11 | 43.93 |
| PLLA 24 with 0.5 wt % IF-WS2 2 | 2.04 | 44.34 |
| PLLA 24 with 0.5 wt % IF-WS2 3 | 2.03 | 44.45 |
| PLLA 24 with 0.5 wt % IF-WS2 4 | 2.10 | 45.12 |
| PLLA 24 with 0.5 wt % IF-WS2 5 | 2.22 | 49.69 |
| Average | 2.10 | 45.51 |
| Standard deviation | 0.07 | 2.38 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A completely dried nanocomposite comprising a polymer and an anhydrous $MX_2$-based fullerene-like nanoparticles or nanotubes; wherein said polymer is selected from poly(lactic acid), poly (lactic-co-glycolic acid) or a combination thereof,
wherein M is Mo, W, Ta or Nb; and X is S, Se or Te;
wherein the weight percentage of the $MX_2$-based fullerene-like nanoparticles or nanotubes from the total weight of said nanocomposite is between 0.25% and 3%,
wherein the anhydrous $MX_2$-based fullerene-like nanoparticles or nanotubes is defined as the $MX_2$-based fullerene-like nanoparticles or nanotubes having been heated and/or vacuum annealed at a temperature of 60-200° C. for 0.5-3 hours;
wherein the composite has at least one of the following properties: modulus between 1.6-4 GPa; toughness (area below the stress-strain curve) between 1.1-40 MPa/%; static friction coefficient, $\mu_s$, between 0.055-0.08; kinetic friction coefficient, $\mu_s$, between 0.02-0.05; yield strength: between 15-75 MPa; and friction force reduced by between 10-99% compared to the polymer alone;
wherein the completely dried nanocomposite is prepared by:
dissolving the polymer in a first solvent;
dissolving the anhydrous MX2-based fullerene-like nanoparticles or nanotubes in a second solvent;
mixing together both of the solutions;
solvent casting the mixed solution; and
drying and/or annealing the mixed solution to obtain the nanocomposite for between 48 hours to 7 days; between 7-10 days; or between 10-14 days; and at between 30-40° C.; between 40-50° C.; between 50-60° C.; or between 60-70° C.; and
wherein the dissolved polymer is optionally dried prior to its dissolution step.

2. The completely dried nanocomposite of claim 1, wherein said polymer is poly(lactic acid) or poly(lactic-co-glycolic acid).

3. The completely dried nanocomposite of claim 2, wherein said poly(lactic acid) is poly(L-lactic acid), poly (D-lactic acid) or poly(DL-lactic acid); or said poly(lactic-co-glycolic acid) is poly(L-lactic-co-glycolic acid), poly(D-lactic-co-glycolic acid) or poly(DL-lactic-co-glycolic acid).

4. The completely dried nanocomposite of claim 2, wherein said poly(lactic acid) has an inherent viscosity of 3.8 or 2.4 dL/g.

5. The completely dried nanocomposite of claim 1, wherein said $MX_2$-based fullerene-like nanoparticles or nanotubes are $WS_2$ or $MoS_2$ fullerene-like nanoparticles or nanotubes.

6. The completely dried nanocomposite of claim 5, wherein said $MX_2$ nanotubes are $WS_2$ nanotubes.

7. The completely dried nanocomposite of claim 1, wherein said weight percentage of said $MX_2$-based fullerene-like nanoparticles or nanotubes from said nanocomposite is 0.25; 0.4; 0.5; 0.7; 0.8; 1; or 3.

8. A method for the preparation of a completely dried nanocomposite, said nanocomposite comprises an anhydrous $MX_2$-based fullerene-like nanoparticles or nanotubes and a polymer selected from poly(lactic acid), poly (lactic-co-glycolic acid) or a combination thereof, wherein M is Mo, W, Ta or Nb; and X is S, Se or Te; wherein the anhydrous $MX_2$-based fullerene-like nanoparticles or nanotubes is defined as the $MX_2$-based fullerene-like nanoparticles or nanotubes having been heated and/or vacuum annealed at a temperature of 60-200° C. for 0.5-3 hours wherein said method comprises:
dissolving the polymer in a first solvent;
dissolving said anhydrous $MX_2$-based fullerene-like nanoparticles or nanotubes in a second solvent;
mixing together both said solutions;
solvent casting said mixed solution; and
drying and/or annealing the mixed solution to obtain the nanocomposite for between 48 hours to 7 days; between 7-10 days; or between 10-14 days; and at between 30-40° C.: between 40-50° C.: between 50-60° C.: or between 60-70° C.; and
wherein the dissolved polymer is optionally dried prior to its dissolution step.

9. The method of claim 8, wherein the drying step of the mixed solution forms a film, and said film is further annealed to obtain the nanocomposite.

10. The method of claim 8, wherein said method further comprises treating said $MX_2$-based fullerene-like nanoparticles or nanotubes with surface-modifying agent before their dissolution in a second solvent.

11. The method of claim 10, wherein said surface-modifying agent is N-methyl-2-pyrrolidone (NMP), polyethylenimine (PEI), polyethylene glycol (PEG) or cetyltrimethylammonium bromide (CTAB).

12. The method of claim 8, wherein said first solvent or second solvent, each independently is dichloromethane or chloroform.

13. The completely dried nanocomposite of claim 1, for use in 3D printing.

14. A filament for 3D printing comprising a completely dried nanocomposite according to claim 1.

15. The filament of claim 14, wherein the filament is processed by Fused Deposition Modeling (FDM) 3D-printer.

16. A medical device or product comprising a completely dried nanocomposite according to claim 1.

17. The medical device or product of claim 16, selected from the group consisting of:
medical artificial replacement of tissues comprising: bone, bone cements and joints; patch on the skull; surgical mesh; breast implants; lenses; blood vessels; artificial heart valves; artificial skin; implants; intrauterine devices; shunts; catheters; stents; coating for subcutaneous implants; insulin pumps; contraceptives; pacemakers; tubing and cannulas used for intra venous infusion; tubing and cannulas used for dialysis; surgical drainage tubing; endotracheal tubes; sutures; surgical gloves; tips for ear examination; stethoscope ends and elements used by the medical personnel comprising: tooth brushes, tooth pick, dental floss, interdental and tongue brushes or plasticware for medical and research laboratories.

* * * * *